(12) United States Patent
Van Leeuwen et al.

(10) Patent No.: US 12,091,436 B2
(45) Date of Patent: *Sep. 17, 2024

(54) STEVIOL GLYCOSIDE TRANSPORT

(71) Applicant: DSM IP ASSETS B.V., Heerlen (NL)

(72) Inventors: Johannes Gustaaf Ernst Van Leeuwen, Echt (NL); Viktor Marius Boer, Echt (NL); Priscilla Zwartjens, Echt (NL); Jos Van Vugt, Echt (NL); René Marcel De Jong, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 42 days.

This patent is subject to a terminal disclaimer.

(21) Appl. No.: 18/167,119

(22) Filed: Feb. 10, 2023

(65) Prior Publication Data
US 2023/0227510 A1 Jul. 20, 2023

Related U.S. Application Data

(63) Continuation of application No. 17/051,299, filed as application No. PCT/EP2019/060897 on Apr. 29, 2019, now Pat. No. 11,608,364.

(30) Foreign Application Priority Data

Apr. 30, 2018 (EP) ..................................... 18170193

(51) Int. Cl.
C07K 14/39 (2006.01)
C12N 9/02 (2006.01)
C12P 19/56 (2006.01)

(52) U.S. Cl.
CPC ............ *C07K 14/39* (2013.01); *C12N 9/0042* (2013.01); *C12P 19/56* (2013.01); *C12Y 106/02004* (2013.01)

(58) Field of Classification Search
None
See application file for complete search history.

(56) References Cited

U.S. PATENT DOCUMENTS

| | | | |
|---|---|---|---|
| 8,691,554 B2 | 4/2014 | Boles et al. | |
| 10,604,743 B2 | 3/2020 | Boer et al. | |
| 2015/0031868 A1 | 1/2015 | Lehmann et al. | |
| 2016/0153017 A1 | 6/2016 | Van Der Hoeven et al. | |
| 2018/0230505 A1 | 8/2018 | Boer et al. | |
| 2018/0235263 A1 | 8/2018 | Boer et al. | |
| 2020/0283816 A1 | 9/2020 | Boer et al. | |

FOREIGN PATENT DOCUMENTS

| | | | |
|---|---|---|---|
| EP | 1499708 A1 | 1/2005 | |
| WO | 03/062430 A1 | 7/2003 | |
| WO | 04/099381 A2 | 11/2004 | |
| WO | 06/009434 A1 | 1/2006 | |
| WO | 2006096130 A1 | 9/2006 | |
| WO | 2013/110673 A1 | 8/2013 | |
| WO | 2014122328 A1 | 8/2014 | |
| WO | 2015/007748 A1 | 1/2015 | |
| WO | 2016023844 A1 | 2/2016 | |
| WO | 2016146711 A1 | 9/2016 | |
| WO | 2017/025649 A1 | 2/2017 | |
| WO | 2017025362 A1 | 2/2017 | |
| WO | 2017025648 A1 | 2/2017 | |
| WO | 2017/060318 A2 | 4/2017 | |
| WO | 2018/031955 A2 | 2/2018 | |

OTHER PUBLICATIONS

International Search Report Issued in Counterpart Application No. PCT/EP2019/060897, Mailed on Jul. 22, 2019. Biological Chemistry, vol. 272, No. 44, Oct. 31, 1997, pp. 27893-27901.
Bay et al., "Small multidrug resistance proteins: A multidrug transporter family that continues to grow" Biochimica et Bophsyica (2008) 1814-1838.
Humphrey et al., "Spatial organisation of four enzymes from Stevia rebaudiana that are involved in steviol glycoside synthesis" Plant Molecular Biology (2006) vol. 61: 47-62.
Krough et al., "Predicting Transmembrane Protein Topology with a Hidden Markov Mode: Application to Complete Genomes" JMB (2001) vol. 305: 567-580.
Mohamed et al., "UDP-dependent glycosyltransferases involved in the biosynthesis of steviol glycosides" Journal of Plant Physiology (2011) 1136-1141.
Saier et al., "The Transporter Classification Database" Nucleic Acids Research (2014) vol. 42: D251-D258.
Sonnhammer et al., "A hidden Markov model for predicting transmembrane helices in proved sequences" Sixth International Conference on Intelligent Systems for Molecular Biology (1998) 1-10.
Stephan Wilkens, "Structure and mechanism of ABC transporters" F1000 Prime Reports (2015) 1-9.
Nieng Yan, "Structural Biology of the Major Facilitator Superfamily Transporters" Annu. Rev. Bophys. (2015) vol. 44: 257-283.

*Primary Examiner* — Suzanne M Noakes
*Assistant Examiner* — Jae W Lee
(74) *Attorney, Agent, or Firm* — MCBEE MOORE & VANIK IP LLC

(57) ABSTRACT

The disclosure provides a recombinant cell capable of producing a steviol glycoside, wherein the cell comprises a nucleic acid coding for a variant of a parent polypeptide, wherein the variant has steviol glycoside transport mediating activity, wherein the variant comprises an amino acid sequence which, when aligned with the amino acid sequence of the parent polypeptide, comprises at least one modification of the amino acid residue corresponding to any of the amino acids in the amino acid sequence of the parent polypeptide, wherein the variant has an improved ability to produce rebaudioside M and optionally other steviol glycosides extracellularly if compared with the parent polypeptide when measured under the same conditions.

10 Claims, 3 Drawing Sheets
Specification includes a Sequence Listing.

STEVIOL GLYCOSIDE TRANSPORT

CROSS-REFERENCE TO RELATED APPLICATIONS

This application is a continuation application of U.S. application Ser. No. 17/051,299, filed on 28 Oct. 2020, which is the National Stage entry of International Application No. PCT/EP2019/060897, filed 29 Apr. 2019, which claims priority to European Patent Application No. 18170193.9, filed 30 Apr. 2018, the entire contents of each of which are incorporated herein by reference.

REFERENCE TO SEQUENCE LISTING SUBMITTED AS A COMPLIANT ASCII TEXT FILE (.xml)

A Sequence Listing is submitted herewith as an ASCII compliant text file named "2912919-539001_Sequence_Listing_ST26" created on Feb. 9, 2023 and having a size of 22,580 bytes as permitted under 37 C.F.R. § 1.821 (c). The material in the aforementioned file is hereby incorporated by reference in its entirety.

BACKGROUND

Field

The present disclosure relates to a recombinant cell capable of producing steviol glycoside. The disclosure also relates to a process for the preparation of a steviol glycoside, to a fermentation broth comprising a steviol glycoside, to steviol glycosides and steviol glycosides compositions and to food, feed or beverage comprising steviol glycosides or compositions. The disclosure further relates to a variant of a steviol glycoside transport polypeptide, to a nucleic acid coding for said variant and to a method to produce said variant.

Description of Related Art

The leaves of the perennial herb, *Stevia rebaudiana* Bert., accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in *Stevia* leaves where they may comprise from 10 to 20% of the leaf dry weight. Stevioside and rebaudioside A are both heat and pH stable and suitable for use in carbonated beverages and can be applied in many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in *Stevia* leaves. It may be about 200 times sweeter than sucrose. Rebaudioside M is a further high-potency diterpene glycoside sweetener. It is present in trace amounts in certain *Stevia* variety leaves, but has been suggested to have a superior taste profile if compared to the other steviol glycosides. In particular rebaudioside M seems to be lacking the bitter, liquorice after-taste which is typical of other steviol glycosides, in particular rebaudioside A.

Steviol glycosides have traditionally been extracted from the *Stevia* plant. In *Stevia*, (–)-kaurenoic acid, an intermediate in gibberellic acid (GA) biosynthesis, is converted into the tetracyclic diterpene steviol, which then proceeds through a multi-step glycosylation pathway to form the various steviol glycosides.

In *Stevia* plants yields may be variable and affected by agriculture and environmental conditions. Furthermore, Rebaudioside D and rebaudioside M, which have an improved sweetness and sensory profile if compared with rebaudioside A, are present only in traces in plant extracts.

Also, *Stevia* cultivation requires substantial land area, a long time prior to harvest, intensive labour and additional costs for the extraction and purification of the glycosides. All these aspects render the production of steviol glycosides from plant extract less sustainable and economically less attractive.

As a consequence, more recently, interest has grown in producing steviol glycosides using fermentative processes. WO2013/110673 and WO2015/007748 describe microorganisms that may be used to produce at least the steviol glycosides such as rebaudioside A, rebaudioside D and rebaudioside M.

Further improvement of such microorganisms is desirable in order that higher amounts of steviol glycosides may be produced and/or additional or new steviol glycosides and/or higher amounts of specific steviol glycosides and/or mixtures of steviol glycosides having desired ratios of different steviol glycosides is produced.

In particular, as recovery and purification of steviol glycosides from the fermentation broth can be complex whenever the microorganisms are unable or only partially able to export or secrete steviol glycosides outside the cell, there is a need for microorganisms with improved abilities to recombinantly produce steviol glycosides outside the cell.

WO2014/122328 A1 describes recombinant microorganisms able to produce steviol glycosides with altered expression of one or more endogenous transporter or transcription factor genes, or overexpressing one or more heterologous transporters, leading to increased excretion of steviol glycosides of interest.

WO2016023844 A1 discloses a recombinant host capable of synthesizing a steviol glycoside, comprising a gene encoding a transporter polypeptide and/or a gene encoding a transcription factor polypeptide that regulates expression of at least one transporter gene; wherein expression of the gene encoding the transporter polypeptide and/or the gene encoding the transcription factor polypeptide that regulates expression of at least one transporter gene is modified and the recombinant host transports at least a portion of the synthesized steviol glycoside from the host into a culture medium.

WO2017/025362 A1 describes a recombinant host cells capable of producing steviol glycoside comprising:
 (a) a gene encoding a Sugar Efflux Transporter (SET) polypeptide; and/or
 (b) a gene encoding a Sugar Transporter SWEET (SWEET) polypeptide; wherein at least one of the genes is a recombinant gene.

WO2017/025649 A1 and WO2017/025648 A1 discloses recombinant host cells wherein transporter genes from *Issatchenkia orientalis*, and of *Yarrowia lipolytica*, respectively, are overexpressed in order to increase steviol glycosides transport out of the cell. Alternatively such recombinant hosts are modified to reduce expression of said genes, to retain more steviol glycosides inside the cell which are then further glycosylated to steviol glycosides comprising a higher number of sugar moieties.

Despite the disclosures in the prior art, there is still a need for further microorganisms with improved abilities to recombinantly produce steviol glycosides outside the cell, in particularly for microorganisms which preferentially produce rebaudioside M outside the cell if compared with other steviol glycosides.

SUMMARY

In accordance with the present invention there is provided a variant of a parent polypeptide wherein the variant has steviol glycoside transport mediating activity, wherein the variant comprises an amino acid sequence which, when aligned with the amino acid sequence of the parent polypeptide, comprises at least one modification of an amino acid residue corresponding to any of the amino acids in the amino acid sequence of the parent polypeptide, wherein, when measured under the same conditions:
  a) the ratio between the molar concentration of rebaudioside M produced by a recombinant cell expressing the variant and the molar concentration of rebaudioside M produced by a reference cell is at least 0.1; and/or
  b) the ratio between the molar concentration of rebaudioside M and the molar concentration of rebaudioside A produced by a recombinant cell expressing the variant is higher than the ratio between the molar concentration of rebaudioside M and the molar concentration of rebaudioside A produced by a reference cell; and/or
  c) the ratio between the molar concentration of rebaudioside M and the molar concentration of total steviol glycosides produced by a recombinant cell expressing the variant is higher than the ratio between the molar concentration of rebaudioside M and the molar concentration of total steviol glycosides produced by a reference cell;
wherein a reference cell is a recombinant cell expressing the parent polypeptide.

DESCRIPTION OF THE SEQUENCE LISTING

Figure 1:
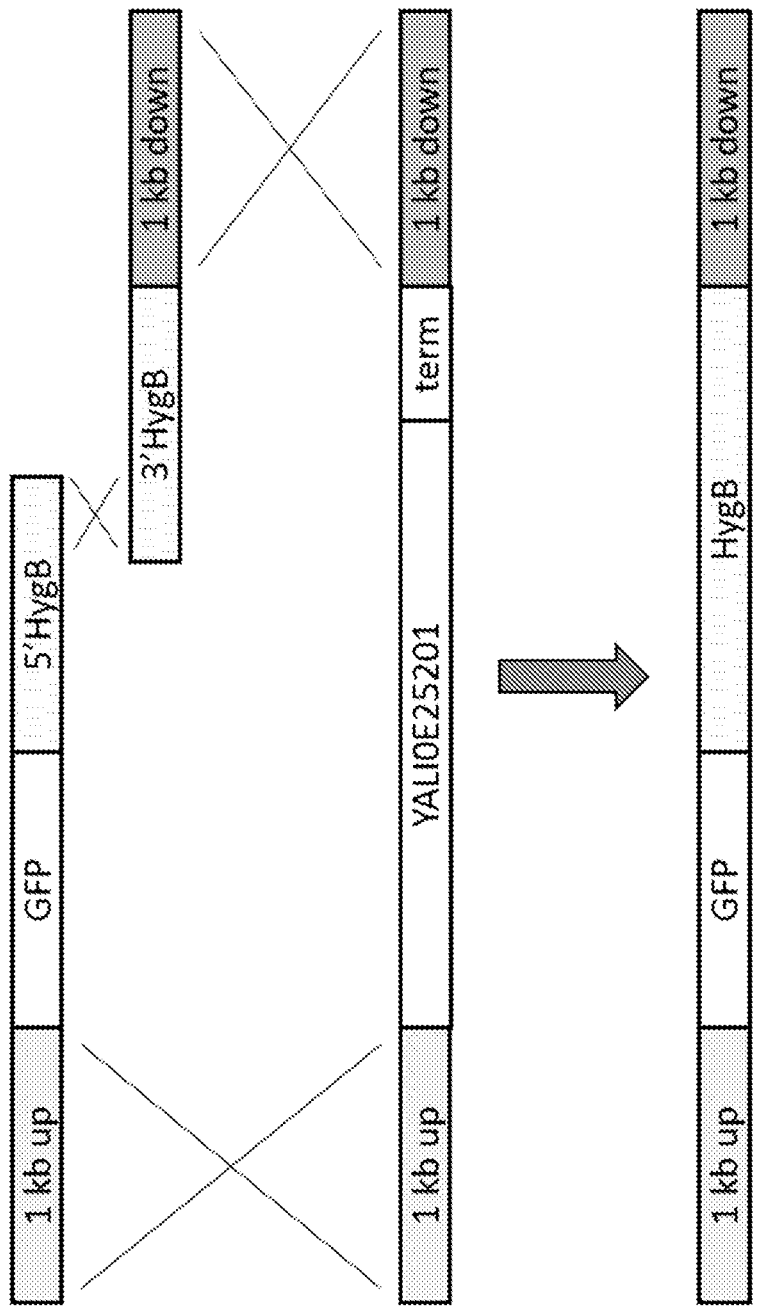
FIG. 1 depicts the strategy used to delete the endogenous transporter YALIOE25201 as defined in SEQ ID 1 from the *Yarrowia lipolytica* strain STVP001.

SEQ ID NO: 1 sets out the polynucleotide sequence of the Open Reading Frame (ORF) belonging to the *Yarrowia lipolytica* transporter YALIOE25201, containing a single intron.

SEQ ID NO: 2 sets out the genomic sequence of the *Yarrowia lipolytica* transporter YALIOE25201 comprising a 1000 bp flanking sequence upstream of the ORF, the ORF and, downstream of the ORF, the terminator sequence (300 bp) followed by a 999 bp flanking sequence.

SEQ ID NO: 3 sets out the amino sequence of the endogenous *Yarrowia lipolytica* transporter YALIOE25201.

SEQ ID NO: 4 sets out the amino acid sequence of a Truncated 3-hydroxy methylglutaryl coenzyme A reductase over-expressed in *Yarrowia lipolytica* strains STVP001 and STVP002.

SEQ ID NO: 5 sets out the amino acid sequence of a variant geranylgeranyl-diphosphate synthase over-expressed in *Yarrowia lipolytica* strains STVP001 and STVP002.

SEQ ID NO: 6 sets out the amino acid sequence of a variant kaurenoic acid 13-hydroxylase over-expressed in *Yarrowia lipolytica* strains STVP001 and STVP002.

DETAILED DESCRIPTION OF A PREFERRED EMBODIMENT

The inventors have surprisingly found that it is possible to modify a steviol glycoside transport protein to yield a variant polypeptide with improved ability to mediate steviol glycoside transport. In particular the variant has, if compared with the parent polypeptide, an improved ability to mediate transport of rebaudioside M outside the cell if compared to the ability to mediate transport of other steviol glycosides. As a consequence the fermentation broth of a recombinant cell expressing the variant polypeptide is enriched in rebaudioside M if compared with a fermentation broth of a recombinant cell expressing the parent polypeptide. The disclosure therefore allows the production of steviol glycoside compositions which are enriched in rebaudioside M content without the need of complex recovery and purification processes as said composition can be directly recovered from the fermentation broth, without prior disruption of the recombinant cells.

It is known that ABC transporters are usually rather a specific and promiscuous types of transporters. For example it was found that an ABC type of transporter isolated from *Yarrowia lipolytica* was efficient in transporting steviol glycosides outside the cell (WO2017/025648) in a recombinant cell. This latter observation was in itself surprising as *Yarrowia lipolytica* does not naturally produce steviol glycosides. Even more surprisingly the inventors have now found that it is possible to engineer an ABC transporter to make it more specific, e.g. more specific towards certain types of steviol glycosides such as e.g. rebaudioside M.

The disclosure provides in a first aspect a variant of a parent polypeptide wherein the variant has steviol glycoside transport mediating activity, wherein the variant comprises an amino acid sequence which, when aligned with the amino acid sequence of the parent polypeptide, comprises at least one modification of an amino acid residue corresponding to any of the amino acids in the amino acid sequence of the parent polypeptide, wherein, when measured under the same conditions:
  a) the ratio between the molar concentration of rebaudioside M produced by a recombinant cell expressing the variant and the molar concentration of rebaudioside M produced by a reference cell is at least 0.1; and/or
  b) the ratio between the molar concentration of rebaudioside M and the molar concentration of rebaudioside A produced by a recombinant cell expressing the variant is higher than the ratio between the molar concentration of rebaudioside M and the molar concentration of rebaudioside A produced by a reference cell; and/or
  c) the ratio between the molar concentration of rebaudioside M and the molar concentration of total steviol glycosides produced by a recombinant cell expressing the variant is higher than the ratio between the molar concentration of rebaudioside M and the molar concentration of total steviol glycosides produced by a reference cell;
wherein a reference cell is a recombinant cell expressing the parent polypeptide. The disclosure also provides a nucleic acid sequence coding for the variant according to the first aspect.

The disclosure provides as well a variant of a parent polypeptide wherein the variant has steviol glycoside transport mediating activity, wherein the variant comprises an amino acid sequence which, when aligned with the amino acid sequence set out in SEQ ID NO: 3, comprises at least one modification of an amino acid residue corresponding to any of amino acids, 15, 19, 26, 29, 31, 32, 33, 37, 46, 56, 59, 107, 135, 136, 141, 145, 148, 150, 151, 153, 199, 200, 204, 206, 207, 210, 211, 255, 257, 258, 262, 267, 268, 272, 273, 276, 277, 278, 281, 282, 283, 284, 292, 294, 296, 297, 298, 299, 300, 302, 303, 306, 307, 309, 310, 311, 315, 318, 319, 320, 321, 322, 323, 324, 326, 328, 375, 376, 378, 379, 380, 382, 384, 386, 387, 389, 408, 410, 411, 413, 414, 415, 416, 417, 419, 420, 421, 422, 423, 424, 425, 427, 428, 429, 853, 854, 857, 859, 862, 864, 869, 890, 891, 892, 894, 903, 906, 968, 969, 972, 974, 977, 986, 996, 998, 999, 1001, 1003, 1004, 1010, 1012, 1016, 1017, 1018, 1019, 1020, 1021, 1059, 1060, 1061, 1062, 1063, 1075, 1076, 1107, 1108, 1111, 1112, 1115, 1118, 1120, 1123, 1127, 1128, 1179, 1200, said positions being defined with reference to the amino acid sequence set out in SEQ ID NO: 3.

In one embodiment the parent polypeptide and the variant polypeptide both have steviol glycoside transport mediating activity.

The disclosure provides in a second aspect a method to produce a variant polypeptide according to the first aspect comprising:
a) providing a parent polypeptide, optionally wherein the parent polypeptide has steviol glycoside transport mediating activity;
b) modifying in the parent polypeptide sequence at least one amino acid residue to yield a variant polypeptide sequence, optionally wherein the modification in the parent polypeptide sequence occurs in a portion of a sequence which corresponds to a helical transmembrane region; and optionally
c) selecting a variant polypeptide which when expressed in a recombinant cell has steviol glycoside transport mediating activity and has the following characteristics:
i) the ratio between the molar concentration of rebaudioside M produced by a recombinant cell expressing the variant and the molar concentration of rebaudioside M produced by a reference cell is at least 0.1; and/or
ii) the ratio between the molar concentration of rebaudioside M and the molar concentration of rebaudioside A produced by a recombinant cell expressing the variant is higher than the ratio between the molar concentration of rebaudioside M and the molar concentration of rebaudioside A produced by a reference cell; and/or
iii) the ratio between the molar concentration of rebaudioside M and the molar concentration of total steviol glycosides produced by a recombinant cell expressing the variant is higher than the ratio between the molar concentration of rebaudioside M and the molar concentration of total steviol glycosides produced by a reference cell;
wherein a reference cell is a recombinant cell expressing the parent polypeptide, optionally wherein the molar concentration of rebaudioside M, rebaudioside A and total steviol glycosides in the ratio's according to i), ii), and iii) is the molar concentration produced extracellularly.

The disclosure provides in a third aspect a recombinant cell capable of producing a steviol glycoside, wherein the cell comprises a nucleotide sequence coding for the variant of the first aspect.

In yet a further aspect the disclosure provides a method to produce a recombinant cell capable of producing a steviol glycoside according to the third aspect, wherein the cell comprises a polynucleotide sequence coding for a variant of a parent polypeptide according to the first aspect, said method comprising: a) providing a cell; and b) modifying or transfecting said cell with a nucleic acid or with a nucleic acid construct coding for the variant polypeptide according to the first aspect, yielding a recombinant cell according to the third aspect.

In further aspects, the disclosure provides:
a nucleic acid coding for the variant according to the first aspect and a nucleic acid construct coding for the variant polypeptide according to the first aspect
a process for the preparation of a steviol glycoside which comprises fermenting a recombinant cell according to the third aspect;
a fermentation broth comprising a steviol glycoside obtainable by said process for the preparation of a steviol glycoside;
a steviol glycosides obtainable by said process for the preparation of a steviol glycoside;
a composition comprising one or more of said steviol glycosides;
a foodstuff, feed or beverage comprising said steviol glycoside or composition.

DETAILED DESCRIPTION

Variant Polypeptides and Nucleic Acids Coding for Said Variants

The disclosure provides in a first aspect a variant of a parent polypeptide wherein the variant has steviol glycoside transport mediating activity, wherein the variant comprises an amino acid sequence which, when aligned with the amino acid sequence of the parent polypeptide, comprises at least one modification of an amino acid residue corresponding to any of the amino acids in the amino acid sequence of the parent polypeptide, wherein, when measured under the same conditions:
a) the ratio between the molar concentration of rebaudioside M produced by a recombinant cell expressing the variant and the molar concentration of rebaudioside M produced by a reference cell is at least 0.1; and/or
b) the ratio between the molar concentration of rebaudioside M and the molar concentration of rebaudioside A produced by a recombinant cell expressing the variant is higher than the ratio between the molar concentration of rebaudioside M and the molar concentration of rebaudioside A produced by a reference cell; and/or
c) the ratio between the molar concentration of rebaudioside M and the molar concentration of total steviol glycosides produced by a recombinant cell expressing the variant is higher than the ratio between the molar concentration of rebaudioside M and the molar concentration of total steviol glycosides produced by a reference cell;

wherein a reference cell is a recombinant cell expressing the parent polypeptide.

The variant polypeptide according to the disclosure and optionally the parent polypeptide are polypeptides identified as having steviol glycoside transport mediating activity. For the purpose of this disclosure, a polypeptide having steviol glycoside transport mediating activity (i.e. a polypeptide which mediates steviol glycoside transport) is one which has an effect on transport of one or more steviol glycosides across a cell membrane. The effect may be direct, i.e. the polypeptide may be a transporter protein or comprise a functional transporter region. Alternatively, the effect may be indirect, i.e. the polypeptide is not a transporter protein, but its activity nevertheless has an effect on steviol glycoside transport.

Typically, the effect will be such that increasing the level of expression of the polypeptide having steviol glycoside transport mediating activity increases the amount of transport of one or more steviol glycosides across the membrane of a cell (in comparison with a corresponding cell having a lower level of expression of the polypeptide). Conversely, decreasing the level of expression of the polypeptide may decrease the amount of transport of one or more steviol glycosides across the membrane of a cell (in comparison with a corresponding cell having a higher level of expression of the polypeptide).

Typically, the variant polypeptide and optionally the parent polypeptide may be a transport protein or transporter. A transporter (also referred to as transport protein, transporter protein or membrane transport protein) is a protein which is involved in the movement of compounds across a biological membrane in a cell. Depending on the topology assumed by the transport protein within the membrane they can be classified in channels or pore formers on the one hand and in carriers on the other hand. While channels are simultaneously open or closed on both sides of the membrane and allow passive diffusion through the membrane carriers are not simultaneously open to both sides of the membrane and they are able to transport compounds through the biological membrane against a chemical gradient. The latter can occur through primary active transport (which requires energy released from a coupled chemical reaction inside the cell such as ATP hydrolysis) or secondary active transport which involves the use of an electrochemical potential of a co-transporting ion or solute and does not require energy produced by the cell.

Transport proteins are transmembrane proteins and are known to those skilled in the art. Transporter proteins are classified according to a classification system which is approved by the International Union of Biochemistry and Molecular Biology (Saier et al. 2014) and it is known to those skilled in the art. The classification system can be consulted on-line through the Transporter Classification Database (www.tcdb.org/). According to the disclosure the variant polypeptide and optionally the parent polypeptide may be a transport protein as classified by the Trasporter Classification Database. In one embodiment the variant polypeptide and optionally the parent polypeptide may be a transport protein belonging to any of the classes: TC1 transporter (Channels/Pores transporters); TC2 transporter (Electrochemical Potential Driven transporters); TC3 transporter (Primary Active transporters); TC4 transporter (Group Translocators); TC5 transporters (Transmembrane Electorn Carriers); TC8 transporter (Accessory Factors Involved in Transport); or TC9 transporter (Incompletely Characterized Transport Systems).

According to the Transporter Classification Database transport systems are classified on the basis of five criteria, and each of these criteria corresponds to one of the five numbers or letters within the TC number for a particular type of transporter. A transporter is indicated according to the following numbering TCn.m.x.y.z.; wherein n, m, x, y and z have the following meaning: n (a number) corresponds to the transporter class; m (a letter) corresponds to the transporter subclass; x (a number) corresponds to the transporter family (or superfamily); y (a number) corresponds to the subfamily in which a transporter is found, and z corresponds to the substrate or range of substrates transported.

In an embodiment the variant polypeptide and optionally the parent polypeptide is a transport protein belonging to any of the classes: TC1 transporter (Channels/Pores transporters); TC2 transporter (Electrochemical Potential Driven transporters); TC3 transporter (Primary Active transporters); TC4 transporter (Group Translocators); TC5 transporters (Transmembrane Electron Carriers); TC8 transporter (Accessory Factors Involved in Transport); or TC9 transporter (Incompletely Characterized Transport Systems) and belonging to any of the subclasses, superfamilies, families, or subfamilies therein. Between the major types of transporter proteins are ATP-Binding Cassettes (ABC) transporters (Wilkens 2015), Major Facilitator Superfamily (MFS) transporters (Yang 2015), Small Multidrug Resistance (SMR) transporters (Bay et al. 2007), transporters belonging to the Resistance-Nodulation-Cell division (RND) family, and Multi-Antimicrobial-Extrusion Proteins (MATE). ABC transporters are one of the largest families of transporters in both prokaryotes and eukaryotes and are known to those skilled in the art (Wilkens 2015). These transporters are primary active transporters depending on ATP hydrolysis, organised in two nucleotide-binding domains (NBD) and in two transmembrane domains (TMD). The *Yarrowia lipolytica* endogenous transporter YALIOE25201 according to SEQ ID NO: 3 is an example of ABC transporter.

All transport proteins are characterized by multiple (i.e. at least two, typically more than two) transmembrane domains with α-helical secondary structure. Therefore in one embodiment the parent polypeptide or the variant polypeptide, when expressed in a recombinant host cell, has multiple transmembrane domains with α-helical secondary structure.

Typically, the parent polypeptide or the variant polypeptide according to the disclosure may be a steviol glycoside transport protein, typically a transport protein selected from an ATP-Binding Cassettes (ABC) transporter, a Major Facilitator Superfamily (MFS) transporter, a Small Multidrug Resistance (SMR) transporter, a transporter belonging to the Resistance-Nodulation-Cell division (RND) family, a Multi-Antimicrobial-Extrusion Protein.

The variant polypeptide and optionally the parent polypeptide according to the disclosure has steviol glycoside transport mediating activity across the membrane of a recombinant cell.

The parent polypeptide may be native, in the sense that it is naturally found in, obtained from or can be isolated from a cell, e.g. the recombinant cell as disclosed hereafter. Alternatively the parent polypeptide can be heterologous to the recombinant cell. The term "heterologous" as used herein refers to nucleic acid or amino acid sequences not naturally occurring in a cell. In other words, the nucleic acid or amino acid sequence is not identical to that naturally found in the host cell.

In yet another embodiment the parent polypeptide may be a transporter protein template or closest homologue that can be found via BLAST search in a public database such as Uniprot. For example the parent polypeptide may be a consensus sequence designed from a multiple sequence alignment. Methods to perform multiple sequence alignments are known in the art and are defined herein.

As used herein, the terms "variant, or "mutant" can be used interchangeably. They can refer to either polypeptides or nucleic acids. Variants include substitutions, insertions, deletions, truncations, transversions, and/or inversions, at one or more locations relative to a parent sequence. Variants can be made for example by site-saturation mutagenesis, scanning mutagenesis, insertional mutagenesis, random mutagenesis, site-directed mutagenesis, and directed-evolution, as well as various other recombination or synthetic approaches. Variant polypeptides may differ from a parent polypeptide by a small number of amino acid residues and may be defined by their level of primary amino acid sequence homology/identity with a reference polypeptide, for example the parent polypeptide. Preferably, variant polypeptides have at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a reference polypeptide, e.g. a parent polypeptide. Methods for determining percent identity are known in the art and described herein. Generally, the variants retain the characteristic nature of the parent polypeptide, but have altered properties in some specific aspects.

With regard to nucleic acids, the terms refer to a nucleic acid that encodes a variant polypeptide, that has a specified degree of homology/identity with a reference nucleic acid, or that hybridizes under stringent conditions to a reference nucleic acid or the complement thereof. Preferably, a variant nucleic acid has at least 50%, at least 60%, at least 70%, at least 75%, at least 80%, at least 85%, at least 90%, at least 91%, at least 92%, at least 93%, s at least 94%, at least 95%, at least 96%, at least 97%, at least 98%, or even at least 99% nucleic acid sequence identity with a reference nucleic acid. Methods for determining percent identity are known in the art and described herein.

According to an embodiment of the first aspect the variant comprises an amino acid sequence which, when aligned with the amino acid sequence of the parent polypeptide (or of any reference polypeptide, e.g. the polypeptide according to the amino acid sequence of SEQ ID NO: 3), comprises at least one modification of an amino acid residue corresponding to any of the amino acids in the amino acid sequence of the parent polypeptide.

The wording "Amino acid sequence aligned with the amino acid sequence set out in the sequence of the parent polypeptide" (or aligned with the amino acid sequence set out in the sequence of the reference polypeptide, e.g. the polypeptide according to the amino acid sequence of SEQ ID NO: 3) means that the variant amino acid sequence and the amino acid sequence of the parent polypeptide (or e.g. set out in SEQ ID NO: 3) are aligned by a suitable method which allows a) comparison of the sequences with each other and b) identification of the positions in the amino acid sequence of the variant wherein either the same amino acid is present (identical position), or another amino acid is present (substitution), or one or more extra amino acids are present (insertion or extension) or no amino acid is present (deletion or truncation) if compared with the amino acid sequence of the parent polypeptide or reference polypeptide (e.g. the one set out in SEQ ID NO: 3). Therefore a modification in the context of the disclosure is either a substitution, an addition or a deletion, of an amino acid residue corresponding to any of amino acids present in the parent polypeptide or a reference polypeptide when aligned with a suitable method. A suitable method allowing comparison of two amino acid sequences may be any suitable Pairwise Sequence Alignment method known to those skilled in the art, preferably a Global Pairwise Sequence Alignment method. A preferred Global Pairwise Sequence Alignment method is the EMBOSS Needle method based on the Needleman-Wunsch alignment algorithm (aiming at finding the optimum alignment (including gaps) of the two sequences along their entire length) (Needleman, S. B. and Wunsch, C. D. (1970) J. Mol. Biol. 48, 443-453) as described herein. In one embodiment the amino acid sequence is aligned with the amino acid sequence of the parent polypeptide or of a reference polypeptide (as e.g. set out in SEQ ID NO: 3) using the NEEDLE program from the EMBOSS package, using EBLOSUM62 as a substitution matrix, with a gap-open penalty of 10 and a gap extension penalty of 0.5.

It has been surprisingly found that the variant polypeptide according to the first aspect of the disclosure has an improved ability to mediate transport of rebaudioside M outside the cell when compared to other steviol glycosides. This ability can be measured by measuring the ratio between the molar concentration of rebaudioside M and the molar concentration of other steviol glycosides (e.g. of rebaudioside A or of total steviol glycosides) produced by a recombinant cell expressing the variant and comparing it with the ratio between the molar concentration of rebaudioside M and the molar concentration of other steviol glycosides (e.g. of rebaudioside A or of total steviol glycosides) produced by a recombinant cell expressing the parent polypeptide, when measured under the same conditions. Preferably in the recombinant cells according to the present disclosure the ratio between the molar concentration of rebaudioside M and the molar concentration of other steviol glycosides (e.g. of rebaudioside A or of total steviol glycosides) produced by a recombinant cell expressing the variant is higher than the ratio between the molar concentration of rebaudioside M and the molar concentration of other steviol glycosides (e.g. of rebaudioside A or of total steviol glycosides) produced by a recombinant cell expressing the parent polypeptide, when measured under the same conditions.

In the context of the present specification the wording "produced by a recombinant cell" when referring to rebaudioside M or rebaudioside A or total steviol glycosides means rebaudioside M or rebaudioside A or total steviol glycosides found in the fermentation broth after opening up the cells to release the cell content and optionally after removing undissolved cellular material such as the cell walls.

Preferably in the recombinant cells according to the present disclosure the ratio between the molar concentration of rebaudioside M and the molar concentration of other steviol glycosides (e.g. of rebaudioside A or of total steviol glycosides) produced extracellurlay by a recombinant cell expressing the variant is higher than the ratio between the molar concentration of rebaudioside M and the molar concentration of other steviol glycosides (e.g. of rebaudioside A or of total steviol glycosides) produced extracellularly by a recombinant cell expressing the parent polypeptide, when measured under the same conditions.

In the context of the present specification the wording "produced extracellularly by a recombinant cell" means the rebaudioside M (or rebaudioside A or total steviol glycosides) found in the fermentation broth after removing the intact cells, i.e. without releasing the cell content in the fermentation broth prior to removal.

Within the context of the present disclosure "measured under the same conditions" or "analysed under the same conditions" means that the variant polypeptide and the parent polypeptide are expressed in a recombinant cell in the same way and in the same type of cell, that the recombinant cell expressing the variant and that expressing the parent polypeptide are cultivated under the same conditions and that the amount (the molar concentration) of rebaudioside M and/or other steviol glycosides produced by the recombinant cell expressing the variant and those produced by the recombinant cell expressing the parent polypeptide are measured, respectively, using the same conditions, preferably by using the same assay and/or methodology, more preferably within the same experiment.

Typically the variant polypeptide and the parent polypeptide are expressed in a recombinant cell in the same way when the variant polypeptide or the parent polypeptide are expressed in a recombinant cell using the same type of expression cassette, i.e. an expression cassette wherein the polynucleotide coding for the variant or the polynucleotide coding for the parent polypeptide are linked to the same type of control sequences and in the same fashion, preferably in the same copy number, wherein the expression cassette is preferably integrated in the recombinant cell in the same locus of the genome.

The same type of cell in the context of this disclosure means a cell of the same genus, the same species and with the same genetic background.

In order to determine the concentration (e.g. the molar concentration) of steviol glycoside, e.g. or rebaudioside M and/or of rebaudioside A and/or of total steviol glycosides produced by a recombinant cell expressing the variant polypeptide or the parent polypeptide methods known to those skilled in the art may be used. In one embodiment the assay for measuring steviol glycosides is the one described in the examples.

In one embodiment the concentration (such as molar concentration) of steviol glycoside produced extracellularly by a recombinant host cell expressing the variant or expressing the parent polypeptide can be measured according to the following protocol:
 a) grow the cell for a fixed period of time in a suitable nutrient medium under conditions which allow the recombinant cell to grow and to produce steviol glycosides, preferably under conditions wherein steviol glycosides are soluble;
 b) recover the steviol glycosides produced extracellularly and measure the molar concentration of steviol glycosides.

In another embodiment the (molar) concentration of steviol glycoside produced by s a recombinant cell expressing the variant or expressing the parent polypeptide can be measured according to the following protocol:
 a) grow the cell for a fixed period of time in a suitable nutrient medium under conditions which allow the recombinant cell to grow and to produce steviol glycosides;
 b) recover the steviol glycosides produced by the cell and measure the molar concentration of steviol glycosides.

To grow the cell for a fixed period of time in a suitable nutrient medium under conditions which allow the recombinant cell to grow and to produce steviol glycosides, suitable growth conditions for said hosts should to be applied. These have been described for organism mentioned above, and should be known to those skilled in the art.

Growth and/or production medium should allow the organism to reach a certain biomass concentration, such that quantifiable amounts of product can be determined. The nutrient medium should also allow the expression of genes needed for the production of steviol glycosides. The suitable medium may differ depending on the recombinant cell. Examples of suitable media are disclosed.

Typically for screening purposes, shake flasks, culture plates or micro titer plates (MTP) are being used. Other systems may be used, e.g. beads, droplets, fermenters, etc. For organisms requiring oxygen, the growth vessel needs to be suitable for aerobic or micro-aerobic fermentations. Growth vessels such as shake flasks or MTPs are typically agitated to allow the transfer of gasses (e.g. oxygen, carbon dioxide) between the liquid and the gas phase. Stirring may also be used. Fermenters may be sparged with air or other gas mixtures, possibly in combination with agitation by impellors.

Preferably, the medium should be designed such that high viscosity is avoided, to allow sufficient mixing and gas transfer. Very high concentrations or amounts of substrates (e.g. containing glucose, sucrose, ethanol, glycerol, oil, starch) may lead to very high concentration of biomass, which may negatively affect mixing, gas transfer and dissolved oxygen. This is further dependent on the efficiency of the strain for the production of the steviol glycoside (the yield of product on substrate) under that condition. When designing an appropriate medium this should be taken into account. For purposes of evaluating the extracellular production, conditions should be used that do not exceed solubility limits of the product in the broth. The extracellular concentration may then be determined by separating the cells from the liquid phase, e.g. by centrifugation or filtration, and determining the concentration of steviol glycosides in the supernatant or filtrate.

To recover steviol glycosides produced extracellularly the following procedure can be followed:
 after growth, a determined aliquot of cell culture is centrifuged at 1500 g for 10 minutes; after centrifugation supernatant is transferred and diluted in 33% acetonitrile and the steviol glycoside concentrations are determined, e.g. according to methods known in the art, e.g. using Liquid Chromatography with Mass Spectrometer (LC-MS) or using Liquid Chromatography with UV (LC-UV).

To recover steviol glycosides produced by the cell the following procedure can be followed: after growth a determined aliquot of cell culture is homogenized and treated for 10 minutes at 90° C. and allowed to cool down to room temperature, diluted with acetonitrile up to a concentration of 33% acetonitrile, mixed, centrifuged at 1500 g for 10 minutes and of the resulting supernatant the steviol glycoside concentrations are determined, e.g. according to methods known in the art, e.g. using LC-MS or LC-UV.

To determine the molar concentration of steviol glycosides by LC-MS, Ultra Performance Liquid Chromatography with Mass Spectrometry system (UPLC-MS) may be used, e.g. using UPLC equipped with a reverse phase C18 column A suitable type of mass spectrometer may be a triple quadrupole mass spectrometer (TQ MS).

Steviol glycosides concentrations may be determined using a UPLC coupled to a TQ Mass Spectrometer equipped with an electrospray ionization source operated in the negative-ion mode in MRM mode at the deprotonated molecules [M-H]$^-$ for all steviol glycosides studied, except for Rebaudioside A and rubusoside, which are monitored at [M-H-hexose].

The steviol glycosides to be analysed and quantified may be separated using a 2.1×100 mm, with 1.8 μm particle size, silica based, $C_{18}$ reverse-phase column, (e.g. a Acquity UPLC® HSS T3 column or alternative column having the same characteristics), using a gradient elution with (A) 50 mM ammonium acetate in LC-MS grade water, and (B) LC-MS grade acetonitrile, using the following gradient: from 30% to 35% B in 0.5 minutes, keep at 35% B for 0.8 minutes, from 35% B to 95% B in 0.7 minutes, keep at 95% B for 0.5 minutes, re-equilibrating with 30% B for 1.5 mM, using a flow rate of 0.6 ml/min, using an injection volume of 5 μl and a column temperature of 50° C., quantifying the steviol glycosides using an external calibration line of the components in the range of 10-600 ng/ml, wherein the corresponding analyzed samples are diluted so that the concentration of the desired components fall in the linear range of calibration line; wherein the concentration of acetonitrile in the sample is 33%; wherein the concentration of the components in the samples are calculated using the TargetLynx software (Waters) using a quadratic calibration line whereby the origin is forced through zero and the weighting function 1/x is used. LC or UPLC gradients indicated herein are expressed as volume percentage, i.e. % v/v, Validated references may be used for Rebaudioside A, Rebaudioside B, Rebaudioside D, stevioside, steviolbioside, rubusoside, Rebaudioside M and steviol-13-monoside.

Steviol glycosides may also be determined using a LC-UV method developed according to the Food Chemical Codex (FCC) method in order to quantify the Rebaudioside A and other steviol glycosides (Rebaudioside M, Rebaudioside B, Rebaudioside D, stevioside, steviolbioside, rubusoside). Steviol glycosides may be analysed using a UPLC (e.g. as provided by Waters) coupled to a Photo Diode Array Detector (PDA detector) (e.g. as provided by Waters). The steviol glycosides to be analysed and quantified are separated using a 4.6×150 mm with 3 μm particle size silica based, reversed phase difunctionally bonded $C_{18}$ ($dC_{18}$) column (for example $dC_{18}$ Waters Atlantis or alternative column having the same characteristics) and detection at 210 nm, using an elution gradient with (A) 25% acetonitrile+ 0.00166% acetic acid in purified water, and B) LC-MS grade acetonitrile as mobile phases, using the following gradient: 0% B (=100% A) for 2 minutes, 0% B to 46% B in 11 minutes, 46% B to 98% B in 0.1 minutes, keep at 98% B for 4 minutes, from 98% B to 0% B in 0.1 minutes, re-equilibrating the column at 100% A for 5 minutes, using a flow rate at 1 ml/min, using an injection volume of 10 μl and a column temperature at 50° C., quantifying the desired components using an external calibration line of the components in the range of 2-100 μg/ml, wherein the corresponding samples analyzed are diluted accordingly so the concentration of the desired components is in the linear range of calibration line; wherein the concentration of acetonitrile in the sample is 25%.

Validated references may be used for Rebaudioside A, Rebaudioside B, Rebaudioside D, stevioside, steviolbioside, rubusoside, Rebaudioside M and steviol-13-monoside.

In one embodiment in the variant of a parent polypeptide according to the disclosure the ratio between the molar concentration of rebaudioside M produced by a recombinant cell expressing the variant and the molar concentration of rebaudioside M produced by a recombinant cell expressing the parent polypeptide is at least 0.1, 0.3, 0.5, preferably at least 0.8, more preferably at least 1 when measured under the same conditions. More s preferably said ratio is higher than 1, such as for example at least 1.1, 1.2, 1.5, or at least 2, 2.5, 3, 3.5, 4, 5, 6, 7, 8, 9, or at least 10, 20, 30, 50, 100, 1000 or more when measured under the same conditions.

In one embodiment in the variant of a parent polypeptide according to the disclosure the ratio between the molar concentration of rebaudioside M produced extracellularly by a recombinant cell expressing the variant and the molar concentration of rebaudioside M produced extracellularly by a recombinant cell expressing the parent polypeptide is at least 0.1, 0.3, 0.5, preferably at least 0.8, more preferably at least 1 when measured under the same conditions. More preferably said ratio is higher than 1, such as for example at least 1.1, 1.2, 1.5, or at least 2, 2.5, 3, 3.5, 4, 5, 6, 7, 8, 9, or at least 10, 20, 30, 50, 100, 1000 or more when measured under the same conditions.

In one embodiment in the variant of a parent polypeptide according to the disclosure the ratio between the molar concentration of rebaudioside M and the molar concentration of rebaudioside A produced by a recombinant cell expressing the variant is higher than the ratio between the molar concentration of rebaudioside M and the molar concentration of rebaudioside A produced by a recombinant cell expressing the parent polypeptide, when measured under the same conditions. Preferably said ratio between the molar concentration of rebaudioside M and the molar concentration of rebaudioside A produced by a recombinant cell expressing the variant is at least 1.1 times or at least 1.2, 1.5, times or at least 2, 2.5, 3, 3.5, 4, 5, 6, 7, 8, 9 times or at least 10, 20, 30, 50, 100, 1000 or more times the ratio between the molar concentration of rebaudioside M and the molar concentration of rebaudioside A produced by a recombinant cell expressing the parent polypeptide, when measured under the same conditions.

In one embodiment in the variant of a parent polypeptide according to the disclosure the ratio between the molar concentration of rebaudioside M and the molar concentration of rebaudioside A produced extracellularly by a recombinant cell expressing the variant is higher than the ratio between the molar concentration of rebaudioside M and the molar concentration of rebaudioside A produced extracellularly by a recombinant cell expressing the parent polypeptide, when measured under the same conditions. Preferably said ratio between the molar concentration of rebaudioside M and the molar concentration of rebaudioside A produced extracellularly by a recombinant cell expressing the variant is at least 1.1 times or at least 1.2, 1.5, times or at least 2, 2.5, 3, 3.5, 4, 5, 6, 7, 8, 9 times or at least 10, 20, 30, 50, 100, 1000 or more times the ratio between the molar concentration of rebaudioside M and the molar concentration of rebaudioside A produced extracellularly by a recombinant cell expressing the parent polypeptide, when measured under the same conditions.

In one embodiment in the variant of a parent polypeptide according to the disclosure the ratio between the molar concentration of rebaudioside M and the molar concentration of total steviol glycosides produced by a recombinant cell expressing the variant is higher than the ratio between the molar concentration of rebaudioside M and the molar concentration of total steviol glycosides produced by a recombinant cell expressing the parent polypeptide when measured under the same conditions. Preferably said ratio between the molar concentration of rebaudioside M and the molar concentration of total steviol glycosides produced by a recombinant cell expressing the variant is at least 1.1 times or at least 1.2, 1.5, times or at least 2, 2.5, 3, 3.5, 4, 5, 6, 7, 8, 9 times or at least 10, 20, 30, 50, 100, 1000 or more times the ratio between the molar concentration of rebaudioside M and the molar concentration of total steviol glycosides produced by a recombinant cell expressing the parent polypeptide when measured under the same conditions. In the context of the disclosure total steviol glycosides includes Rebaudioside A, Rebaudioside B, Rebaudioside D, Rebaudioside M, stevioside, steviolbioside, rubusoside, and steviol-13-monoside.

In one embodiment in the variant of a parent polypeptide according to the disclosure the ratio between the molar concentration of rebaudioside M and the molar concentration of total steviol glycosides produced extracellularly by a recombinant cell expressing the variant is higher than the ratio between the molar concentration of rebaudioside M and the molar concentration of total steviol glycosides produced extracellularly by a recombinant cell expressing the parent polypeptide when measured under the same conditions. Preferably said ratio between the molar concentration of rebaudioside M and the molar concentration of total steviol glycosides produced extracellularly by a recombinant cell expressing the variant is at least 1.1 times or at least 1.2, 1.5, times or at least 2, 2.5, 3, 3.5, 4, 5, 6, 7, 8, 9 times or at least 10, 20, 30, 50, 100, 1000 or more times the ratio between the molar concentration of rebaudioside M and the molar concentration of total steviol glycosides produced extracellularly by a recombinant cell expressing the parent polypeptide when measured under the same conditions. In the context of the disclosure total steviol glycosides includes Rebaudioside A, Rebaudioside B, Rebaudioside D, Rebaudioside M, stevioside, steviolbioside, rubusoside, and steviol-13-monoside.

In the context of the disclosure the wording "total steviol glycosides" refers to the total of steviol glycosides produced by the recombinant cell including but not limited to rebaudioside M, rebaudioside A, rebaudioside B, rebaudioside D, stevioside, steviolbioside, rubusoside, and steviol-13-monoside. In one embodiment the molar concentration of total steviol glycosides refers to the sum of the molar concentrations of rebaudioside M, rebaudioside A, rebaudioside B, rebaudioside D, stevioside, steviolbioside, rubusoside, and steviol-13-monoside.

In one embodiment the variant of a parent polypeptide wherein the variant has steviol glycoside transport mediating activity is a variant comprising an amino acid sequence which, when aligned with the amino acid sequence set out in SEQ ID NO: 3, comprises at least one modification of an amino acid residue corresponding to any of amino acids in the amino acid sequence according to SEQ ID NO: 3, wherein, when measured under the same conditions:
  a) the ratio between the molar concentration of rebaudioside M produced by a recombinant cell expressing the variant and the molar concentration of rebaudioside M produced by a reference cell is at least 0.1; and/or
  b) the ratio between the molar concentration of rebaudioside M and the molar concentration of rebaudioside A produced by a recombinant cell expressing the variant is higher than the ratio between the molar concentration of rebaudioside M and the molar concentration of rebaudioside A produced by a reference cell; and/or
  c) the ratio between the molar concentration of rebaudioside M and the molar concentration of total steviol glycosides produced by a recombinant cell expressing the variant is higher than the ratio between the molar concentration of rebaudioside M and the molar concentration of total steviol glycosides produced by a reference cell;
wherein a reference cell is a recombinant cell expressing the parent polypeptide. In one embodiment of the first aspect the modification of the amino acid sequence in the variant occurs in a portion of the sequence which, when expressed in a recombinant cell, corresponds to a helical transmembrane region.

In one embodiment the variant comprises an amino acid sequence which, when aligned with the amino acid sequence set out in SEQ ID NO: 3, comprises at least one modification of an amino acid residue corresponding to any of amino acids 14-67; 135-156; 159-160; 199-215; 255-258; 262-284; 291-312; 314-328; 375-390; 407-429; 852-869; 890-908; 958-980; 986-1014; 1012-1021; 1059-1062; 1067-1080; 1104-1125; 1127-1128; in the amino acid sequence according to SEQ ID NO: 3, said positions being defined with reference to the amino acid sequence set out in SEQ ID NO: 3.

In one embodiment the disclosure provides a variant of a parent polypeptide wherein the variant has steviol glycoside transport mediating activity, optionally a variant as described herein before, wherein the variant comprises an amino acid sequence which, when aligned with the amino acid sequence set out in SEQ ID NO: 3, comprises at least one modification of an amino acid residue corresponding to any of amino acids,
   15, 19, 26, 29, 31, 32, 33, 37, 46, 56, 59, 107, 135, 136, 141, 145, 148, 150, 151, 153, 199, 200, 204, 206, 207, 210, 211, 255, 257, 258, 262, 267, 268, 272, 273, 276, 277, 278, 281, 282, 283, 284, 292, 294, 296, 297, 298, 299, 300, 302, 303, 306, 307, 309, 310, 311, 315, 318, 319, 320, 321, 322, 323, 324, 326, 328, 375, 376, 378, 379, 380, 382, 384, 386, 387, 389, 408, 410, 411, 413, 414, 415, 416, 417, 419, 420, 421, 422, 423, 424, 425, 427, 428, 429, 853, 854, 857, 859, 862, 864, 869, 890, 891, 892, 894, 903, 906, 968, 969, 972, 974, 977, 986, 996, 998, 999, 1001, 1003, 1004, 1010, 1012, 1016, 1017, 1018, 1019, 1020, 1021, 1059, 1060, 1061, 1062, 1063, 1075, 1076, 1107, 1108, 1111, 1112, 1115, 1118, 1120, 1123, 1127, 1128, 1179, 1200,
   said positions being defined with reference to the amino acid sequence set out in SEQ ID NO: 3.

In one embodiment the modification in the amino acid sequence of the variant is a substitution, an addition or a deletion.

In one embodiment the variant according to the present disclosure comprises an amino acid sequence which, when aligned with the amino acid sequence set out in SEQ ID NO: 3, comprises one or more of
   A or V at position 15, G at position 19, Q or W at position 26, F at position 29, Y or A at position 31, N at position 32, I at position 33, G at position 37, T at position 46, T at position 56, L at position 59, R at position 107, C at position 135, Y at position 136, K at position 141, I at position 145, Q at position 148, L at position 150, G at position 151, L or P at position 153, T at position 199, Y at position 200, F at position 204, I at position 206, W at position 207, G or V at position 210, L at position 211, A at position 255, C or L at position 257, N or Q or S at position 258, F or I at position 262, G or L at position 267, Q or S or T at position 268, G at position 272, Y at position 273, G at position 276, S at position 277, V at position 278, N at position 281, N at position 282, F at position 283, G or S at position 284, T at position 292, T at position 294, T at position 296, S at position 297, K or L at position 298, L or T or V at position 299, M at position 300, F or Q or S or T or V at position 302, M or R or T at position 303, F or I or M or S at position 306, I or L at position 307, M at position 309, C or N at position 310, T or W at position 311, A at position 315, K at position 318, K at position 319, A at position 320, N at position 321, A s or E or L or V at position 322, W at position 323, A at position 324, E at position 326, E at position 328, F or K or H or L or N at position 375, W at position 376, I or N or T or V at position 378, Y at position 379, E or R at position 380, G or S or T or W at position 382, G or N or S or T at position 384, I or L at position 386, A at position 387, M at position 389, G at position 408, A at position 410, F or G at position 411, I at position 413, F or G or R at position 414, V at position 415, W at position 416, A or S or T or W at position 417, G or M at position 419, G or S at position 420, F or I at position 421, M at position 422, A or Q at position 423, L or S at position 424, A or H or L or M or V at position 425, M at position 427, M at position 428, M or S at position 429, V at position 853, G or S at position 854, P at position 857, A or P or S at position 859, T at position 862, A at position 864, V at position 869, P at position 890, T at position 891, F or V at position 892, Q or Y at position 894, N at position 903, V at position 906, Q at position 968, N at position 969, Q at position 972, Q at position 974, A or Q at position 977, H at position 986, Y at position 996, A or G at position 998, N or T at position 999, Y at position 1001, I at position 1003, T at position 1004, T at position 1010, L at position 1012, E at position 1016, A at position 1017, L or V at position 1018, G at position 1019, A at position 1020, A or N or W at position 1021, E at position 1059, T at position 1060, G at position 1061, L at position 1062, I at position 1063, S or L at position 1075, A or G at position 1076, Y at position 1107, K or Q at position 1108, K at position 1111, N at position 1112, G at position 1115, A or F or W at position 1118, M at position 1120, P at position 1123, A or N at position 1127, D at position 1128, N at position 1179, I at position 1200, said positions being defined with reference to the amino acid sequence set out in SEQ ID NO: 3.

In a preferred embodiment the variant according to the first aspect comprises an amino acid sequence which, when aligned with the amino acid sequence set out in SEQ ID NO: 3, comprises at least two modifications of an amino acid residue corresponding to any of amino acids in the amino acid sequence according to SEQ ID NO: 3 or with the parent polypeptide or with another reference polypeptide, wherein, when measured under the same conditions:

a) the ratio between the molar concentration of rebaudioside M produced by a recombinant cell expressing the variant and the molar concentration of rebaudioside M produced by a reference cell is at least 1.2; and/or b) the ratio between the molar concentration of rebaudioside M and the molar concentration of rebaudioside A produced by a recombinant cell expressing the variant is at least 1.2 times the ratio between the molar concentration of rebaudioside M and the molar concentration of rebaudioside A produced by a reference cell; and/or c) the ratio between the molar concentration of rebaudioside M and the molar concentration of total steviol glycosides produced by a recombinant cell expressing the variant is at least 1.2 times the ratio between the molar concentration of rebaudioside M and the molar concentration of total steviol glycosides produced by a reference cell;

wherein the at least two modifications are a substitution of an amino acid residue corresponding to any of amino acids 322, 375, 376, 378, 382, 384, 386, 420, 421, 424, 425, 429, 890, 891, 969, 977, 1060, 1107, 1111, 1112, 1115, 1118, 1120, 1179, said positions being defined with reference to the amino acid sequence set out in SEQ ID NO: 3, wherein a reference cell is a recombinant cell expressing the parent polypeptide.

Preferably the variant comprises an amino acid sequence which, when aligned with the amino acid sequence set out in SEQ ID NO: 3, comprises one or more of A or E or L or V at position 322, F or K or H or L or N at position 375, W at position 376, I or N or T or V at position 378, G or S or T or W at position 382, G or N or S or T at position 384, I or L at position 386, G or S at position 420, F or I at position 421, L or S at position 424, A or H or L or M or V at position 425, M or S at position 429, P at position 890, T at position 891, N at position 969, A or Q at position 977, T at position 1060, Y at position 1107, K at position 1111, N at position 1112, G at position 1115, A or F or W at position 1118, Mat position 1120, N at position 1179, said positions being defined with reference to the amino acid sequence set out in SEQ ID NO: 3.

In one embodiment the variant according to the first aspect comprises an amino acid sequence which, when aligned with the amino acid sequence set out in SEQ ID NO: 3 or with the parent polypeptide or with another reference polypeptide, comprises a combination of modifications as indicated in the Embodiments of the disclosure herein (embodiment 12).

In one embodiment of the first aspect the parent polypeptide has at least 10%, at least 20% at least 30%, at least 40%, at least 50% sequence identity with the amino acid s sequence set out in SEQ ID NO: 3. Preferably, the parent polypeptide has at least 60%, at least 70%, at least 75%, at least 80%, at least 85%, at least 90%, at least 91%, at least 92%, at least 93%, at least 94%, at least 95%, at least 96%, at least 97%, at least 98%, or even at least 99% sequence identity with the amino acid sequence set out in SEQ ID NO: 3. In an embodiment the parent polypeptide comprises the amino acid sequence set out in SEQ ID NO: 3. In yet another embodiment of the first aspect the variant polypeptide has at least 10%, at least 20% at least 30%, at least 40%, at least 50% sequence identity with the amino acid sequence of the parent polypeptide, e.g. with the amino acid sequence set out in SEQ ID NO: 3. Preferably, variant polypeptides have at least 60%, at least 70%, at least 75%, at least 80%, at least 85%, at least 90%, at least 91%, at least 92%, at least 93%, at least 94%, at least 95%, at least 96%, at least 97%, at least 98%, or even at least 99% sequence identity with the amino acid sequence of the parent polypeptide.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this disclosure the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the disclosure is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present disclosure can further be used as a "query sequence" to perform a search against public databases to, for example, identify other family members or related sequences. Such searches can be performed using the BLASTN and BLASTX programs (version 2.0) of Altschul, et al. (1990) J. Mol. Biol. 215:403-10. BLAST nucleotide searches can be performed with the BLASTN program, score=100, wordlength=12 to obtain nucleotide sequences homologous to nucleic acid molecules of the disclosure. BLAST protein searches can be performed with the BLASTX program, score=50, wordlength=3 to obtain amino acid sequences homologous to protein molecules of the disclosure. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTX and BLASTN) can be used. See the homepage of the National Center for Biotechnology Information at www.ncbi.nlm.nih.gov/.

Methods to Produce Variant Polypeptides

In a second aspect the disclosure provides a method to produce a variant polypeptide according to the disclosure comprising:
  a) providing a parent polypeptide, optionally wherein the parent polypeptide has steviol glycoside transport mediating activity;
  b) modifying in the parent polypeptide sequence at least one amino acid residue to yield a variant polypeptide sequence, optionally wherein the modification in the parent polypeptide sequence occurs in a portion of a sequence which correspond to a helical transmembrane region; and optionally
  c) selecting a variant polypeptide which when expressed in a recombinant cell has steviol glycoside transport mediating activity and has the following characteristics:
    i) the ratio between the molar concentration of rebaudioside M produced by a recombinant cell expressing the variant and the molar concentration of rebaudioside M produced by a reference cell is at least 0.1; and/or
    ii) the ratio between the molar concentration of rebaudioside M and the molar concentration of rebaudioside A produced by a recombinant cell expressing the variant is higher than the ratio between the molar concentration of rebaudioside M and the molar concentration of rebaudioside A produced by a reference cell; and/or
    iii) the ratio between the molar concentration of rebaudioside M and the molar concentration of total steviol glycosides produced by a recombinant cell expressing the variant is higher than the ratio between the molar concentration of rebaudioside M and the molar concentration of total steviol glycosides produced by a reference cell;
  wherein a reference cell is a recombinant cell expressing the parent polypeptide, optionally wherein the molar concentration of rebaudioside M, rebaudioside A and total steviol glycosides in the ratio's according to i), ii), and iii) is the molar concentration produced extracellularly.

Step a) of the method according to the second aspect comprises providing a parent polypeptide. The parent polypeptide is typically one as defined herein before. Typically the parent polypeptide that is used as template in the method of the second aspect has the ability to mediate steviol glycoside transport across the cell membrane, at least in some extent. Preferably the parent polypeptide is a transport protein as defined herein before. In one embodiment the parent polypeptide is an ABC transporter as defined herein before.

Step b) of the method according to the second aspect comprises modifying in the parent polypeptide sequence at least one amino acid residue to yield a variant polypeptide sequence. In one embodiment of the second aspect the modification of the amino acid sequence in the variant occurs in a portion of the sequence which, when expressed in a recombinant cell, corresponds to a helical transmembrane region. In one embodiment mutations may be introduced preferably in trans-membrane regions, and, in case of engineering ABC transporters, preferably in trans-membrane regions and optionally in positions between the membrane spanning domain and the ATP binding cassette domains.

In one embodiment step b) comprises modifying in the parent polypeptide sequence at least one amino acid residue to yield a variant polypeptide sequence, preferably comprises identifying in the parent polypeptide one or more amino acid residues to be modified and modifying in the parent polypeptide sequence at least one amino acid residue to yield a variant polypeptide sequence. In order to identify promising positions wherein a modification can be introduced, a model of the parent polypeptide comprising its secondary, tertiary and/or quaternary structure may be used, preferably a model of the structure assumed by the parent polypeptide in a biological membrane. For example, a crystal structure of the membrane transport protein may be used. Where no crystal structure is available, a homology modelling program such as Yasara or SWISS-MODEL may be used. SWISS-MODEL is a fully automated protein structure homology-modelling server, accessible via the ExPASy web server, or from the program DeepView (Swiss Pdb-Viewer), accessible for example at swissmodel.expasy.org/. Yasara is available at www.yasara.org/homologymodeling.htm. Where no crystal structure or suitable structural homology model can be used to assign promising positions e.g. in the trans membrane regions that are involved in steviol glycoside binding and or target molecule specificity, it is for example possible to estimate trans membrane regions by multiple sequence analysis that include protein transporters for example ABC transporters, with known structures and/or by running a trans membrane prediction program such as TMHMM (www.cbs.dtu.dk/services/TMHMM/) (Krogh et al. 2001; Sonnhammer et al. 1998). In case promising positions in said regions cannot be reliably predicted it is possible to scan a larger number of positions e.g. with single site saturation mutagenesis, partial saturation mutagenesis or by doing an alanine scan to find hot spot positions for transporter specificity and/or selectivity engineering for steviol glycoside compounds in the first engineering round. In a subsequent round of mutagenesis and screening transporter performance can be further improved e.g. by combinatorial mutagenesis of hot-spot positions that were preidentified, by exploring more amino acid diversity at hot-spot positions in case not full amino acid diversity was covered in the previous round or by combination of two or more hot spot positions. Once the promising positions for modifications have been identified, the amino acids in these positions are modified, e.g. substituted with other amino acids, or amino acids are deleted from or added to the polypeptide sequence, preferably substituted with other amino acids which are expected to positively improve the ability of the variant to transport steviol glycosides, such as rebaudioside M across the membrane. Once the polypeptide sequence of the variant has been established the polypeptide variant can be synthesised according to methods known to those skilled in the art and expressed in a recombinant cell according to methods known to the skilled person.

Step c) of the method according to the second aspect comprises selecting a variant polypeptide which when expressed in a recombinant cell has steviol glycoside transport mediating activity and has the following characteristics, when measured under s the same conditions:

i) the ratio between the molar concentration of rebaudioside M produced by a recombinant cell expressing the variant and the molar concentration of rebaudioside M produced by a reference cell is at least 0.1; and/or ii) the ratio between the molar concentration of rebaudioside M and the molar concentration of rebaudioside A produced by a recombinant cell expressing the variant is higher than the ratio between the molar concentration of rebaudioside M and the molar concentration of rebaudioside A produced by a reference cell; and/or iii) the ratio between the molar concentration of rebaudioside M and the molar concentration of total steviol glycosides produced by a recombinant cell expressing the variant is higher than the ratio between the molar concentration of rebaudioside M and the molar concentration of total steviol glycosides produced by a reference cell;

wherein a reference cell is a recombinant cell expressing the parent polypeptide, optionally wherein the molar concentration of rebaudioside M, rebaudioside A and total steviol glycosides in the ratio's according to i), ii), and iii) is the molar concentration produced extracellularly. The ratios mentioned in i., ii. and iii. can be determined as described in the first aspect of the invention and in the list of Embodiments of the disclosure (embodiments 15 to 18).

In one embodiment according to the second aspect modifying in the parent polypeptide sequence at least one amino acid residue to yield a variant polypeptide sequence in step b) comprises:

I) aligning the amino acid sequence of the parent polypeptide with the amino acid sequence set out in SEQ ID NO: 3, II) modifying, e.g. substituting, adding or deleting, one or more amino acid residues corresponding to any of amino acids, 15, 19, 26, 29, 31, 32, 33, 37, 46, 56, 59, 107, 135, 136, 141, 145, 148, 150, 151, 153, 199, 200, 204, 206, 207, 210, 211, 255, 257, 258, 262, 267, 268, 272, 273, 276, 277, 278, 281, 282, 283, 284, 292, 294, 296, 297, 298, 299, 300, 302, 303, 306, 307, 309, 310, 311, 315, 318, 319, 320, 321, 322, 323, 324, 326, 328, 375, 376, 378, 379, 380, 382, 384, 386, 387, 389, 408, 410, 411, 413, 414, 415, 416, 417, 419, 420, 421, 422, 423, 424, 425, 427, 428, 429, 853, 854, 857, 859, 862, 864, 869, 890, 891, 892, 894, 903, 906, 968, 969, 972, 974, 977, 986, 996, 998, 999, 1001, 1003, 1004, 1010, 1012, 1016, 1017, 1018, 1019, 1020, 1021, 1059, 1060, 1061, 1062, 1063, 1075, 1076, 1107, 1108, 1111, 1112, 1115, 1118, 1120, 1123, 1127, 1128, 1179, 1200, said positions being defined with reference to the amino acid sequence set out in SEQ ID NO: 3.

Preferred embodiments of the first aspect of the disclosure can also be applied to the second aspect of the disclosure.

The disclosure further relates to a nucleic acid sequence coding for a variant of a parent polypeptide as disclosed in the first aspect. The nucleic acid sequence coding for the variant polypeptide according to the disclosure may be an "isolated nucleic acid". An "isolated nucleic acid" or "isolated polynucleotide" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. Moreover, an "isolated nucleic acid fragment" is a nucleic acid fragment that is not naturally occurring as a fragment and would not be found in the natural state.

The disclosure further relates to a nucleic acid construct comprising the polynucleotide sequence coding for a variant polypeptide as disclosed herein.

The term "nucleic acid construct" is herein referred to as a nucleic acid molecule, either single- or double-stranded, which is derived from a naturally occurring gene or which has been modified to contain segments of nucleic acid which are combined and juxtaposed in a manner which would not otherwise exist in nature. Nucleic acid constructs can be isolated, synthetically made or mutagenized. The term nucleic acid construct is synonymous with the term "expression cassette" when the nucleic acid construct contains all the control sequences required for expression of a coding sequence, wherein said control sequences are operably linked to said coding sequence.

The nucleic acid construct as disclosed herein may be an expression cassette, wherein the nucleic acid coding for a variant polypeptide as disclosed herein is operably linked to at least one control sequence capable of directing the expression of a variant according to the first aspect in a suitable recombinant cell.

The term "expression" includes any step involved in the production of (a) polypeptide(s) including, but not limited to, transcription, post transcriptional modification, translation, post-translational modification, and secretion. The terms "increase of activity" or "overexpression" are used interchangeably herein.

An "expression cassette" comprises a nucleic acid coding for a polypeptide, operably linked to the appropriate control sequences which allow for expression of the nucleic acid in a cell or in vitro. Typically an expression cassette will comprises a polynucleotide coding for a polypeptide, operably linked to at least a promoter and a terminator sequence.

The expression cassette may be an autonomously replicating vector (e.g plasmid), i. e., a vector, the replication of which is independent of genome replication. Alternatively, the cassette may be one which, when introduced into the cell, is fully or partially integrated into the genome of the cell. In the latter cases it may comprise one or more targeting sequences to direct integration into the genome.

The expression cassette may or may not contain one or more selectable markers, which allow easy selection of transformed cells.

A "selectable marker" is a gene which allows for selection of cells transformed with such a gene and which provides for biocide or viral resistance, resistance to heavy metals, prototrophy to auxotrophs, and the like.

Preferred selectable markers include, but are not limited to, those which confer resistance to drugs or which complement a defect in the cell. They include e. g. versatile marker genes that can be used for transformation of most filamentous fungi and yeasts such as nucleic acid coding for acetamidase, or genes providing resistance to antibiotics. Alternatively, specific selection markers can be used such as auxotrophic markers which require corresponding mutant strains. Preferably, the selection marker is deleted from the transformed cell after introduction of the expression construct so as to obtain transformed cells which are free of selection marker genes.

The term selectable marker extends to a marker gene used for screening, i.e. marker gene that, once introduced into a cell confers to the cell a visible phenotype and causes the cell look different. An example of marker for screening is a gene coding for a fluorescent protein which causes cells to fluoresce under an appropriate light source. The term "control sequences" as used herein refers to components involved in the regulation of the expression of a coding sequence in a specific organism or in vitro. Examples of control sequences are transcription initiation sequences, termination sequences, promoters, leaders, signal peptides, propeptides, prepropeptides, or enhancer sequences; Shine-Delgarno sequences, s repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion.

The term "operably linked" as used herein refers to two or more components such as nucleic acid sequences or polypeptide sequences that are physically linked and are in a functional relationship with each other permitting them to function in their intended manner. For instance, a promoter is operably linked to a coding sequence if the promoter can regulate the transcription or expression of a coding sequence, in which case the coding sequence should be understood as being "under the control of" the promoter.

Recombinant Cells

In a third aspect the disclosure provides a recombinant cell capable of producing a steviol glycoside, wherein the cell comprises a nucleic acid coding for a variant of a parent polypeptide wherein the variant has steviol glycoside transport mediating activity, wherein the variant comprises an amino acid sequence which, when aligned with the amino acid sequence of the parent polypeptide, comprises at least one modification of an amino acid residue corresponding to any of the amino acids in the amino acid sequence of the parent polypeptide, wherein, when measured under the same conditions:

a) the ratio between the molar concentration of rebaudioside M produced by a recombinant cell expressing the variant and the molar concentration of rebaudioside M produced by a reference cell is at least 0.1; and/or b) the ratio between the molar concentration of rebaudioside M and the molar concentration of rebaudioside A produced by a recombinant cell expressing the variant is higher than the ratio between the molar concentration of rebaudioside M and the molar concentration of rebaudioside A produced by a reference cell; and/or c) the ratio between the molar concentration of rebaudioside M and the molar concentration of total steviol glycosides produced by a recombinant cell expressing the variant is higher than the ratio between the molar concentration of rebaudioside M and the molar concentration of total steviol glycosides produced by a reference cell;

wherein a reference cell is a recombinant cell expressing the parent polypeptide.

The term "recombinant" when used in reference to a nucleic acid, or protein indicates that the nucleic acid, or protein has been modified in its sequence if compared to its native form by human intervention. The term "recombinant" when referring to a cell indicates that the genome of the cell has been modified in its sequence if compared to its native form by human intervention. The term "recombinant" is synonymous with "genetically modified".

The variant polypeptide and the parent polypeptide used in cell of the third aspect are those described in the first aspect according to the disclosure and preferred embodiments of the first and second aspect of the disclosure are applicable to the third aspect as well.

The recombinant cell according to the third aspect comprises a polynucleotide coding for the variant polypeptide as disclosed herein or the nucleic acid construct as disclosed herein. The term "polynucleotide", "nucleic acid" are used interchangeably herein.

A nucleic acid construct or polynucleotide as disclosed herein can be introduced into a cell such as a prokaryotic or eukaryotic cell via conventional transformation or transfection techniques. As used herein, the terms "transformation" and "transfection" are intended to refer to a variety of art-recognized techniques for introducing foreign nucleic acid (e.g. DNA) into a recombinant cell well known to those skilled in the art. Suitable methods for transforming or transfecting recombinant cells can be found in Sambrook, et al. (Molecular Cloning: A Laboratory Manual, 2nd, ed. Cold Spring Harbor Laboratory, Cold Spring Harbor Laboratory Press, Cold Spring Harbor, NY, 1989), Davis et al., Basic Methods in Molecular Biology (1986) and other laboratory manuals.

A "cell" as defined herein is an organism suitable for genetic manipulation and which may be cultured at cell densities useful for industrial production of a target product. A suitable organism may be a microorganism, for example one which may be maintained in a fermentation device. With regard to the present disclosure, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code). A cell may be a cell found in nature or a cell derived from a parent cell after genetic manipulation or classical mutagenesis.

A cell as disclosed herein may be a prokaryotic, archaebacterial or eukaryotic cell.

A prokaryotic cell may, but is not limited to, a bacterial cell. Bacterial cell may be Gram negative or Gram positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus*), *Acinetobacter, Nocardia, Xanthobacter, Escherichia* (e.g., *E. coli*), *Streptomyces, Erwinia, Klebsiella, Serratia* (e.g., *S. marcescans*), *Pseudomonas* (e.g., *P. aeruginosa, P. fluorescens*), *Salmonella* (e.g., *S. typhimurium, S. typhi*), *Anabaena, Caulobactert, Gluconobacter, Rhodobacter, Paracoccus, Brevibacterium, Corynebacterium, Rhizobium* (*Sinorhizobium*), *Flavobacterium, Klebsiella, Enterobacter, Lactobacillus, Lactococcus, Methylobacterium, Staphylococcus*. Bacteria also include, but are not limited to, photosynthetic bacteria (e.g., green non-sulfur bacteria green sulfur bacteria purple sulfur bacteria and purple non-sulfur bacteria.

A eukaryotic cell may be, but is not limited to, fungus (e.g. a yeast or a filamentous fungus), an algae, a plant cell, a cell line.

A eukaryotic cell may be a fungus, such as a filamentous fungus or yeast. Filamentous fungal strains include, but are not limited to, strains of *Acremonium, Aspergillus* (e.g. *A. niger, A oryzae, A. nidulans*), *Agaricus, Aureobasidium, Coprinus, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium* (e.g. *P. chrysogenum, P. camemberti*), *Piromyces, Phanerochaete Pleurotus, Podospora, Pycnoporus, Rhizopus, Schizophyllum, Sordaria, Talaromyces, Rasamsonia* (e.g. *Rasamsonia emersonii*), *Thermoascus, Thielavia, Tolypocladium, Trametes* and *Trichoderma*.

Yeast cells may be selected from the genera: *Saccharomyces* (e.g., *S. cerevisiae, S. bayanus, S. pastorianus, S. carlsbergensis*), *Kluyveromyces, Candida* (e.g., *C. rugosa, C. revkaufi, C. pulcherrima, C. tropicalis, C. utilis*), *Pichia* (e.g., *P. pastoris*), *Schizosaccharomyces, Issatchenkia, Zygosaccharomyces, Hansenula, Kloeckera, Schwanniomyces*, and *Yarrowia* (e.g., *Y. lipolytica*, formerly classified as *Candida lipolytica*).

The cell may be an algae, a microalgae or a marine eukaryote. The cell may be a Labyrinthulomycetes cell, preferably of the order Thraustochytriales, more preferably of the family Thraustochytriaceae, more preferably a member of a genus selected from the group consisting of *Aurantiochytrium, Oblongichytrium, Schizochytrium, Thraustochytrium*, and *Ulkenia*, even more preferably *Schizochytrium* sp. ATCC #20888.

In one embodiment, the recombinant cell as disclosed herein belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*, for example a *Saccharomyces cerevisiae* cell, a *Yarrowia lipolytica* cell, a *Candida krusei* cell, an *Issatchenkia orientalis* cell or an *Escherichia coli* cell.

In one embodiment the cell expresses or overexpresses the variant polypeptide according to the first aspect. Herein, "overexpressed", "overexpression" or the like implies that the recombinant host cell expresses more of the polypeptide than a corresponding cell which does not overexpress the polypeptide or, alternatively, that the polypeptide is expressed in a cell which would not typically express that protein. Alternatively, overexpression may be achieved by expressing a variant polypeptide having a higher specific activity. Those skilled in the art know how to achieve overexpression of a variant polypeptide as herein defined.

Typically, a recombinant cell according to the disclosure is capable of producing a glycosylated diterpene, such as a steviol glycoside. For example, a recombinant cell according to the disclosure may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebaudioside A, rebaudioside E, rebaudioside D or rebaudioside M. Typically the recombinant cell is capable of producing rebaudioside M; rebaudioside A and/or other steviol glycosides, including one or more of rebaudioside B, rebaudioside D, stevioside, steviolbioside, rubusoside, and steviol-13-monoside.

A recombinant cell according to the disclosure may comprise one or more recombinant nucleic acid sequences encoding one or more polypeptides having UDP-glycosyltransferase (UGT) activity.

For the purposes of this disclosure, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose).

Figure 3:
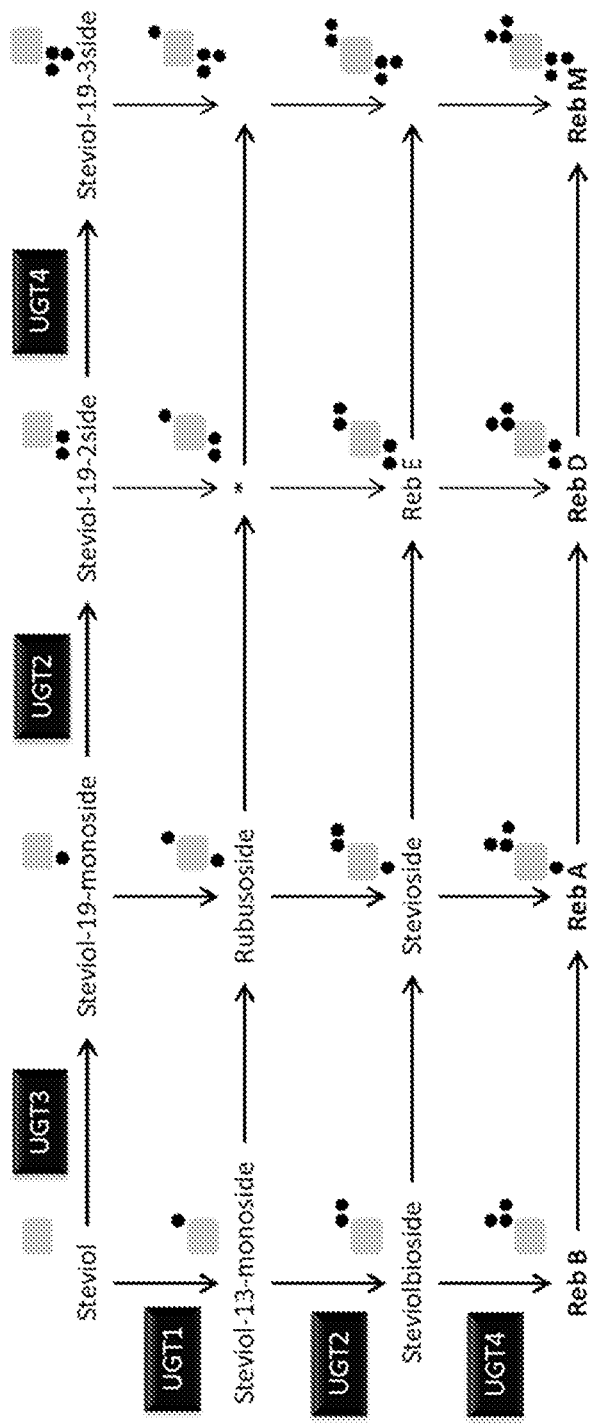
FIG. 3 sets out a schematic diagram of the potential pathways leading to biosynthesis of steviol glycosides.

Such additional UGTs may be selected so as to produce a desired steviol glycoside. Schematic diagrams of steviol glycoside formation are set out in Humphrey et al., Plant Molecular Biology (2006) 61: 47-62 and Mohamed et al., J. Plant Physiology 168 (2011) 1136-1141. In addition, FIG. 3 sets out a schematic diagram of steviol glycoside formation.

A recombinant cell according to the disclosure may thus comprise one or more recombinant nucleic acid sequences encoding:
  (i) a polypeptide having UGT74G1 activity;
  (ii) a polypeptide having UGT2 activity;
  (ii) a polypeptide having UGT85C2 activity; and
  (iii) a polypeptide having UGT76G1 activity.

A recombinant cell suitable for use in the in the production of steviol glycosides may comprise a nucleotide sequence encoding a polypeptide capable of catalysing the addition of a C-13-glucose to steviol. That is to say, a recombinant yeast suitable for use in a method of the disclosure may comprise a UGT which is capable of catalyzing a reaction in which steviol is converted to steviol monoside.

Such a recombinant cell suitable for use in the production of steviol glycosides may comprise a nucleotide sequence encoding a polypeptide having the activity shown by UDP-glycosyltransferase (UGT) UGT85C2, whereby the nucleotide sequence upon transformation of the yeast confers on that yeast the ability to convert steviol to steviol monoside.

UGT85C2 activity is transfer of a glucose unit to the 13-OH of steviol.

Thus, a suitable UGT85C2 may function as a uridine 5'-diphospho glucosyl: steviol 13-OH transferase, and a uridine 5'-diphospho glucosyl: steviol-19-0-glucoside 13-OH transferase. A functional UGT85C2 polypeptides may also catalyze glucosyl transferase reactions that utilize steviol glycoside substrates other than steviol and steviol-19 glucoside. Such sequences may be referred to as UGT1 sequences herein.

A recombinant cell suitable for use in the disclosure may comprise a nucleotide sequence encoding a polypeptide which has UGT2 activity.

A polypeptide having UGT2 activity is one which functions as a uridine 5'-diphospho glucosyl: steviol-13-O-glucoside transferase (also referred to as a steviol-13-monoglucoside 1,2-glycosylase), transferring a glucose moiety to the C-2' of the 13-O-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-0-glucoside and rubusoside, e.g., functional UGT2 polypeptides may utilize stevioside as a substrate, transferring a glucose moiety to the C-2' of the 19-O-glucose residue to produce rebaudioside E. A functional UGT2 polypeptides may also utilize rebaudioside A as a substrate, transferring a glucose moiety to the C-2' of the 19-O-glucose residue to produce rebaudioside D. However, a functional UGT2 polypeptide typically does not transfer a glucose moiety to steviol compounds having a 1,3-bound glucose at the C-13 position, i.e., transfer of a glucose moiety to steviol 1,3-bioside and 1,3-stevioside typically does not occur. A polypeptide having UGT2 activity may encompass a UGT2 polypeptide which preferentially catalyzes conversion of steviol-13-monoside to steviolbioside and/or conversion of rubusoside to stevioside which may help to steer production towards rebaudioside A. Alternatively, a polypeptide having UGT2 activity may encompass a UGT2 polypeptide which preferentially catalyzes conversion of stevioside to rebaudioside E or rubusoside to a compound with an additional sugar at the 19 position which may help to steer production towards rebaudioside M. That is to say preference for addition of a sugar moiety at the 13 position may help steer production towards rebaudioside A, whereas preference for addition of a sugar moiety at the 19 position may help steer production towards rebaudioside M. Example of specific UGT2 are those described in SEQ ID NO: 1, 3, 6, 9, 11, 14, 17, 20, 22 or 25 of WO2016146711.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13 glucoside. As another example, a polypeptide having UGT2 activity may act as a uridine 5'-diphospho L-rhamnosyl: steviol-13-0-glucoside transferase, transferring a rhamnose moiety to the C-2' of the 13-O-glucose of the acceptor molecule, steviol.

A recombinant cell suitable for use in the method of production of steviol glycosides according to the disclosure may comprise a nucleotide sequence encoding a polypeptide having UGT activity may comprise a nucleotide sequence encoding a polypeptide capable of catalyzing the addition of a C-19-glucose to steviolbioside. That is to say, a recombinant yeast of the disclosure may comprise a UGT which is capable of catalyzing a reaction in which steviolbioside is converted to stevioside. Accordingly, such a recombinant yeast may be capable of converting steviolbioside to stevioside. Expression of such a nucleotide sequence may confer on the recombinant yeast the ability to produce at least stevioside.

A recombinant cell suitable for use in the method of production of steviol glycosides according to the disclosure may thus also comprise a nucleotide sequence encoding a polypeptide having the activity shown by UDP-glycosyltransferase (UGT) UGT74G1, whereby the nucleotide sequence upon transformation of the yeast confers on the cell the ability to convert steviolbioside to stevioside.

Suitable UGT74G1 polypeptides may be capable of transferring a glucose unit to the 13-OH or the 19-COOH of steviol. A suitable UGT74G1 polypeptide may function as a uridine 5'-diphospho glucosyl: steviol 19-COOH transferase and a uridine 5'-diphospho glucosyl: steviol-13-O-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences.

A recombinant cell suitable for use in the method of production of steviol glycosides according to the disclosure may comprise a nucleotide sequence encoding a polypeptide capable of catalyzing glucosylation of the C-3' of the glucose at the C-13 position of stevioside. That is to say, a recombinant yeast suitable for use in a method of the disclosure may comprise a UGT which is capable of catalyzing a reaction in which stevioside is converted to rebaudioside A. Accordingly, such a recombinant yeast may be capable of converting stevioside to rebaudioside A. Expression of such a nucleotide sequence may confer on the yeast the ability to produce at least rebaudioside A.

A recombinant cell suitable for use in the method of production of steviol glycosides according to the disclosure may thus also comprise a nucleotide sequence encoding a polypeptide having the activity shown by UDP-glycosyltransferase (UGT) UGT76G1, whereby the nucleotide sequence upon transformation of a yeast confers on that yeast the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-0-1,2 glucoside C-3 ' glucosyl transferase and a uridine 5'-diphospho glucosyl: steviol-19-0-glucose, 13-0-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences. A UGT4 may alternatively or in addition be capable of converting RebD to RebM.

A recombinant cell for use in the method of production of steviol glycosides according to the disclosure typically comprises nucleotide sequences encoding at least one polypeptide having UGT1 activity, at least one polypeptide having UGT2 activity, at least one polypeptide having UGT3 activity and at least one polypeptide having UGT4 activity. One or more of these nucleic acid sequences may be recombinant A given nucleic acid may encode a polypeptide having one or more of the above activities. For example, a nucleic acid may encode a polypeptide which has two, three or four of the activities set out above. Preferably, a recombinant yeast for use in the method of the disclosure comprises UGT1, UGT2 and UGT3 and UGT4 activity. Suitable UGT1, UGT2, UGT3 and UGT4 sequences are described in Table 1 of WO2015/007748.

A recombinant cell according to the disclosure may comprise two or more nucleic acid sequences encoding a polypeptide having any one UGT activity, for example UGT1, 2, 3 or 4, activity. Where a recombinant cell according to the disclosure comprises two or more nucleic acid sequence encoding a polypeptide having any one UGT activity, those nucleic acid sequences may be the same or different and/or may encode the same or different polypeptides. In particular, a recombinant cell according to the disclosure may comprise a nucleic acid sequence encoding a two different UGT2 polypeptides.

A recombinant cell according to the disclosure may comprise one or more recombinant nucleotide sequence(s) encoding one of more of:
a polypeptide having ent-copalyl pyrophosphate synthase activity;
a polypeptide having ent-Kaurene synthase activity; and
a polypeptide having ent-Kaurene oxidase activity.

A recombinant cell according to the disclosure may comprise a recombinant nucleotide sequence encoding a polypeptide having kaurenoic acid 13-hydroxylase activity.

For the purposes of this disclosure, a polypeptide having ent-copalyl pyrophosphate synthase (EC 5.5.1.13) is capable of catalyzing the chemical reaction:

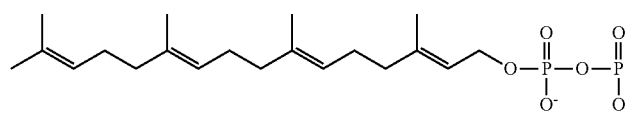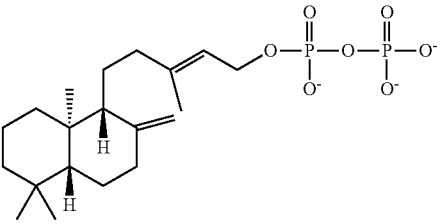

This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this disclosure, a polypeptide having ent-kaurene synthase activity (EC 4.2.3.19) is a polypeptide that is capable of catalyzing the chemical reaction:

ent-copalyl diphosphate ent-kaurene+diphosphate

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-Copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleotide sequence used in a recombinant cell according to the disclosure may encode a polypeptide having ent-copalyl pyrophosphate synthase activity and ent-kaurene synthase activity. Alternatively, the two activities may be encoded two distinct, separate nucleotide sequences.

For the purposes of this disclosure, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

Suitable nucleic acid sequences encoding a kaurenoic acid 13-hydroxylase, may for instance comprise a sequence as set out in SEQ ID. NO: 27, 29, 31, 33, 69, 89, 91, 93, 95, 97, 146, 164, 165, 166, 167 or 185 of WO2015/007748. Other suitable kaurenoic acid 13-hydroxylases are the variant polypeptide described in WO2017/060318 or in PCT/EP2017/081390.

A recombinant cell according to the disclosure may comprise a recombinant nucleic acid sequence encoding a polypeptide having cytochrome p450 reductase activity as disclosed herein (CPR). That is to say, a recombinant cell according to the disclosure may be capable of expressing a nucleotide sequence encoding a polypeptide having cytochrome p450 reductase activity.

In a recombinant cell according to the disclosure, the ability of the recombinant cell to produce geranylgeranyl diphosphate (GGPP) may be upregulated. Upregulated in the context of this disclosure implies that the recombinant cell produces more GGPP than an equivalent non-recombinant cell.

Accordingly, a recombinant cell according to the disclosure may comprise one or more nucleotide sequence(s)

encoding hydroxymethylglutaryl-CoA reductase, farnesyl-pyrophosphate synthetase and geranylgeranyl diphosphate synthase, whereby the nucleotide sequence(s) upon transformation of the microorganism confer(s) on the microorganism the ability to produce elevated levels of GGPP. Thus, a recombinant cell according to the disclosure may comprise one or more recombinant nucleic acid sequence(s) encoding one or more of hydroxymethylglutaryl-CoA reductase, farnesyl-pyrophosphate synthetase and geranylgeranyl diphosphate synthase.

Accordingly, a recombinant cell according to the disclosure may comprise nucleic acid sequences encoding one or more of:
- a polypeptide having hydroxymethylglutaryl-CoA reductase activity;
- a polypeptide having farnesyl-pyrophosphate synthetase activity;
- a polypeptide having geranylgeranyl diphosphate synthase activity.

A cell as defined herein is an organism suitable for genetic manipulation and one which may be cultured at cell densities useful for industrial production of a target product. A suitable cell may be a microorganism, for example one which may be maintained in a fermentation device. A cell may be a cell found in nature or a cell derived from a parent cell after genetic manipulation or classical mutagenesis.

As used herein, a recombinant cell is one which is genetically modified or transformed/transfected with one or more of the nucleotide sequences as defined herein. The presence of the one or more such nucleotide sequences alters the ability of the microorganism to produce steviol or a steviol glycoside, in particular one or more steviol glycosides. A non-recombinant cell, i.e. one that is not transformed/transfected or genetically modified, typically does not comprise one or more of the nucleotide sequences enabling the cell to produce a steviol glycoside. Hence, a non-recombinant cell is typically a cell that does not naturally produce a steviol glycoside, although a cell which naturally produces a steviol or a steviol glycoside and which has been modified according to the disclosure (and which thus expresses a variant polypeptide as disclosed herein) is considered a recombinant cell according to the disclosure.

In particular, it may be possible that the enzymes selected from the group consisting of ent-copalyl pyrophosphate synthase, ent-Kaurene synthase, ent-Kaurene oxidase, and kaurenoic acid 13-hydroxylase, UGTs, hydroxymethylglutaryl-CoA reductase, farnesyl-pyrophosphate synthetase, geranylgeranyl diphosphate synthase and cytochrome p450 reductase are native to the cell and that transformation with one or more of the nucleotide sequences encoding these enzymes may not be required to confer the cell the ability to produce steviol or a steviol glycoside. A preferred cell according to the present disclosure may be a recombinant cell which is naturally capable of producing GGPP (i.e. in its non-recombinant form).

Further improvement of steviol or steviol glycoside production by the cell or recombinant cell may be obtained by classical strain improvement.

In yet a further aspect the disclosure provides therefore a method to produce a recombinant cell capable of producing a steviol glycoside according to the third aspect, wherein the cell comprises a polynucleotide sequence coding for a variant of a parent polypeptide according to the first aspect, said method comprising: a) providing a cell; and b) modifying or transfecting said cell with a nucleic acid or with a nucleic acid construct coding for the variant polypeptide according to the first aspect, and optionally with one or more nucleic acids as defined herein, yielding a recombinant cell according to the third aspect.

Steviol Glycoside Production

In a further aspect, the disclosure provides a process for the preparation of steviol or a steviol glycoside which comprises culturing a recombinant cell as disclosed herein in a suitable nutrient medium and, optionally, recovering the steviol or steviol glycoside.

The term "culturing" refers to a method wherein microorganisms are in a nutrient medium under conditions suitable for growth and/or propagation of said microorganisms and/or for the production of a compound of interest by the microorganisms. These methods are known in the art. When the microorganism is able to express/produce a compound of interest, for example, the microorganisms may be cultured by shake flask culturing, small-scale or large-scale fermentation (including continuous, batch, fed-batch, or solid state fermentations) in laboratory or industrial fermenters performed in a suitable medium and under conditions allowing the compound of interest to be expressed and/or isolated. A suitable nutrient medium comprises carbon sources, nitrogen sources and additional compounds (such as inorganic salts (e.g. phosphate), trace elements and/or vitamins) (see, e.g., Bennett, J. W. and LaSure, L., eds., More Gene Manipulations in Fungi, Academic Press, C A, 1991) and can be performed under aerobic or anaerobic conditions.

The nutrient medium conveniently contains a carbon source, a nitrogen source as well as additional compounds required for growth of the microorganism and/or the formation of the product. For instance, additional compounds may be necessary for inducing the production of the product such as a steviol glycoside. A recombinant cell according to the disclosure may be able to grow on any suitable carbon source known in the art and convert it to a steviol glycoside, e.g. a steviol glycoside. The recombinant cell may be able to convert directly plant biomass, celluloses, hemicelluloses, pectines, rhamnose, galactose, fucose, maltose, maltodextrines, ribose, ribulose, or starch, starch derivatives, molasses, sucrose, glucose, lactose, triglycerides, fatty acids, oil or glycerol. Hence, a preferred cell expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the recombinant cell is able to convert a carbon source selected from the group consisting of glucose, xylose, arabinose, sucrose, lactose and glycerol. The recombinant cell may for instance be a eukaryotic host cell as described in WO03/062430, WO06/009434, EP1499708B1, WO2006096130 or WO04/099381

The steviol glycoside may be, for example, steviol-13-monoside, steviol-19-monoside, 13-[(β-D-Glucopyranosyl)oxy)kaur-16-en-18-oic acid 2-O-β-D glucopyranosyl-β-D-glucopyranosyl ester, rubusoside, stevioside, steviol-19-diside, steviolbioside, rebaudioside A, rebaudioside B, rebaudioside C, rebaudioside E, rebaudioside D or rebaudioside M.

The fermentation or nutrient medium used in the process for the production of a steviol glycoside may be any suitable nutrient medium which allows growth of a particular host cell. The essential elements of the fermentation medium are known to the person skilled in the art and may be adapted to the host cell selected.

The total amount of carbon and nitrogen source to be added to the cultivation process according to the disclosure may vary depending on e.g. the needs of the microorganism and/or the length of the fermentation process.

The ratio between carbon and nitrogen source in a cultivation process may vary considerably, whereby one determinant for an optimal ratio between carbon and nitrogen source is the elemental composition of the product to be formed.

Additional compounds required for growth of a microorganism and/or for product formation, like phosphate, sulphate or trace elements like iron, copper zinc etc., and/or vitamins (e g thiamine, riboflavin, etc.) may be added in amounts that may vary between different classes of microorganisms, i.e. between fungi, yeasts and bacteria. In addition, the amount of additional compound to be added may be determined by the type of product that is formed.

Preferably, the nutrient medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, glucose, sucrose, lactose, molasses, fatty acids, triglycerides and glycerol. Preferably, the nutrient medium also comprises a nitrogen source such as ureum, soy bean meal, corn steep liquor, yeast extract, nitrate salts, urea, ammonia or an ammonium salt such as ammonium sulphate, ammonium chloride, ammonium nitrate or ammonium phosphate. Nutrient medium should allow the organism to reach a certain biomass concentration, such that quantifiable amounts of product can be determined. The medium should also allow the expression of genes needed for the production of steviol glycosides. The suitable medium may differ depending on the recombinant cell.

The process for the production of a steviol glycoside as disclosed herein may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. A SSF process may be particularly attractive if starch, cellulose, hemicellulose or pectin is used as a carbon source in the fermentation process, where it may be necessary to add hydrolytic enzymes, such as cellulases, hemicellulases or pectinases to hydrolyse the substrate. Preferably, the medium should be designed such that high viscosity is avoided, to allow sufficient mixing and gas transfer. Very high concentrations or amounts of carbon source may lead to very high concentration of biomass, which may negatively affect mixing, gas transfer and dissolved oxygen. Very high concentrations or amounts of carbon source could also lead to production levels of steviol glycosides exceeding solubility limits. This is further dependent on the efficiency of the strain for the production of the steviol glycoside (the yield of product on substrate) under that condition. When designing an appropriate medium this should be taken into account.

The process for the production of a steviol glycoside as herein disclosed may be performed on any scale. For example the fermentation process can be performed on a laboratory scale on shake flask, culture plates or micro titer plates (MTP). Typically, it may be performed on an industrial scale, typically using fermentors of various sizes. An industrial scale process is understood to encompass a cultivation process in a fermenter volume which is $\geq 0.01$ m$^3$, or $\geq 0.1$ m$^3$, or $\geq 0.5$ m$^3$, or $\geq 5$ m$^3$, preferably $\geq 10$ m$^3$, more or $\geq 25$ m$^3$, more or $\geq 50$ m$^3$, or $\geq 100$ m$^3$, or $\geq 200$ m$^3$.

Typically, a microbial fermentation process such as a process for the production of a steviol glycoside according to the present disclosure may be divided in a growth phase directed to formation of biomass and a production phase (also indicated as main fermentation) directed to production of a product by the microorganism, such as, e.g. steviol glycosides. The skilled person will comprehend that the two phases of fermentation may not be strictly separated in time, but may overlap to some extent. Moreover, the skilled person will comprehend that during any phase of the cultivation of the microorganism, the product will be produced to some extent.

The growth phase in the fermentation process typically comprises the preparation of the inoculum and the seed fermentation.

The preparation of the inoculum, may occur by transferring aseptically the production microorganism from culture vials into the fermentation medium and can be performed in various ways, e.g. including using shake flask(s), a bubble column or stirred fermenter The typical fermentation temperature in the inoculum phase may range between 20°-40° C., such as 20°-30° C. or 30°-40° C. or 25°-35° C.

Typically, in this phase of the fermentation the pH is usually below 8, below 7.5, or at most 7. In other embodiment, the pH in this phase may be at most 6.5, at most 6, at most 5.5 or at most 5.

Typically, the fermentation during the inoculum phase may be growth-rate limited followed by an oxygen limitation or carbon limitation phase until the fermentation process is upscaled to a seed fermentation. This first inoculum preparation step may be repeated at larger scale with the smaller scale as an inoculum until enough biomass has been produced.

Therefore after sufficient growth, the biomass may be transferred to a seed fermentor, where further growth (i.e. the seed fermentation) may take place. The seed fermentation may typically occur under agitation and typically in the presence of oxygen. This process step can be performed in various settings, such as continuous fermentation, batch fermentation or fed-batch fermentation, preferably batch or fed-batch fermentation. This phase of the fermentation can take place in a bubble column, or stirred fermenter for example. Conditions of oxygen- or carbon limitation can be applied. The medium may comprise any suitable nutrient as discussed herein before, including defined salts and/or vitamins such as thiamine. Further the medium may comprise an antifoam. Typically, the medium used in this phase of the fermentation may be sterilized in the fermenter prior to use in the absence of carbon source, e.g. in the absence of glucose, at a pH preferably below 5 or lower and afterwards adjusted to the pH of the fermentation with any suitable base, e.g. such as using gaseous or liquid ammonia. The fermenter can also be sterilized empty and previously sterilised medium (e.g. by heat shock or filter sterilisation) can be added. The pH in the seed fermentation may be maintained below 8, or below 7, or below 6 or below 5 or below 4. The amount of carbon source such as glucose or any other carbon source as mentioned herein before, may be between 0-200 g/kg, or at most 50, 60, 70, 80, 90, 100, 110, 120, 130, 140, 150, 160, 170, 180 g/kg, or at least 5, 10, 20, 30, 40 g/kg. The fermentation temperature and pH in this phase may be in the same range as the temperature and/or pH used for the inoculum preparation. When the batch carbon source such as glucose s is consumed or almost consumed, glucose or other carbon source may be added or the fermentation can proceed to the main phase (or production phase).

In case further carbon source is added, the latter can occur either in continuous or repeated batch modus. Typically, in the seed fermentation the first phase may be a growth limited phase followed by oxygen limitation or carbon limitation. An antifoam may be applied to control foaming. This seed preparation step may be repeated at larger scale with the smaller scale as an inoculum until enough biomass has been produced.

The main fermentation will typically be the phase wherein the product, such as steviol-glycosides, is produced. This phase may typically be performed in continuous or fed-batch process. Typically, this phase may be performed in a bubble column or stirred fermenter. Typically, the main fermentation will comprise more phases characterised by different limitations. Typically, a first phase may be a batch process growth rate limited followed by an optional oxygen limited phase. The oxygen limited phase may be dispensed with. The second or third phase may typically be a carbon-limited such as glucose-limited production phase. The medium may have a composition as described for the seed fermentation phase. Prior to use, the medium may be sterilized and the pH adjusted as disclosed for the seed fermentation phase. After sterilization of the medium, carbon source may be added in an amount which may be as previously described for the seed fermentation phase.

The recombinant cell used in the process for the preparation of a steviol glycoside may be any suitable recombinant cell as defined herein above. It may be advantageous to use a recombinant eukaryotic cell in the process as they are insensitive to bacteriophage infections. In addition, eukaryotic host cells may be grown at low pH to prevent bacterial contamination.

The recombinant cell as disclosed herein may be a facultative anaerobic microorganism. A facultative anaerobic recombinant host can be propagated aerobically to a high cell concentration. This anaerobic phase can then be carried out at high cell density which reduces the fermentation volume required substantially, and may minimize the risk of contamination with aerobic microorganisms.

The fermentation process for the production of a steviol glycoside as disclosed herein may be an aerobic or an anaerobic fermentation process.

An anaerobic fermentation process may be herein defined as a fermentation process run in the absence of oxygen or in which substantially no oxygen is consumed, preferably s less than 5, 2.5 or 1 mmol/L/h, and wherein organic molecules serve as both electron donor and electron acceptors. The fermentation process as disclosed herein may also first be run under aerobic conditions and subsequently under anaerobic conditions.

The fermentation process may also be run under oxygen-limited, or micro-aerobic, conditions. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used.

The production of a steviol glycoside in the process according to the disclosure may occur during the growth phase of the host cell, during the stationary (steady state) phase or during both phases. It may be possible to run the fermentation process at different temperatures.

The process for the production of a steviol glycoside may be run at a temperature which is optimal for the recombinant host. The optimum growth temperature may differ for each transformed recombinant host and is known to the person skilled in the art. The optimum temperature might be higher than optimal for wild type organisms to grow the organism efficiently under non-sterile conditions under minimal infection sensitivity and lowest cooling cost. Alternatively, the process may be carried out at a temperature which is not optimal for growth of the recombinant host.

The process for the production of a steviol glycoside according to the present disclosure may be carried out at any suitable pH value. If the recombinant host is a yeast, the pH in the fermentation medium preferably has a value of below 6, preferably below 5,5, preferably below 5, preferably below 4,5, preferably below 4, preferably below pH 3,5 or below pH 3,0, or below pH 2,5, preferably above pH 2. An advantage of carrying out the fermentation at these low pH values is that growth of contaminant bacteria in the fermentation medium may be prevented.

Such a process may be carried out on an industrial scale. The product of such a process is one or more steviol glycosides, such one or more of, for example, steviol-13-monoside, steviol-19-monoside, 13403-D-Glucopyranosyl) oxy)kaur-16-en-18-oic acid 2-O-β-D-glucopyranosyl-β-D-glucopyranosyl ester, rubusoside, stevioside, steviol-19-diside, steviolbioside, rebaudioside A, rebaudioside E, rebaudioside D or rebaudioside M.

Recovery of steviol glycoside(s) from the fermentation medium may be performed by known methods in the art, for instance by distillation, vacuum extraction, solvent extraction, crystallization or evaporation.

In the process for the production of a steviol glycoside according to the disclosure, it may be possible to achieve a concentration of above 5 mg/l fermentation broth, preferably above 10 mg/l, preferably above 20 mg/l, preferably above 30 mg/l fermentation broth, preferably above 40 mg/l, more preferably above 50 mg/l, preferably above 60 mg/l, preferably above 70, preferably above 80 mg/l, preferably above 100 mg/l, preferably above 1 g/l, preferably above 5 g/l, preferably above 10 g/l, but usually below 70 g/l.

The disclosure further provides a fermentation broth comprising a steviol glycoside obtainable by the process for the preparation of steviol or a steviol glycoside as herein disclosed.

In the event that one or more steviol glycosides is produced within the microorganism, such cells may need to be treated so as to release them. However in a preferred embodiment the extracellular production of steviol glycosides and particularly of reb M is improved as disclosed in the other aspects of the disclosure. Therefore, at least one steviol glycoside, for example reb M, is produced extracellularly.

In the context of the disclosure "fermentation broth", "culture broth", or "fermentation liquid" may be used interchangeably. A fermentation broth typically comprises culturing medium, the recombinant cell of the disclosure and optionally the product produced by the recombinant cell, e.g. the steviol glycosides.

The disclosure also provides a steviol glycoside obtained by a process for the preparation of a steviol glycoside or obtainable from a fermentation broth as disclosed herein. Such a steviol glycoside may be a non-naturally occurring steviol glycoside, that is to say one which is not produced in plants. Preferably the steviol glycoside comprises at least reb M.

Also provided is a composition comprising one or more steviol glycosides obtained by the process for the preparation of steviol or a steviol glycoside as herein disclosed or obtained from a fermentation broth as herein disclosed. In such a composition, one or more of the steviol glycosides may be a non-naturally occurring steviol glycoside, that is to say one which is not produced in plants. Preferably the composition comprising one or more steviol glycosides obtained by the process for the preparation of steviol glycosides herein disclosed is enriched in rebaudioside M.

A steviol glycoside or composition produced by the fermentation process as disclosed herein may be used in any application known for such compounds. In particular, they may for instance be used as a sweetener, for example in a food or a beverage. According to the disclosure therefore, there is provided a foodstuff, feed or beverage which comprises a composition comprising one or more steviol glycosides as herein disclosed.

For example, a steviol glycoside or a composition as disclosed herein may be formulated in soft drinks, as a tabletop sweetener, chewing gum, dairy product such as yoghurt (e.g. plain yoghurt), cake, cereal or cereal-based food, nutraceutical, pharmaceutical, edible gel, confectionery product, cosmetic, toothpastes or other oral cavity composition, etc. In addition, a steviol glycoside or a composition according to the disclosure can be used as a sweetener not only for drinks, foodstuffs, and other products dedicated for human consumption, but also in animal feed and fodder with improved characteristics.

Accordingly, the disclosure provides, inter alia, a foodstuff, feed or beverage which comprises a steviol glycoside prepared according to a process as disclosed herein.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

A steviol glycoside or a composition of the disclosure can be used in dry or liquid forms. It can be added before or after heat treatment of food products. The amount of the sweetener depends on the purpose of usage. It can be added alone or in the combination with other compounds.

Compounds produced according to the method as disclosed herein may be blended with one or more further non-caloric or caloric sweeteners. Such blending may be used to improve flavour or temporal profile or stability. A wide range of both non-caloric and caloric sweeteners may be suitable for blending with a steviol glycoside or a composition as disclosed herein. For example, non-caloric sweeteners such as mogroside, monatin, aspartame, acesulfame salts, cyclamate, sucralose, saccharin salts or erythritol. Caloric sweeteners suitable for blending with a steviol glycoside or a composition as disclosed herein include sugar alcohols and carbohydrates such as sucrose, glucose, fructose and HFCS. Sweet tasting amino acids such as glycine, alanine or serine may also be used.

A steviol glycoside or a composition as disclosed herein can be used in the combination with a sweetener suppressor, such as a natural sweetener suppressor. It may be combined with an umami taste enhancer, such as an amino acid or a salt thereof.

A steviol glycoside or a composition as disclosed herein can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/thiols, amino acids, a protein, a vitamin, a mineral, and/or a substance classified based on a health benefits, such as cardiovascular, cholesterol-reducing or anti-inflammatory.

A composition with a steviol glycoside or a composition as disclosed herein may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A steviol glycoside or a composition as disclosed herein may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a steviol glycoside or a composition as disclosed herein may be used as a sweetener not only for drinks, foodstuffs, and other products dedicated for human consumption, but also in animal feed and fodder with improved characteristics.

The examples of products where a steviol glycoside or a composition as disclosed herein can be used as a sweetening compound can be as alcoholic beverages such as vodka, wine, beer, liquor, sake, etc.; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, s fish sausage, fish paste, deep fried fish products, dried seafood products, frozen food products, preserved seaweed, preserved meat, tobacco, medicinal products, and many others. In principle, it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

A steviol glycoside or a composition as disclosed herein can be used in dry or liquid forms. It can be added before or after heat treatment of food products. The amount of the sweetener depends on the purpose of usage. It can be added alone or in the combination with other compounds.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions of the present invention can be made by any method known to those skilled in the art that provide homogenous even or homogeneous mixtures of the ingredients. These methods include dry blending, spray drying, agglomeration, wet granulation, compaction, co-crystallization and the like.

In solid form a steviol glycoside or a composition as disclosed herein can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

The composition may include various bulking agents, functional ingredients, colorants, flavors.

The following list of embodiments of the disclosure is hereafter presented which however does not intend to be limiting.

Embodiments of the Disclosure

1. A variant of a parent polypeptide wherein the variant has steviol glycoside transport mediating activity, wherein the variant comprises an amino acid sequence which, when aligned with the amino acid sequence of the parent polypeptide, comprises at least one modification of an amino acid residue corresponding to any of the amino acids in the amino acid sequence of the parent polypeptide, wherein, when measured under the same conditions:
   a) the ratio between the molar concentration of rebaudioside M produced by a recombinant cell expressing the variant and the molar concentration of rebaudioside M produced by a reference cell is at least 0.1; and/or
   b) the ratio between the molar concentration of rebaudioside M and the molar concentration of rebaudioside A produced by a recombinant cell expressing the variant is higher than the ratio between the molar concentration of rebaudioside M and the molar concentration of rebaudioside A produced by a reference cell; and/or
   c) the ratio between the molar concentration of rebaudioside M and the molar concentration of total steviol glycosides produced by a recombinant cell expressing the variant is higher than the ratio between the molar concentration of rebaudioside M and the molar concentration of total steviol glycosides produced by a reference cell;
   wherein a reference cell is a recombinant cell expressing the parent polypeptide.

2. The variant according to any one of the preceding embodiments which is a transport protein selected from an ATP-Binding Cassettes (ABC) transporter, a Major Facilitator Superfamily (MFS) transporter, a Small Multidrug Resistance (SMR) transporter, a transporter belonging to the Resistance-Nodulation-Cell division (RND) family, a Multi-Antimicrobial-Extrusion Protein, more preferably an ATP-Binding Cassette (ABC) transporter.

3. The variant according to any one of the preceding embodiments wherein the parent polypeptide is a transport protein selected from an ATP-Binding Cassette (ABC) transporter, a Major Facilitator Superfamily (MFS) transporter, a Small Multidrug Resistance (SMR) transporter, a transporter belonging to the Resistance-Nodulation-Cell division (RND) family, a Multi-Antimicrobial-Extrusion Protein, more preferably an ATP-Binding Cassette (ABC) transporter.

4. The variant of a parent polypeptide wherein the variant has steviol glycoside transport mediating activity, optionally according to any one of the preceding embodiments, wherein the variant comprises an amino acid sequence which, when aligned with the amino acid sequence set out in SEQ ID NO: 3, comprises at least one modification of an amino acid residue corresponding to any of amino acids in the amino acid sequence according to SEQ ID NO: 3, wherein, when measured under the same conditions:
   a) the ratio between the molar concentration of rebaudioside M produced by a recombinant cell expressing the variant and the molar concentration of rebaudioside M produced by a reference cell is at least 0.1; and/or
   b) the ratio between the molar concentration of rebaudioside M and the molar concentration of rebaudioside A produced by a recombinant cell expressing the variant is higher than the ratio between the molar concentration of rebaudioside M and the molar concentration of rebaudioside A produced by a reference cell; and/or
   c) the ratio between the molar concentration of rebaudioside M and the molar concentration of total steviol glycosides produced by a recombinant cell expressing the variant is higher than the ratio between the molar concentration of rebaudioside M and the molar concentration of total steviol glycosides produced by a reference cell;
   wherein a reference cell is a recombinant cell expressing the parent polypeptide.

5. The variant according to any one of the preceding, wherein the modification occurs in a helical transmembrane region, preferably wherein the variant comprises an amino acid sequence which, when aligned with the amino acid sequence set out in SEQ ID NO: 3, comprises at least one modification of an amino acid residue corresponding to any of amino acids 14-67, 135-156, 159-160, 199-215, 255-258, 262-284, 291-312, 314-328, 375-390, 407-429, 852-869, 890-908, 958-980, 986-1014, 1012-1021, 1059-1062, 1067-1080, 1104-1125, 1127-1128 in the amino acid sequence according to SEQ ID NO: 3, said positions being defined with reference to the amino acid sequence set out in SEQ ID NO: 3.

6. A variant of a parent polypeptide wherein the variant has steviol glycoside transport mediating activity, optionally a variant according to any one of the preceding embodiments, wherein the variant comprises an amino acid sequence which, when aligned with the amino acid sequence set out in SEQ ID NO: 3, comprises at least one modification of an amino acid residue corresponding to any of amino acids, 15, 19, 26, 29, 31, 32, 33, 37, 46, 56, 59, 107, 135, 136, 141, 145, 148, 150, 151, 153, 199, 200, 204, 206, 207, 210, 211, 255, 257, 258, 262, 267, 268, 272, 273, 276, 277, 278, 281, 282, 283, 284, 292, 294, 296, 297, 298, 299, 300, 302, 303, 306, 307, 309, 310, 311, 315, 318, 319, 320, 321, 322, 323, 324, 326, 328, 375, 376, 378, 379, 380, 382, 384, 386, 387, 389, 408, 410, 411, 413, 414, 415, 416, 417, 419, 420, 421, 422, 423, 424, 425, 427, 428, 429, 853, 854, 857, 859, 862, 864, 869, 890, 891, 892, 894, 903, 906, 968, 969, 972, 974, 977, 986, 996, 998, 999, 1001, 1003, 1004, 1010, 1012, 1016, 1017, 1018, 1019, 1020, 1021, 1059, 1060, 1061, 1062, 1063, 1075, 1076, 1107, 1108, 1111, 1112, 1115, 1118, 1120, 1123, 1127, 1128, 1179, 1200, said positions being defined with reference to the amino acid sequence set out in SEQ ID NO: 3.

7. The variant according to any one of the preceding embodiments wherein the modification is a substitution, an addition or a deletion, of an amino acid residue corresponding to any of amino acids 15, 19, 26, 29, 31, 32, 33, 37, 46, 56, 59, 107, 135, 136, 141, 145, 148, 150, 151, 153, 199, 200, 204, 206, 207, 210, 211, 255, 257, 258, 262, 267, 268, 272, 273, 276, 277, 278, 281, 282, 283, 284, 292, 294, 296, 297, 298, 299, 300, 302, 303, 306, 307, 309, 310, 311, 315, 318, 319, 320, 321, 322, 323, 324, 326, 328, 375, 376, 378, 379, 380, 382, 384, 386, 387, 389, 408, 410, 411, 413, 414, 415, 416, 417, 419, 420, 421, 422, 423, 424, 425, 427, 428, 429, 853, 854, 857, 859, 862, 864, 869, 890, 891, 892, 894, 903, 906, 968, 969, 972, 974, 977, 986, 996, 998, 999, 1001, 1003, 1004, 1010, 1012, 1016, 1017, 1018, 1019, 1020, 1021, 1059, 1060, 1061, 1062, 1063, 1075, 1076, 1107, 1108, 1111, 1112, 1115, 1118, 1120, 1123, 1127, 1128, 1179, 1200, said positions being defined with reference to the amino acid sequence set out in SEQ ID NO: 3.

8. The variant according to any one of the preceding embodiments, wherein the variant comprises an amino acid sequence which, when aligned with the amino acid sequence set out in SEQ ID NO: 3, comprises one or more of A or V at position 15, G at position 19, Q or W at position 26, F at position 29, Y or A at position 31, N at position 32, I at position 33, G at position 37, Tat position 46, T at position 56, L at position 59, R at position 107, C at position 135, Y at position 136, K at position 141, I at position 145, Q at position 148, L at position 150, G at position 151, L or P at position 153, T at position 199, Y at position 200, F at position 204, I at position 206, W at position 207, G or V at position 210, L at position 211, A at position 255, C or L at position 257, N or Q or S at position 258, F or I at position 262, G or L at position 267, Q or S or T at position 268, G at position 272, Y at position 273, G at position 276, S at position 277, V at position 278, N at position 281, N at position 282, F at position 283, G or S at position 284, T at position 292, T at position 294, T at position 296, S at position 297, K or L at position 298, L or T or V at position 299, M at position 300, F or Q or S or T or V at position 302, M or R or T at position 303, F or I or M or S at position 306, I or L at position 307, M at position 309, C or N at position 310, T or W at position 311, A at position 315, K at position 318, K at position 319, A at position 320, N at position 321, A or E or L or V at position 322, W at position 323, A at position 324, E at position 326, E at position 328, F or K or H or L or N at position 375, W at position 376, I or N or T or V at position 378, Y at position 379, E or R at position 380, G or S or T or W at position 382, G or N or S or T at position 384, I or L at position 386, A at position 387, M at position 389, G at position 408, A at position 410, F or G at position 411, I at position 413, F or G or R at position 414, V at position 415, W at position 416, A or S or T or W at position 417, G or M at position 419, G or S at position 420, F or I at position 421, M at position 422, A or Q at position 423, L or S at position 424, A or H or L or M or V at position 425, M at position 427, M at position 428, M or S at position 429, V at position 853, G or S at position 854, P at position 857, A or P or S at position 859, T at position 862, A at position 864, V at position 869, P at position 890, T at position 891, F or V at position 892, Q or Y at position 894, N at position 903, V at position 906, Q at position 968, N at position 969, Q at position 972, Q at position 974, A or Q at position 977, H at position 986, Y at position 996, A or G at position 998, N or T at position 999, Y at position 1001, I at position 1003, T at position 1004, T at position 1010, L at position 1012, E at position 1016, A at position 1017, L or V at position 1018, G at position 1019, A at position 1020, A or N or W at position 1021, E at position 1059, T at position 1060, G at position 1061, L at position 1062, I at position 1063, S or L at position 1075, A or G at position 1076, Y at position 1107, K or Q at position 1108, K at position 1111, N at position 1112, G at position 1115, A or F or W at position 1118, M at position 1120, P at position 1123, A or N at position 1127, D at position 1128, N at position 1179, I at position 1200, said positions being defined with reference to the amino acid sequence set out in SEQ ID NO: 3.

9. The variant according to any one of the preceding embodiments, wherein the variant comprises an amino acid sequence which, when aligned with the amino acid sequence set out in SEQ ID NO: 3, comprises at least two modifications of an amino acid residue corresponding to any of amino acids in the amino acid sequence according to SEQ ID NO: 3, wherein, when measured under the same conditions:
   a) the ratio between the molar concentration of rebaudioside M produced by a recombinant cell expressing the variant and the molar concentration of rebaudioside M produced by a reference cell is at least 1.2; and/or
   b) the ratio between the molar concentration of rebaudioside M and the molar concentration of rebaudioside A produced by a recombinant cell expressing the variant is at least 1.2 times the ratio between the molar concentration of rebaudioside M and the molar concentration of rebaudioside A produced by a reference cell; and/or
   c) the ratio between the molar concentration of rebaudioside M and the molar concentration of total steviol glycosides produced by a recombinant cell expressing the variant is at least 1.2 times the ratio between the molar concentration of rebaudioside M and the molar concentration of total steviol glycosides produced by a reference cell;
   wherein the at least two modifications are a substitution of an amino acid residue corresponding to any of amino acids
   322, 375, 376, 378, 382, 384, 386, 420, 421, 424, 425, 429, 890, 891, 969, 977, 1060, 1107, 1111, 1112, 1115, 1118, 1120, 1179,
   said positions being defined with reference to the amino acid sequence set out in SEQ ID NO: 3, wherein a reference cell is a recombinant cell expressing the parent polypeptide.

10. The variant according to any one of the preceding embodiments wherein the molar concentration of rebaudioside M, rebaudioside A and of total steviol glycosides in the ratio's according to embodiment 1 a), 1 b), 1 c), 4 a), 4 b), 4 c), 9 a), 9 b) and 9 c) is the molar concentration produced extracellularly.

11. The variant according to any one of the preceding embodiments wherein the variant comprises an amino acid sequence which, when aligned with the amino acid sequence set out in SEQ ID NO: 3, comprises one or more of A or E or L or V at position 322, F or K or H or L or N at position 375, W at position 376, I or N or T or V at position 378, G or S or T or W at position 382, G or N or S or T at position 384, I or L at position 386, G or S at position 420, F or I at position 421, L or S at position 424, A or H or L or M or V at position 425, M or S at position 429, P at position 890, T at position 891, N at position 969, A or Q at position 977, T at position 1060, Y at position 1107, K at position 1111, N at position 1112, G at position 1115, A or F or W at position 1118, M at position 1120, N at position 1179, said positions being defined with reference to the amino acid sequence set out in SEQ ID NO: 3.

12. The variant according to any one of the preceding embodiments wherein the variant comprises an amino acid sequence which, when aligned with the amino acid sequence set out in SEQ ID NO: 3, comprises the following combinations of amino acid substitutions at positions:

107 and 141; preferably R at position 107 and K at position 141; or 322 and 382; preferably E at position 322 or G at position 382; or 322, 382 and 384; preferably E at position 322, G at position 382 and S or T at position 384; or 322, 382 and 420; preferably E at position 322, G at position 382 and G at position 420; or 322, 382 and 429; preferably E at position 322, G at position 382 and S at position 429; or 322, 382 and 890; preferably E at position 322, G at position 382 and P at position 890; or 322, 382 and 891; preferably E at position 322, G at position 382 and T at position 891; or 322, 382, 969 and 1060; preferably E at position 322, G at position 382, N at position 969 and T at position 1060; or 322, 382 and 977; preferably E at position 322, G at position 382, and A or Q at position 977; or 322, 382 and 1107; preferably E at position 322, G at position 382, and Y at position 1107; or 322, 382, 1111 and 1179; preferably E at position 322, G at position 382, K at position 111 and N at position 1179; or 322, 382 and 1112; preferably E at position 322, G at position 382, and N at position 1112; or 322, 382 and 1115; preferably E at position 322, G at position 382, and G at position 1115; or 322, 382 and 1118; preferably E at position 322, G at position 382, and A at position 1118; or 375, 969 and 1060; preferably F at position 375, N at position 969 and T at position 1060; or 375 and 977; preferably F at position 375 and A at position 977; or 375 and 1107; preferably F at position 375 and Y at position 1107; or 375, 1111 and 1179; preferably F at position 375, K at position 1111 and N at position 1179; or 376, 969 and 1060; preferably W at position 376, N at position 969 and T at position 1060; or 376 and 977; preferably W at position 376 and A at position 977; or 376 and 1107; preferably W at position 376 and Y at position 1107; or 376, 1111 and 1179; preferably W at position 376, K at position 1111 and N at position 1179; or 376 and 1112; preferably W at position 376 and N at position 1112; or 378, 969 and 1060; preferably T at position 378, N at position 969 and T at position 1060; or 378 and 977; preferably T at position 378 and A at position 977; or 378 and 1107; preferably T at position 378 and Y at position 1107; or 378, 1111 and 1179; preferably T at position 378, K at position 1111 and N at position 1179; or 378 and 1112; preferably T at position 378 and N at position 1112; or 384 and 420; preferably S or T at position 384 and G at position 420; or 384 and 429; preferably S or T at position 384 and S at position 429; or 384 and 890; preferably S or T at position 384 and P at position 890; or 384 and 891; preferably S at position 384 and T at position 891; or 384, 969 and 1060; preferably G or N or T at position 384, N at position 969 and T at position 1060; or 384 and 977; preferably G or N or S or T at position 384 and A at position 977; or preferably S at position 384 and A or Q at position 977; or preferably T at position 384 and Q at position 977; or 384 and 1107; preferably G or N or S or T at position 384 and Y at position 1107; or 384, 1111 and 1179; preferably G or N or S or T at position 384, K at position 1111 and N at position 1179; or 384 and 1112; preferably G or N or S or T at position 384 and N at position 1112; or 384 and 1115; preferably S or T at position 384 and G at position 1115; or 384 and 1118; preferably S or T at position 384 and A at position 1118; or 386, 969 and 1060; preferably I or L at position 386, N at position 969 and T at s position 1060; or 386 and 977; preferably L at position 386 and A at position 977; or 386 and 1107; preferably I or L at position 386 and Y at position 1107; or 386, 1111 and 1179; preferably I or L at position 386, K at position 1111 and N at position 1179; or 386 and 1112; preferably I or L at position 386 and N at position 1112; or 420 and 429; preferably G at position 420 and S at position 429; or 420 and 891; preferably G at position 420 and T at position 891; or 420 and 890; preferably G at position 420 and P at position 890; or 420, 969 and 1060; preferably G at position 420, N at position 969 and T at position 1060; or 420 and 977; preferably G at position 420 and A or Q at position 977; or 420 and 1107; preferably G at position 420 and Y at position 1107; or 420, 1111 and 1179; preferably G at position 420, K at position 1111 and N at position 1179; or 420 and 1112; preferably G at position 420 and N at position 1112; or 420 and 1115; preferably G at position 420 and G at position 1115; or 420 and 1118; preferably G at position 420 and A at position 1118; or 421, 969 and 1060; preferably F at position 421, N at position 969 and T at position 1060; or 421 and 977; preferably F at position 421 and A at position 977; or 421, 1111 and 1179; preferably F at position 421, K at position 1111 and N at position 1179; or
421 and 1112; preferably F at position 421 and N at position 1112; or
424, 969 and 1060; preferably L at position 424, N at position 969 and T at position 1060; or
424 and 977; preferably L at position 424 and A at position 977; or
424 and 1107; preferably L at position 424 and Y at position 1107; or
424, 1111 and 1179; preferably L at position 424, K at position 1111 and N at position 1179; or
424 and 1112; preferably L at position 424 and N at position 1112; or
425, 969 and 1060; preferably A or L or M at position 425, N at position 969 and T at position 1060; or
425 and 1107; preferably A or L or M at position 425 and Y at position 1107; or
425, 1111 and 1179; preferably A or L or M at position 425, K at position 1111 and N at position 1179; or
425 and 1112; preferably A or L or M at position 425 and N at position 1112; or
429 and 890; preferably S at position 429 and P at position 890; or
429, 969 and 1060; preferably S at position 429, N at position 969 and T at position 1060; or
429 and 1107; preferably S at position 429 and Y at position 1107; or
429, 1111 and 1179; preferably S at position 429, K at position 1111 and N at position 1179; or
429 and 1112; preferably S at position 429 and N at position 1112; or
429 and 1115; preferably S at position 429 and G at position 1115; or
429 and 1118; preferably S at position 429 and A at position 1118; or
890, 969 and 1060; preferably P at position 890, N at position 969 and T at position 1060; or
890, 1111 and 1179; preferably P at position 890, K at position 1111 and N at position 1179; or
890 and 1112; preferably P at position 890 and N at position 1112; or
891, 969 and 1060; preferably T at position 891, N at position 969 and T at position 1060; or
891, 1111 and 1179; preferably T at position 891, K at position 1111 and N at position 1179; or
891 and 1112; preferably T at position 891 and N at position 1112; or
892 and 986; preferably F at position 892 and H at position 986; or
969, 977 and 1060; preferably N at position 969, A or Q at position 977 and T at position 1060; or
969, 998 and 1060; preferably N at position 969, A at position 998 and T at position 1060; or
969 and 1060; preferably N at position 969 and T at position 1060; or
969, 1060 and 1107; preferably N at position 969, T at position 1060 and Y at position 1107; or
969, 1060 and 1108; preferably N at position 969, T at position 1060 and K at position 1108; or
969, 1060 and 1112; preferably N at position 969, T at position 1060 and N at s position 1112; or
969, 1060, 1111 and 1179; preferably N at position 969, T at position 1060, K at position 1111 and N at position 1179; or
969, 1060 and 1115; preferably N at position 969, T at position 1060 and G at position 1115; or
969, 1060 and 1118; preferably N at position 969, T at position 1060 and A at position 1118; or
969, 1060 and 1120; preferably N at position 969, T at position 1060 and M at position 1120; or
977 and 1107; preferably A at position 977 and Y at position 1107; or
977, 1111 and 1179; preferably A or Q at position 977, K at position 1111 and N at position 1179; or
977 and 1112; preferably A or Q at position 977 and N at position 1112; or
998, 1111 and 1179; preferably A at position 998, K at position 1111 and N at position 1179; or
998 and 1112; preferably A at position 998 and N at position 1112; or
1075 and 1076; preferably L at position 1075 and A at position 1076; or
1107, 1111 and 1179; preferably Y at position 1107, K at position 1111 and N at position 1179; or
1107 and 1112; preferably Y at position 1107 and N at position 1112; or
1108, 1111 and 1179; preferably K at position 1108, K at position 1111 and N at position 1179; or
1108 and 1112; preferably K at position 1108 and N at position 1112; or
1108 and 1200; preferably Q at position 1108 and I at position 1200; or
1108 and 1200; preferably Q at position 1108 and I at position 1200; or
1111 and 1179; preferably K at position 1111 and N at position 1179; or
1111, 1112 and 1179; preferably K at position 1111, N at position 1112 and N at position 1179; or
1111, 1115 and 1179; preferably K at position 1111, G at position 1115 and N at position 1179; or
1111, 1118 and 1179; preferably K at position 1111, A at position 1118 and N at position 1179; or
1111, 1120 and 1179; preferably K at position 1111, M at position 1120 and N at position 1179; or
1112 and 1115; preferably N at position 1112 and G at position 1115; or
1112 and 1118; preferably N at position 1112 and A at position 1118; or
1112 and 1120; preferably N at position 1112 and M at position 1120.

13. The variant according to any one of the preceding embodiments, wherein the parent polypeptide comprises the amino acid sequence set out in SEQ ID NO: 3 or comprises an amino acid sequence which has at least 50% sequence identity with the amino acid sequence set out in SEQ ID NO:3.

14. The variant according to any one of the preceding embodiments, wherein the variant polypeptide has at least 50% sequence identity with the amino acid sequence set out in SEQ ID NO:3.

15. The variant according to any one of the preceding embodiments, wherein the molar concentration of rebaudioside M, the molar concentration of rebaudioside A and the molar concentration of total steviol glycosides produced by a recombinant cell expressing the variant or produced by a recombinant cell expressing the parent polypeptide is determined by:
 a) growing the recombinant cell for a fixed period of time in a suitable nutrient medium under conditions which allow the recombinant cell to grow and produce steviol glycosides;
 b) recovering the steviol glycosides produced by the cell by subjecting the cell culture to homogenization and treating for 10 minutes at 90° C. to release the cell content, cool down to room temperature, centrifuge at 1500 g for 10 minutes to separate the supernatant from the cell debris, separating the supernatant;
c) measuring the molar concentration of rebaudioside M, rebaudioside A and total steviol glycosides in the supernatant obtained in step b).

16. The variant according to any one of the preceding embodiments, wherein the molar concentration of rebaudioside M, the molar concentration of rebaudioside A and the molar concentration of total steviol glycosides produced extracellularly by a recombinant cell expressing the variant or produced by a recombinant cell expressing the parent polypeptide is determined by:
    a) growing the recombinant cell for a fixed period of time in a suitable nutrient medium under conditions which allow the recombinant cell to grow and to produce steviol glycosides, preferably under conditions wherein steviol glycosides are soluble;
    b) recovering the steviol glycosides produced extracellularly by the cell by subjecting the cell culture to centrifugation at 1500 g for 10 minutes to separate the supernatant from the intact cells, separating the supernatant;
    c) measuring the molar concentration of rebaudioside M, rebaudioside A and total steviol glycosides in the supernatant obtained in step b).

17. The variant according to embodiment 15 or 16 wherein in step c) the molar concentration of rebaudioside M, rebaudioside A and total steviol glycosides in the supernatant is measured using an UPLC coupled to a TQ Mass Spectrometer equipped with an electrospray ionization source operated in the negative-ion mode in MRM mode at the deprotonated molecules [M-H]$^-$ for the steviol glycosides, with exclusion of Rebaudioside A and rubusoside, which are monitored at [M-H-hexose] comprising the steps of: diluting the supernatant obtained according to embodiment 15 b) or 16 b) with acetonitrile to a concentration of 33% v/v acetonitrile, separating the steviol glycosides in the supernatant using a 2.1×100 mm, with 1.8 µm particle size, silica based, C18 reverse-phase column, using a gradient elution with (A) 50 mM ammonium acetate in LC-MS grade water, and (B) LC-MS grade acetonitrile, using the following gradient: from 30% v/v to 35% v/v B in 0.5 minutes, keep at 35% v/v B for 0.8 minutes, from 35% v/v B to 95% v/v B in 0.7 minutes, keep at 95% v/v B for 0.5 minutes, re-equilibrating with 30% v/v B for 1.5 mM, using a flow rate of 0.6 ml/min, using an injection volume of 5 µl and a column temperature of 50° C., quantifying the steviol glycosides using an external calibration line of the components in the range of 10-600 ng/ml, wherein the corresponding analyzed samples are diluted so that the concentration of the desired components fall in the linear range of calibration line.

18. The variant according to embodiment 15 or 16 wherein in step c) the molar concentration of rebaudioside M, rebaudioside A and total steviol glycosides in the supernatant is measured using an UPLC coupled to a Photo Diode Array Detector, comprising the steps of diluting the supernatant obtained according to embodiment 15 b) or 16 b) with acetonitrile to a concentration of 25% v/v acetonitrile, separating the steviol glycosides in the supernatant using a 4.6×150 mm with 3 µm particle size silica based, reversed phase difunctionally bonded $C_{18}$ column and detection at 210 nm, using an elution gradient with (A) 25% v/v acetonitrile+0.00166% v/v acetic acid in purified water, and B) LC-MS grade acetonitrile as mobile phases, using the following gradient: 0% v/v B (=100% A) for 2 minutes, 0% v/v B to 46% v/v B in 11 minutes, 46% v/v B to 98% v/v B in 0.1 minutes, keep at 98% v/v B for 4 minutes, from 98% v/v B to 0% v/v B in 0.1 minutes, re-equilibrating the column at 100% v/v A for 5 minutes, using a flow rate at 1 ml/min, using an injection volume of 10 µl and a column temperature at 50° C., quantifying the steviol glycosides using an external calibration line of the components in the range of 2-100 µg/ml, wherein the corresponding analyzed samples are diluted so that the concentration of the desired components fall in the linear range of calibration line.

19. A nucleic acid sequence coding for a variant polypeptide according to any one of the preceding embodiments.

20. A nucleic acid construct comprising the nucleic acid sequence according to embodiment 19, optionally wherein the nucleic acid coding for the variant polypeptide is operably linked to at least one control sequence capable of directing the expression of said variant in a suitable recombinant cell.

21. A method to produce a variant polypeptide according to any one of the preceding embodiments comprising:
    a) providing a parent polypeptide, optionally wherein the parent polypeptide has steviol glycoside transport mediating activity;
    b) modifying in the parent polypeptide sequence at least one amino acid residue to yield a variant polypeptide sequence, optionally wherein the modification in the parent polypeptide sequence occurs in a portion of a sequence which corresponds to a helical transmembrane region; and optionally
    c) selecting a variant polypeptide which when expressed in a recombinant cell has steviol glycoside transport mediating activity and has the following characteristics, when measured under the same conditions:
        i) the ratio between the molar concentration of rebaudioside M produced by a recombinant cell expressing the variant and the molar concentration of rebaudioside M produced by a reference cell is at least 0.1; and/or
        ii) the ratio between the molar concentration of rebaudioside M and the molar concentration of rebaudioside A produced by a recombinant cell expressing the variant is higher than the ratio between the molar concentration of rebaudioside M and the molar concentration of rebaudioside A produced by a reference cell; and/or
        iii) the ratio between the molar concentration of rebaudioside M and the molar concentration of total steviol glycosides produced by a recombinant cell expressing the variant is higher than the ratio between the molar concentration of rebaudioside M and the molar concentration of total steviol glycosides produced by a reference cell;
        wherein a reference cell is a recombinant cell expressing the parent polypeptide, optionally wherein the molar concentration of rebaudioside M, rebaudioside A and total steviol glycosides in the ratio's according to i), ii), and iii) is the molar concentration produced extracellularly.

22. The method to produce a variant polypeptide according to embodiment 21, wherein modifying in the parent polypeptide sequence at least one amino acid residue to yield a variant polypeptide sequence in step b) of the method to produce the variant comprises:
    I) aligning the amino acid sequence of the parent polypeptide with the amino acid sequence set out in SEQ ID NO: 3, II) modifying an amino acid residue corresponding to any of amino acids, 15, 19, 26, 29, 31, 32, 33, 37, 46, 56, 59, 107, 135, 136, 141, 145, 148, 150, 151, 153, 199, 200, 204, 206, 207, 210, 211, 255, 257, 258, 262, 267, 268, 272, 273, 276, 277, 278, 281, 282, 283, 284, 292, 294, 296, 297, 298, 299, 300, 302, 303, 306, 307, 309, 310, 311, 315, 318, 319, 320, 321, 322, 323, 324, 326, 328, 375, 376, 378, 379, 380, 382, 384, 386, 387, 389, 408, 410, 411, 413, 414, 415, 416, 417, 419, 420, 421, 422, 423, 424, 425, 427, 428, 429, 853, 854, 857, 859, 862, 864, 869, 890, 891, 892, 894, 903, 906, 968, 969, 972, 974, 977, 986, 996, 998, 999, 1001, 1003, 1004, 1010, 1012, 1016, 1017, 1018, 1019, 1020, 1021, 1059, 1060, 1061, 1062, 1063, 1075, 1076, 1107, 1108, 1111, 1112, 1115, 1118, 1120, 1123, 1127, 1128, 1179, 1200, said positions being defined with reference to the amino acid sequence set out in SEQ ID NO: 3.

23. The method to produce a variant polypeptide according to any one of embodiments 21 or 22 wherein the variant polypeptide obtained in step c) of the method to produce the variant is a variant polypeptide according to any one of the embodiments 1 to 18.

24. A recombinant cell capable of producing a steviol glycoside, wherein the cell comprises a nucleic acid coding for a variant of a parent polypeptide according to any one of embodiments 1 to 18 or obtainable by a method according to any one of embodiments 21 to 23.

25. The recombinant cell according to embodiment 24, wherein the cell expresses or overexpresses the variant polypeptide.

26. The recombinant cell according to any one of embodiments 24 or 25 which comprises one or more recombinant nucleotide sequence(s) encoding:
 a polypeptide having ent-copalyl pyrophosphate synthase activity;
 a polypeptide having ent-Kaurene synthase activity;
 a polypeptide having ent-Kaurene oxidase activity; and
 a polypeptide having kaurenoic acid 13-hydroxylase activity.

27. The recombinant cell according to any one of embodiments 24 to 26 which comprises a recombinant nucleic acid sequence encoding a polypeptide having NADPH-cytochrome p450 reductase activity.

28. The recombinant cell according to any one of embodiments 24 to 27 which comprises a recombinant nucleic acid sequence encoding one or more of:
 (i) a polypeptide having UGT74G1 activity;
 (ii) a polypeptide having UGT2 activity;
 (iii) a polypeptide having UGT85C2 activity; and
 (iv) a polypeptide having UGT76G1 activity.

29. The recombinant cell according to any one of embodiments 24 to 28, wherein the cell belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia*, Yamadazyma or *Escherichia*.

30. The recombinant cell according to embodiment 29, wherein the recombinant cell is a *Saccharomyces cerevisiae* cell, a *Yarrowia lipolytica* cell, a *Candida krusei* cell, an *Issatchenkia orientalis* cell or an *Escherichia coli* cell.

31. The recombinant cell according to any one of embodiments 24 to 30, wherein the ability of the cell to produce geranylgeranyl diphosphate (GGPP) is upregulated.

32. The recombinant cell according to any one of embodiments 24 to 31 which comprises a nucleic acid sequence encoding one or more of:
 a polypeptide having hydroxymethylglutaryl-CoA reductase activity; or
 a polypeptide having farnesyl-pyrophosphate synthetase activity.

33. A method to produce a recombinant cell capable of producing a steviol glycoside according to any one of embodiments 24 to 32, wherein the cell comprises a polynucleotide sequence coding for a variant of a parent polypeptide according to any one of embodiments 1 to 18, comprising: a) providing a cell; and b) modifying or transfecting said cell with a nucleic acid according to embodiment 19 or with a nucleic acid construct according to embodiment 20, optionally with one or more nucleic acids according to any one of embodiments 26 to 28, 31 or 32, yielding a recombinant cell according to any one of embodiments 24 to 32.

34. A process for the preparation of a steviol glycoside which comprises fermenting a recombinant cell according to any one of embodiments 24 to 32 in a suitable fermentation medium and, optionally, recovering the steviol glycoside.

35. The process for the preparation of a steviol glycoside according to embodiment 34, wherein the process is carried out on an industrial scale.

36. A fermentation broth comprising a steviol glycoside obtainable by the process according to embodiment 34 or 35.

37. A steviol glycoside obtainable by a process according to embodiment 34 or 35 or obtained from a fermentation broth according to embodiment 36.

38. A composition comprising one or more steviol glycosides obtained by a process according to embodiment 34 or 35.

39. A foodstuff, feed or beverage which comprises a steviol glycoside according to embodiment 37 or a composition according to embodiment 38.

The following examples are presented which however does not intend to be limiting the scope of the disclosure.

EXAMPLES

Assay for Measuring Steviol Glycosides
Liquid Chromatography with Mass Spectrometer (LC-MS) Determination Steviol glycosides were analysed on an Acquity UPLC (Waters) coupled to a XEVO-TQ Mass Spectrometer (Waters) equipped with an electrospray ionization source operated in the negative-ion mode in MRM mode at the deprotonated molecules [M-H]– for all steviol glycosides studied, except for Rebaudioside A and rubusoside, which are monitored at [M-H-hexose]–.

The chromatographic separation was achieved with a 2.1×100 mm 1.8 µm particle size, Acquity UPLC® HSS T3 column, using a gradient elution with (A) 50 mM ammonium acetate in LC-MS grade water, and B) LC-MS grade acetonitrile as mobile phases. The 4 min. gradient started from 30% B linearly increasing to 35% B in 0.5 minutes and kept at 35% B for 0.8 minutes, then linearly increased to 95% B in 0.7 minutes and kept there for 0.5 minutes, then re-equilibrating with 30% B for 1.5 min. The flow rate was kept at 0.6 ml/min, using an injection volume of 5 µl and the column temperature was set to 50° C. The desired components were quantified using an external calibration line of the components in the range of 10-600 ng/ml. The corresponding samples analyzed were diluted accordingly so the concentration of the desired components fell in the linear range of calibration line. The end concentration of acetonitrile in the sample was 33%. The concentration of the components in the samples was calculated using the Target- Lynx software (Waters) using a quadratic calibration line whereby the origin was forced through zero and the weighting function 1/x is used.

Commercially available references were used for Rebaudioside A, Rebaudioside B, Rebaudioside D, stevioside, steviolbioside, rubusoside. References for Rebaudioside M and steviol-13-monoside were provided by DSM.

Example 1. Construction of Transporter Variants Recipient *Yarrowia* Strain

*Yarrowia lipolytica* strain STVP001 was constructed in comparable fashion to the *Yarrowia lipolytica* STV2019 strain described in Example 7 of patent application WO2015/007748. *Yarrowia lipolytica* strain STVP001 contains all the elements for the production of steviol glycosides including Rebaudioside A (RebA) and Rebaudioside M (RebM). It has one or several copies over-expressed of the genes listed in Table 1.

TABLE 1

Polypeptide sequences of the enzymes involved in the biosynthetic pathway of steviol glycosides

| SEQ ID | annotation | description |
|---|---|---|
| SEQ ID NO: 4 (this disclosure) | tHMG | Truncated 3-hydroxy-3-methylglutaryl coenzyme A reductase |
| SEQ ID NO: 5 (this disclosure) | GGS | Variant Geranylgeranyl diphosphate synthase |
| SEQ ID NO: 62 in WO2013110673 | CPS | copalyl diphosphate synthase |
| SEQ ID NO: 66 in WO2013110673 | KS | kaurene synthase |
| SEQ ID NO: 24 in WO2013110673 | KO2 | kaurene oxidase |
| SEQ ID NO: 86 in WO2015007748 | KO_Gib | kaurene oxidase |
| SEQ ID NO: 34 in WO2015007748 | KAH | Kaurenoic acid 13-hydroxylase |
| SEQ ID NO: 3 in WO2017060318 | KAH4_m4 | Kaurenoic acid 13-hydroxylase |
| SEQ ID NO: 6 (this disclosure) | KAH60 | Kaurenoic acid 13-hydroxylase |
| SEQ ID NO: 58 in WO2013110673 | CPR | NADPH-cytochrome P450 reductase |
| SEQ ID NO: 72 in WO2013110673 | UGT85C2 | UDP-glucosyltransferase |
| SEQ ID NO: 25 in WO2016146711 | UGT2 | UDP-glucosyltransferase |
| SEQ ID NO: 74 in WO2013110673 | UGT74G1 | UDP-glucosyltransferase |
| SEQ ID NO: 76 in WO2013110673 | UGT76G1 | UDP-glucosyltransferase |
| SEQ ID NO: 4 in WO2016151046 | RT18 | UDP-glucosyltransferase |

The genes of Table 1 are expressed using promoters and terminators listed in table 2.

TABLE 2

Polynucleotide sequences of promoters and terminators

| SEQ ID | Element type | Annotation |
|---|---|---|
| SEQ ID NO: 193 in WO2013110673 | Promoter | Yl_TPI.pro |
| SEQ ID NO: 74 in WO2016146711 | Terminator | Yl_ACT1.ter |
| SEQ ID NO: 63 in WO2016146711 | Promoter | pHSP |
| SEQ ID NO: 64 in WO2016146711 | Promoter | pHYPO |
| SEQ ID NO: 65 in WO2016146711 | Promoter | pENO |
| SEQ ID NO: 66 in WO2016146711 | Promoter | pCWP |
| SEQ ID NO: 68 in WO2016146711 | Promoter | Yl_YP001.pro |

TABLE 2-continued

Polynucleotide sequences of promoters and terminators

| SEQ ID | Element type | Annotation |
|---|---|---|
| SEQ ID NO: 69 in WO2016146711 | Terminator | xprT |
| SEQ ID NO: 71 in WO2016146711 | Terminator | gpdT |
| SEQ ID NO: 72 in WO2016146711 | Terminator | pgmT |
| SEQ ID NO: 73 in WO2016146711 | Terminator | pgkT |
| SEQ ID NO: 21 in WO2016151046 | Promoter | Yl_SCP2.pro |

The ORF (as defined in SEQ ID NO: 1) and the terminator sequence of the gene coding for the *Yarrowia lipolytica* endogenous transporter YALIOE25201 was deleted from the strain STVP001. Two DNA elements were transformed to strain STVP001, according to the strategy depicted in FIG. 1. Each DNA element (a left and a right DNA element) contained a flanking region of ~1 kb identical to the region downstream (for the right element) or upstream (for the left element) to the YALIOE25201 ORF, respectively. Each element also contained a flanking region identical to a portion of the other DNA element, to allow recombination of the two DNA elements with each other at the genomic location. In particular the left DNA element also contained a green fluorescent protein (GFP) expression cassette and a portion of HygB marker expression cassette while the right element contained a portion of the HygB marker expression cassette partially overlapping with the corresponding portion of the left DNA element. SEQ ID NO: 2 depicts the ORF of SEQ ID NO: 1 including at the 5'-end terminus the 1 kb flanking region (identical to the 5'-end of the left element) and at the 3'-end terminus the terminator (300 bp) and the 999 kb flanking region (the latter identical to the 3'-end of the right element). Double cross-over of these DNA elements at the genomic location of YALIOE25201 resulted in the deletion of YALIOE25201, with integration of a green fluorescent protein (GFP) expression cassette and a functional HygB marker cassette in the genome.

Transformants were selected on agar plates containing 100 μg/ml hygromycin. Diagnostic PCR confirmed the deletion of the YALIOE25201 ORF. The presence of GFP was confirmed optically. The YALIOE25201 deletion strain was named STVP002

Example 2. Production of RebA and RebM in Strains STVP001 and STVP002

To establish the effect of the deletion of the YALIOE25201 transporter, a production test was performed. A 96-well half deep well plate containing 200 μl YEP with glucose per well was inoculated with colony material using a tooth pick. The plate was sealed with a breathable seal and incubated in an Infors incubator at 30° C., 80% humidity shaking at 750 rpm for 48 hours. 40 μl of pre-culture was used to inoculate 2.5 ml mineral medium (based on Verduyn, Yeast vol 8, 501-517 (1992)) but wherein ureum instead of ammonium sulfate was used as a nitrogen source), at pH 6, with glucose as carbon source. This 24-well plate was sealed with a breath seal and incubated in an Infors incubator at 30° C., 80% humidity shaking at 500 rpm for 120 hours.

Quantification of Steviol Glycosides Concentrations Secreted by Strains STVP001 and STVP002

After growth, cells of the 24-well cultures were pelleted by centrifuging the plates at 1500 g for 10 minutes. After centrifugation supernatant was transferred and diluted in 33% acetonitrile and the steviol glycoside concentrations were determined using Liquid Chromatography with Mass Spectrometer (LC-MS). The quantification of RebA and RebM in the supernatant of strain STVP001 and STVP002 is shown in table 3.

Quantification of Intracellular Steviol Glycosides in Strains STVP001 and STVP002

The remaining supernatant of the 24-well culture was decanted from the pellet in the 24-well plate. To wash the cells, 2.5 ml of PBS was added to each well and the cell pellet was re-suspended. The cells were pelleted by centrifuging the plates at 1500 g for 10 minutes and the supernatant decanted. 2.5 ml of milli-Q water was added to each well and the cell pellet was re-suspended. 1 ml of the re-suspended cell pellet was harvested from the 24-well plate and re-arrayed in a 96-half deep well plate. The 96-half deep well plate containing the pellet fraction was incubated in a water bath for 10 minutes at 90° C. and allowed to cool down to room temperature. To 1 ml of the pellet fraction 0.5 ml of 100% acetonitrile was added to each well resulting in a 1.5-fold dilution and an acetonitrile concentration of 33%. The cell debris of the pellet fraction was spun down by centrifuging the plates at 1500 g for 10 minutes. The resulting supernatant was further diluted with 33% acetonitrile and the steviol glycoside concentrations were determined using Liquid Chromatography with Mass Spectrometry (LC-MS). The quantification of intracellular total steviol glycosides and of RebA and RebM in strains STVP001 and STVP002 are shown in table 4.

TABLE 3

Quantification of RebA and RebM in the supernatant in strains STVP001 and STVP002. Values are determined in molar concentrations and normalized to molar concentrations in strain STVP001.

| Strain | RebA | RebM |
| --- | --- | --- |
| STVP001 | 100 | 100 |
| STVP002 | 20 | 53 |

The results in Table 3 illustrate that deletion of YALIOE25201 has a profound negative impact on the extracellular production of RebA and RebM. The effect on RebA is larger than on RebM.

TABLE 4

Intracellular steviol glycosides concentrations in strain STVP001 and YALI0E25201 deletion strain STVP002. Values are determined in molar concentrations, and normalized to molar concentrations in strain STVP001. Sum steviol glycosides includes RebA, RebM, RebD, RebB, stevioside, steviolbioside, rubusoside, steviol-13-monoside.

| Strain | Sum steviol glycosides | RebA | RebM |
| --- | --- | --- | --- |
| STVP001 | 100 | 100 | 100 |
| STVP002 | 695 | 339 | 1248 |

The results in Table 4 illustrate that deletion of YALIOE25201 has a profound impact on the intracellular concentration of steviol glycosides, wherein the steviol glycoside concentrations are much higher in the YALIOE25201-transporter-deletion strain STVP002. Hence deletion of the YALIOE25201 transporter causes intracellular accumulation of steviol glycosides. The effect is more pronounced for RebM.

Taken together these results illustrate that the YALIOE25201 transporter is a highly relevant transporter for steviol glycosides. Deletion of the YALIOE25201 transporter results in a several fold increase in the intracellular concentration of steviol glycosides, and a several fold increase in the intracellular concentration of RebM. The results further illustrate that in terms of extracellular RebM production a RebM-producing host benefits from having a RebM export mechanism.

Example 3. Introducing Transporters in Strain STVP002

Figure 2:
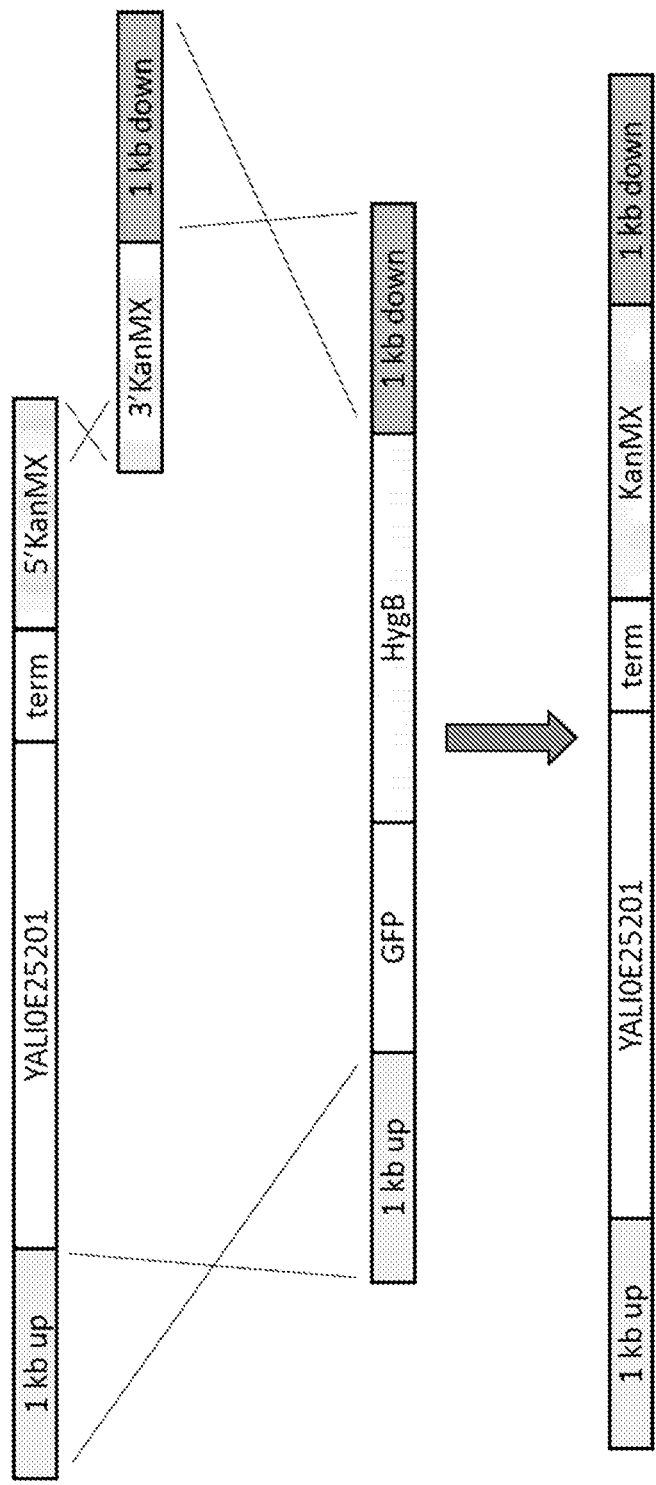
FIG. 2 depicts the strategy used to introduce the YALIOE25201 transporter or transporter variants introduced in strain STVP002.

The YALIOE25201 transporter or transporter variants were introduced in strain STVP002. Two DNA elements (a left and a right DNA element) were transformed to strain STVP002 according to the strategy depicted in FIG. 2. The left DNA element contained 1 kb of sequence identical to the 1 kb upstream of YALIOE25201, the transporter ORF, the YALIOE25201 terminator (300 bp) and part of a KanMX marker cassette. The right DNA element contained part of the KanMX marker cassette partially overlapping with a portion of the left DNA fragment and 1 kb of sequence identical to the 1 kb downstream of the YALIOE25201 terminator. Double cross-over of these DNA elements at the genomic location of YALIOE25201, where in strain STVP002 GFP and HygB were integrated, enabled the deletion of GFP and HygB, with the introduction of the transporter ORF and a functional KanMX marker cassette integrated in the genome. Expression of the transporter was hence under control of the native YALIOE25201 promoter and terminator (300 bp).

Transformants were selected on agar plates containing 400 μg/ml G418. Transformants were further selected for loss of fluorescence (loss of GFP).

Example 4. Extracellular Production of RebM in Strain STVP002 Expressing Transporter Variants To establish the effect of the variant transporter expression on RebM production, RebA production and total steviol glycosides production, the following experiment was performed. A 96-well half deep well plate containing 200 μl YEP with glucose per well was inoculated with colony material. For each transporter variant, three, four or five replicate cultures were inoculated except for the wild type YALIOE25201, which was performed in 240-fold. The plates were sealed with a breathable seal and incubated in an Infors incubator at 30° C., 80% humidity shaking at 750 rpm for 48 hours. 40 μl of pre-culture was used to inoculate 2.5 ml mineral medium (described in example 2). The plate was sealed with a breath seal and incubated in an Infors incubator at 30° C., 80% humidity shaking at 500 rpm for 120 hours. After growth, cells of the 24-well cultures were pelleted by centrifuging the plates at 1500 g for 10 minutes. After centrifugation supernatant was transferred and diluted in 33% acetonitrile and the steviol glycoside concentrations were determined using Liquid Chromatography with Mass Spectrometry (LC-MS).

Result parameters were normalized for the correction of between plate effects by subtracting control median of the corresponding plate. Subsequently, the overall control median of the original measurement was added to maintain the baseline of the original experiment. Outliers were detected using Grubbs' test and removed. Result parameters were then averaged over the remaining valid replicate wells. A one-tailed Student's t-test with non-equal variance was used to determine if a mutant was significantly (p-value <0.05) better than the control.

240 replicates of the STVP002 transformed with the wild type transporter sequence were analyzed for extracellular production. One of these was discarded as an outlier, resulting in 239 valid replicates. Triplicate, quadruplicate or quintuplicate replicates were analyzed for the transporter variant transformants. For the data of transformants with the variant transporters in table 5, all were derived from at least three replicate wells, and the majority s was derived from four or five valid replicate wells. For each transformant with variant transporter, the produced RebM, the ratio of the produced RebM over the produced RebA and the ratio of the produced RebM over the total production of steviol glycosides (including RebA, RebB, RebD, RebM, stevioside, steviolbioside, rubusoside, steviol-13-monoside) was compared to the transformant with the wild type sequence. A Student's t-test was performed to establish the significance of the improvement in RebM produced, in the ratio of produced RebM over produced RebA and the ratio of produced RebM over total steviol glycosides, for each transformant with a variant transporter vs the transformants with the wild type transporter.

TABLE 5

Concentration RebM, ratio of concentration RebM/concentration RebA produced and ratio of concentration RebM/concentration Total steviol glycosides (including RebA, RebB, RebD, RebM, stevioside, steviolbioside, rubusoside, steviol-13-monoside) produced in the supernatant of strain STVP002 transformed with transporter variants as indicated in each row. Values represent molar concentrations normalized for production in strain STVP002 transformed with wild type transporter YALI0E25201 (with amino acid sequence according to SEQ ID NO: 3) (first row in Table 5).

| aa Position | aa WT | aa substit. | RebM | p-value RebM | Ratio RebM/ RebA | p-value ratio RebM/ RebA | Ratio RebM/ Total SGs | p-value ratio RebM/ Total SGs |
|---|---|---|---|---|---|---|---|---|
| (WT) | n.a. | n.a | 100 | n.a. | 100 | n.a. | 100 | n.a. |
| 15 | S | A | 122 | 0.009 | 114 | 0.032 | 111 | 0.034 |
| 15 | S | V | 108 | 0.211 | 131 | 0.005 | 112 | 0.008 |
| 19 | S | G | 128 | 0.005 | 111 | 0.043 | 110 | 0.007 |
| 26 | S | Q | 112 | 0.029 | 117 | 0.022 | 111 | 0.011 |
| 26 | S | W | 124 | 0.002 | 146 | 0.008 | 126 | 0.007 |
| 29 | T | F | 117 | 0.022 | 129 | 0.004 | 118 | 0.001 |
| 31 | F | A | 131 | 0.000 | 122 | 0.002 | 117 | 0.002 |
| 31 | F | Y | 112 | 0.158 | 141 | 0.010 | 123 | 0.005 |
| 32 | T | N | 116 | 0.007 | 109 | 0.102 | 108 | 0.035 |
| 33 | G | I | 113 | 0.148 | 142 | 0.004 | 124 | 0.003 |
| 37 | P | G | 117 | 0.005 | 144 | 0.005 | 129 | 0.002 |
| 46 | S | T | 112 | 0.090 | 126 | <0.001 | 122 | 0.000 |
| 56 | K | T | 112 | 0.055 | 113 | 0.009 | 112 | 0.002 |
| 59 | W | L | 112 | 0.034 | 123 | 0.009 | 115 | 0.011 |
| 135 | L | C | 104 | 0.168 | 136 | 0.002 | 119 | 0.001 |
| 136 | N | Y | 110 | 0.009 | 119 | 0.000 | 116 | 0.000 |
| 145 | L | I | 105 | 0.035 | 104 | 0.128 | 106 | 0.005 |
| 148 | L | Q | 113 | 0.028 | 131 | 0.004 | 124 | 0.004 |
| 150 | A | L | 113 | 0.022 | 126 | 0.005 | 120 | 0.003 |
| 151 | L | G | 107 | 0.036 | 116 | 0.013 | 113 | 0.000 |
| 153 | K | L | 102 | 0.383 | 142 | 0.003 | 130 | 0.001 |
| 153 | K | P | 84 | 0.906 | 141 | 0.045 | 113 | 0.025 |
| 199 | L | T | 90 | 0.938 | 126 | 0.019 | 109 | 0.019 |
| 200 | A | Y | 117 | 0.040 | 116 | 0.049 | 116 | 0.033 |
| 204 | T | F | 112 | 0.071 | 126 | 0.001 | 122 | 0.001 |
| 206 | F | I | 110 | 0.143 | 127 | 0.022 | 121 | 0.012 |
| 207 | F | W | 108 | 0.000 | 112 | 0.008 | 110 | 0.015 |
| 210 | M | G | 101 | 0.408 | 120 | 0.033 | 112 | 0.004 |
| 210 | M | V | 92 | 0.804 | 130 | 0.001 | 110 | 0.058 |
| 211 | F | L | 96 | 0.747 | 127 | 0.000 | 110 | 0.047 |
| 262 | E | F | 106 | 0.199 | 118 | 0.016 | 111 | 0.052 |
| 262 | L | I | 102 | 0.360 | 120 | 0.015 | 114 | 0.020 |
| 267 | F | G | 110 | 0.132 | 152 | 0.006 | 130 | 0.000 |
| 267 | F | L | 98 | 0.599 | 129 | 0.011 | 116 | 0.003 |
| 268 | H | Q | 113 | 0.002 | 120 | 0.013 | 116 | 0.002 |
| 268 | H | S | 97 | 0.577 | 146 | 0.001 | 117 | 0.041 |
| 268 | H | T | 117 | 0.034 | 121 | 0.002 | 117 | 0.001 |
| 272 | I | G | 107 | 0.186 | 131 | 0.002 | 120 | 0.001 |
| 273 | F | Y | 106 | 0.047 | 144 | 0.001 | 126 | 0.000 |
| 276 | V | G | 107 | 0.186 | 128 | 0.001 | 120 | 0.001 |
| 277 | V | S | 112 | 0.020 | 121 | 0.008 | 114 | 0.002 |
| 278 | G | V | 114 | 0.016 | 156 | 0.001 | 132 | 0.000 |
| 281 | I | N | 111 | 0.070 | 125 | 0.006 | 120 | 0.003 |
| 282 | A | N | 125 | 0.007 | 153 | 0.002 | 133 | 0.001 |
| 283 | V | F | 98 | 0.622 | 111 | 0.044 | 107 | 0.044 |
| 284 | L | G | 98 | 0.580 | 148 | 0.002 | 128 | 0.001 |
| 284 | L | S | 115 | 0.063 | 157 | 0.001 | 135 | 0.000 |
| 292 | A | T | 107 | 0.164 | 115 | 0.001 | 110 | 0.001 |
| 294 | V | T | 107 | 0.111 | 119 | 0.006 | 114 | 0.001 |
| 296 | I | T | 107 | 0.071 | 125 | 0.008 | 117 | 0.003 |
| 297 | A | S | 106 | 0.122 | 128 | 0.001 | 119 | 0.002 |

TABLE 5-continued

Concentration RebM, ratio of concentration RebM/concentration RebA produced
and ratio of concentration RebM/concentration Total steviol glycosides
(including RebA, RebB, RebD, RebM, stevioside, steviolbioside, rubusoside,
steviol-13-monoside) produced in the supernatant of strain STVP002 transformed
with transporter variants as indicated in each row. Values represent
molar concentrations normalized for production in strain STVP002 transformed
with wild type transporter YALI0E25201 (with amino acid sequence according
to SEQ ID NO: 3) (first row in Table 5).

| aa Position | aa WT | aa substit. | RebM | p-value RebM | Ratio RebM/ RebA | p-value ratio RebM/ RebA | Ratio RebM/ Total SGs | p-value ratio RebM/ Total SGs |
|---|---|---|---|---|---|---|---|---|
| 298 | T | K | 117 | 0.059 | 156 | 0.002 | 131 | 0.004 |
| 298 | T | L | 118 | 0.007 | 137 | 0.003 | 125 | 0.000 |
| 299 | M | L | 110 | 0.072 | 115 | <0.001 | 113 | 0.000 |
| 299 | M | T | 126 | 0.032 | 147 | 0.016 | 129 | 0.012 |
| 299 | M | V | 113 | 0.001 | 152 | 0.002 | 130 | 0.002 |
| 300 | I | M | 109 | 0.035 | 117 | 0.082 | 108 | 0.071 |
| 302 | L | F | 112 | 0.089 | 136 | 0.019 | 120 | 0.029 |
| 302 | L | Q | 111 | 0.183 | 149 | 0.016 | 122 | 0.003 |
| 302 | L | S | 115 | 0.031 | 125 | 0.028 | 120 | 0.019 |
| 302 | L | T | 117 | 0.039 | 130 | 0.010 | 120 | 0.000 |
| 302 | L | V | 125 | 0.003 | 158 | 0.000 | 136 | 0.000 |
| 303 | I | M | 114 | 0.030 | 107 | 0.208 | 107 | 0.081 |
| 303 | I | R | 114 | 0.000 | 153 | 0.002 | 133 | 0.000 |
| 303 | I | T | 97 | 0.748 | 110 | 0.015 | 104 | 0.014 |
| 306 | V | F | 120 | 0.036 | 148 | 0.007 | 127 | 0.003 |
| 306 | V | I | 83 | 0.998 | 145 | 0.004 | 113 | 0.020 |
| 306 | V | M | 103 | 0.407 | 198 | <0.001 | 141 | 0.000 |
| 306 | V | S | 124 | 0.003 | 149 | 0.001 | 132 | 0.001 |
| 307 | A | I | 118 | 0.025 | 143 | 0.000 | 129 | <0.001 |
| 307 | A | L | 101 | 0.426 | 136 | 0.001 | 122 | 0.001 |
| 309 | I | M | 113 | 0.059 | 141 | 0.005 | 124 | 0.005 |
| 310 | T | C | 104 | 0.307 | 131 | 0.006 | 116 | 0.002 |
| 310 | T | N | 104 | 0.275 | 121 | 0.001 | 116 | 0.001 |
| 311 | I | T | 102 | 0.331 | 126 | 0.001 | 117 | 0.000 |
| 311 | I | W | 115 | 0.004 | 122 | 0.016 | 119 | 0.007 |
| 375 | A | F | 122 | 0.012 | 194 | <0.001 | 153 | <0.001 |
| 375 | A | H | 102 | 0.311 | 128 | 0.028 | 116 | 0.017 |
| 375 | A | K | 117 | 0.083 | 135 | 0.004 | 123 | 0.007 |
| 375 | A | L | 104 | 0.369 | 136 | 0.003 | 122 | 0.004 |
| 375 | A | N | 111 | 0.050 | 140 | 0.018 | 124 | 0.016 |
| 376 | I | W | 127 | 0.000 | 207 | <0.001 | 157 | <0.001 |
| 378 | M | I | 121 | <0.001 | 133 | 0.000 | 124 | 0.000 |
| 378 | M | N | 114 | <0.001 | 150 | <0.001 | 134 | <0.001 |
| 378 | M | T | 133 | 0.001 | 152 | 0.000 | 137 | 0.000 |
| 378 | M | V | 122 | 0.009 | 127 | 0.015 | 122 | 0.008 |
| 379 | F | Y | 130 | 0.003 | 150 | 0.001 | 135 | 0.000 |
| 380 | Q | E | 111 | 0.025 | 142 | 0.000 | 130 | <0.001 |
| 380 | Q | R | 116 | 0.013 | 136 | 0.016 | 120 | 0.009 |
| 382 | L | S | 120 | 0.017 | 129 | 0.004 | 123 | 0.001 |
| 382 | L | T | 120 | 0.084 | 147 | 0.001 | 134 | 0.001 |
| 382 | L | W | 119 | 0.003 | 138 | 0.001 | 124 | 0.001 |
| 384 | I | G | 131 | 0.002 | 187 | 0.000 | 152 | 0.000 |
| 384 | I | N | 136 | 0.000 | 175 | <0.001 | 148 | <0.001 |
| 384 | I | S | 141 | 0.010 | 173 | 0.001 | 147 | 0.000 |
| 384 | I | T | 149 | 0.001 | 178 | 0.001 | 152 | 0.000 |
| 386 | A | I | 130 | 0.001 | 150 | 0.001 | 135 | 0.001 |
| 386 | A | L | 133 | 0.017 | 177 | 0.000 | 148 | <0.001 |
| 387 | G | A | 102 | 0.313 | 131 | 0.043 | 112 | 0.024 |
| 389 | L | M | 118 | 0.002 | 112 | 0.067 | 112 | 0.024 |
| 408 | S | G | 111 | 0.055 | 124 | 0.001 | 117 | <0.001 |
| 410 | L | A | 112 | 0.002 | 124 | 0.006 | 116 | 0.009 |
| 411 | T | F | 111 | 0.012 | 134 | 0.009 | 124 | 0.006 |
| 411 | T | G | 119 | 0.017 | 159 | <0.001 | 132 | 0.001 |
| 413 | F | I | 114 | 0.002 | 128 | 0.002 | 116 | 0.002 |
| 414 | N | F | 104 | 0.382 | 147 | 0.001 | 120 | 0.003 |
| 414 | N | G | 134 | 0.011 | 147 | 0.002 | 130 | 0.001 |
| 414 | N | R | 110 | 0.029 | 165 | 0.001 | 138 | 0.000 |
| 415 | L | V | 119 | 0.060 | 142 | 0.003 | 128 | 0.003 |
| 416 | L | W | 125 | 0.013 | 138 | 0.001 | 127 | 0.000 |
| 417 | L | A | 125 | 0.014 | 119 | 0.011 | 116 | 0.008 |
| 417 | L | S | 132 | 0.001 | 154 | 0.001 | 134 | 0.000 |
| 417 | L | T | 121 | 0.001 | 135 | 0.001 | 123 | 0.000 |
| 417 | L | W | 121 | 0.052 | 162 | 0.000 | 136 | 0.000 |
| 419 | A | G | 112 | 0.200 | 145 | 0.001 | 125 | 0.003 |
| 419 | A | M | 124 | 0.003 | 128 | 0.003 | 120 | 0.002 |

TABLE 5-continued

Concentration RebM, ratio of concentration RebM/concentration RebA produced and ratio of concentration RebM/concentration Total steviol glycosides (including RebA, RebB, RebD, RebM, stevioside, steviolbioside, rubusoside, steviol-13-monoside) produced in the supernatant of strain STVP002 transformed with transporter variants as indicated in each row. Values represent molar concentrations normalized for production in strain STVP002 transformed with wild type transporter YALI0E25201 (with amino acid sequence according to SEQ ID NO: 3) (first row in Table 5).

| aa Position | aa WT | aa substit. | RebM | p-value RebM | Ratio RebM/ RebA | p-value ratio RebM/ RebA | Ratio RebM/ Total SGs | p-value ratio RebM/ Total SGs |
|---|---|---|---|---|---|---|---|---|
| 420 | L | G | 143 | 0.000 | 196 | <0.001 | 155 | <0.001 |
| 420 | L | S | 113 | 0.016 | 156 | 0.006 | 132 | 0.005 |
| 421 | A | F | 126 | 0.003 | 157 | 0.000 | 133 | 0.000 |
| 421 | A | I | 110 | 0.139 | 151 | 0.001 | 131 | 0.001 |
| 422 | V | M | 124 | 0.006 | 125 | 0.003 | 117 | 0.007 |
| 423 | L | A | 104 | 0.190 | 112 | 0.006 | 107 | <0.001 |
| 423 | L | Q | 101 | 0.463 | 159 | 0.000 | 126 | 0.001 |
| 424 | P | L | 111 | 0.013 | 228 | 0.000 | 152 | <0.001 |
| 424 | P | S | 118 | 0.000 | 120 | 0.030 | 116 | 0.004 |
| 425 | Q | A | 134 | 0.003 | 147 | 0.002 | 134 | 0.001 |
| 425 | Q | H | 125 | 0.002 | 163 | 0.006 | 134 | 0.000 |
| 425 | Q | L | 125 | 0.018 | 184 | 0.002 | 143 | 0.001 |
| 425 | Q | M | 131 | 0.003 | 151 | 0.002 | 131 | 0.001 |
| 425 | Q | V | 121 | 0.014 | 118 | 0.013 | 112 | 0.012 |
| 427 | L | M | 104 | 0.178 | 120 | 0.007 | 114 | 0.007 |
| 428 | Q | M | 111 | 0.032 | 120 | 0.055 | 114 | 0.008 |
| 429 | A | M | 109 | 0.095 | 112 | 0.001 | 110 | 0.005 |
| 429 | A | S | 130 | 0.002 | 201 | 0.000 | 149 | <0.001 |
| 853 | M | V | 126 | 0.002 | 117 | 0.013 | 114 | 0.004 |
| 854 | I | G | 121 | 0.040 | 137 | 0.009 | 126 | 0.006 |
| 854 | I | S | 110 | 0.022 | 115 | 0.000 | 109 | 0.000 |
| 857 | S | P | 120 | 0.099 | 137 | 0.001 | 123 | 0.007 |
| 859 | I | A | 89 | 0.998 | 132 | 0.018 | 107 | 0.029 |
| 859 | I | P | 123 | 0.009 | 147 | <0.001 | 131 | 0.000 |
| 859 | I | S | 106 | 0.060 | 129 | 0.026 | 120 | 0.016 |
| 862 | A | T | 100 | 0.523 | 119 | 0.007 | 117 | 0.002 |
| 864 | L | A | 125 | 0.001 | 128 | 0.028 | 123 | 0.014 |
| 869 | S | V | 95 | 0.743 | 128 | 0.017 | 114 | 0.004 |
| 890 | I | P | 132 | 0.000 | 186 | 0.000 | 142 | 0.000 |
| 891 | Y | T | 126 | 0.008 | 185 | 0.000 | 144 | <0.001 |
| 892 | I | V | 112 | 0.086 | 126 | 0.013 | 120 | 0.005 |
| 894 | L | Q | 114 | 0.036 | 170 | 0.001 | 127 | 0.001 |
| 894 | L | Y | 116 | 0.023 | 120 | 0.013 | 113 | 0.013 |
| 903 | A | N | 116 | 0.040 | 197 | 0.001 | 135 | 0.000 |
| 906 | M | V | 140 | 0.002 | 157 | 0.001 | 137 | 0.000 |
| 968 | F | Q | 123 | 0.123 | 206 | 0.003 | 159 | 0.002 |
| 972 | A | Q | 106 | 0.170 | 208 | 0.003 | 132 | 0.001 |
| 974 | F | Q | 121 | 0.015 | 145 | 0.002 | 131 | 0.001 |
| 977 | F | A | 143 | 0.002 | 180 | 0.001 | 144 | <0.001 |
| 977 | F | Q | 134 | 0.004 | 191 | <0.001 | 150 | <0.001 |
| 996 | F | Y | 116 | 0.111 | 129 | 0.042 | 122 | 0.043 |
| 998 | F | A | 130 | 0.003 | 154 | 0.001 | 134 | 0.001 |
| 998 | F | G | 119 | 0.004 | 143 | 0.001 | 128 | 0.002 |
| 999 | Y | N | 124 | 0.020 | 126 | 0.016 | 119 | 0.010 |
| 999 | Y | T | 108 | 0.142 | 127 | 0.039 | 121 | 0.025 |
| 1001 | S | Y | 127 | 0.017 | 147 | 0.012 | 130 | 0.015 |
| 1003 | G | I | 127 | 0.041 | 125 | 0.025 | 119 | 0.013 |
| 1004 | Y | T | 130 | 0.001 | 135 | 0.001 | 123 | 0.000 |
| 1010 | R | T | 109 | 0.030 | 114 | 0.022 | 111 | 0.008 |
| 1063 | L | I | 114 | 0.023 | 146 | 0.001 | 130 | 0.002 |
| 1075 | L | S | 114 | 0.015 | 158 | 0.000 | 132 | 0.001 |
| 1076 | D | G | 106 | 0.093 | 226 | <0.001 | 151 | 0.000 |
| 1107 | S | Y | 129 | 0.029 | 220 | 0.000 | 155 | 0.001 |
| 1108 | A | K | 111 | 0.008 | 218 | 0.000 | 168 | 0.000 |
| 1112 | I | N | 132 | 0.004 | 234 | <0.001 | 159 | 0.000 |
| 1115 | V | G | 138 | 0.001 | 174 | 0.000 | 149 | 0.000 |
| 1118 | M | A | 121 | 0.029 | 208 | 0.003 | 148 | <0.001 |
| 1118 | M | F | 103 | 0.307 | 173 | 0.000 | 135 | 0.001 |
| 1118 | M | W | 110 | 0.065 | 142 | 0.004 | 132 | 0.002 |
| 1120 | A | M | 124 | 0.001 | 188 | 0.000 | 154 | 0.000 |
| 1123 | V | P | 119 | 0.023 | 179 | 0.000 | 144 | <0.001 |
| 1076 | D | A | 114 | 0.024 | 179 | 0.000 | 143 | 0.000 |
| 1108 | A | Q | 118 | 0.014 | 152 | 0.000 | 133 | 0.000 |
| 1111, 1179 | F, D | K, N | 127 | 0.007 | 231 | <0.001 | 167 | 0.000 |
| 141, 107 | W, H | K, R | 110 | <0.001 | 125 | 0.009 | 120 | 0.003 |

TABLE 5-continued

Concentration RebM, ratio of concentration RebM/concentration RebA produced and ratio of concentration RebM/concentration Total steviol glycosides (including RebA, RebB, RebD, RebM, stevioside, steviolbioside, rubusoside, steviol-13-monoside) produced in the supernatant of strain STVP002 transformed with transporter variants as indicated in each row. Values represent molar concentrations normalized for production in strain STVP002 transformed with wild type transporter YALI0E25201 (with amino acid sequence according to SEQ ID NO: 3) (first row in Table 5).

| aa Position | aa WT | aa substit. | RebM | p-value RebM | Ratio RebM/ RebA | p-value ratio RebM/ RebA | Ratio RebM/ Total SGs | p-value ratio RebM/ Total SGs |
|---|---|---|---|---|---|---|---|---|
| 382, 322 | L, K | G, E | 137 | <0.001 | 200 | 0.001 | 157 | 0.000 |
| 892, 986 | I, Y | F, H | 120 | 0.001 | 144 | 0.000 | 127 | <0.001 |
| 969, 1060 | G, A | N, T | 166 | 0.001 | 264 | <0.001 | 176 | <0.001 |

The amino acid position in the first column (with header "aa Position) in Table 5 refers to the amino acid position in the variant with reference to SEQ ID NO: 3. In the second column ("aa WT") the amino acid present in the wild type at the position indicated in the first column. In the third column ("aa subtit.") the amino acid substitution is given, hence the variant amino acid of said amino acid position is given. In case there are more than one position listed in the first and second column, the first amino acid substitution (in the third column) correspond to the first position (in the first and second column), the second amino acid substitution to the second position, etc. The fourth column ("RebM") indicates the molar concentration of RebM measured in a recombinant cell expressing a variant with the indicated amino acid substitution (said molar concentration normalized if compared to a recombinant cell expressing the parent polypeptide according to SEQ ID NO: 3 which is set to 100). The fifth column ("p-value RebM") indicates the p-value calculated for the molar concentration of RebM. The sixth ("Ratio RebM/RebA) and the seventh column ("p-value ratio RebM/RebA") indicate, respectively, the ratio of the molar concentration of RebM over RebA (said ratio normalized if compared to the same ratio measured, under the same conditions, in a recombinant cell expressing the parent polypeptide according to SEQ ID NO: 3, which is set to 100) and the corresponding p-value. The eight ("Ratio RebM/Total SGs") and the ninth column ("p-value ratio RebM/Total SGs") indicate, respectively, the ratio of the molar concentration of RebM over the total steviol glycosides (said ratio normalized if compared to the same ratio measured, under the same conditions, in a recombinant cell expressing the parent polypeptide according to SEQ ID NO: 3, which is set to 100). The results in Table 5 illustrate that surprisingly transformants with transporter variants listed in Table 5 result in higher extracellular production of RebM and/or a higher extracellular production of RebM compared to RebA, and/or a higher extracellular production of RebM compared to total steviol glycosides. In the majority of the transporter variants listed in Table 5, all these three criteria are improved over the wild type sequence.

Variants in certain stretches of the protein result in particularly high frequency of improvements with a large magnitude, e.g. in amino acid positions 375-386, 411-425, 906-1180.

Example 5. Extracellular Production of RebM in Strain STVP002 Expressing Transporter Variants with Combinations of Mutations To establish the effect of the variant transporter expression on extracellular RebM, RebA and total steviol glycosides production, a production test was performed. A 96-well half deep well plate containing 200 µl YEP with glucose per well was inoculated with colony material. For each transporter variant, twelve replicate cultures were inoculated except for the wild type YALIOE25201, which was performed in 240-fold. The plates were sealed with a breathable seal and incubated in an Infors incubator at 30° C., 80% humidity shaking at 750 rpm for 48 hours. 40 µl of pre-culture was used to inoculate 2.5 ml mineral medium (Verduyn, Yeast vol 8, 501-517 (1992) with ureum instead of ammonium sulfate as nitrogen source), pH 6 with glucose as carbon source. The plate was sealed with a breath seal and incubated in an Infors incubator at 30° C., 80% humidity shaking at 500 rpm for 120 hours. After growth, cells of the 24-well cultures were pelleted by centrifuging the plates at 1500 g for 10 minutes. After centrifugation supernatant was transferred and diluted in 33% acetonitrile and the steviolglycoside concentrations were determined using Liquid Chromatography with Mass Spectrometry (LC-MS).

Result parameters were normalized for the correction of between plate effects by subtracting control median of the corresponding plate. Subsequently, the overall control median of the original measurement was added to maintain the baseline of the original experiment. Outliers were detected using Grubbs' test and removed. Result parameters were then averaged over the remaining valid replicate wells. A one-tailed Student's t-test with non-equal variance was used to determine if a mutant was significantly (p-value <0.05) better than the control.

240 replicates of the STVP002 transformed with the wild type transporter sequence were analyzed for extracellular production. None of these was discarded as an outlier. Twelve replicates were analyzed for the transporter variant transformants. For the data of transformants with the variant transporters in table 6, all were derived from at least 8 valid replicate wells, and the majority was derived from 12 valid replicate wells. For each transformant with variant transporter, the produced RebM, the ratio of the produced RebM over the produced RebA and the ratio of the produced RebM over the total production of steviol glycosides (including RebA, RebB, RebD, RebM, stevioside, steviolbioside, rubusoside, steviol-13-monoside) was compared to the transformant with the wild type sequence. A Student's t-test was performed to establish the significance of the improvement in RebM produced, in the ratio of produced RebM over produced RebA and the ratio of produced RebM over total steviol glycosides, for each transformant with a variant transporter vs the transformants with the wild type transporter.

TABLE 6

Concentration RebM, ratio of concentration RebM/concentration RebA produced and ratio of concentration RebM/concentration Total steviol glycosides (including RebA, RebB, RebD, RebM, stevioside, steviolbioside, rubusoside, steviol-13-monoside) produced in the supernatant of strain STVP002 transformed with transporters. Values represent molar concentrations normalized for production in strain STVP002 transformed with wild type transporter YALI0E25201 (first entry in Table 6).

| aa Position | aa WT | Aa substitution | RebM | p-value RebM | Ratio RebM/ RebA | p-value ratio RebM/ RebA | Ratio RebM/ Total SGs | p-value ratio RebM/ Total SGs |
|---|---|---|---|---|---|---|---|---|
| (WT) | n.a. | n.a | 100 | n.a | 100 | n.a | 100 | n.a |
| 375, 969, 1060 | A, G, A | F, N, T | 91 | 0.918 | 230 | <0.001 | 148 | <0.001 |
| 375, 977 | A, F | F, A | 119 | <0.001 | 186 | <0.001 | 146 | <0.001 |
| 375, 1107 | A, S | F, Y | 121 | <0.001 | 204 | <0.001 | 151 | <0.001 |
| 376, 969, 1060 | I, G, A | W, N, T | 89 | 0.928 | 244 | <0.001 | 152 | <0.001 |
| 376, 977 | I, F | W, A | 122 | <0.001 | 205 | <0.001 | 158 | <0.001 |
| 376, 1107 | I, S | W, Y | 77 | 0.997 | 182 | <0.001 | 128 | <0.001 |
| 376, 1112 | I, I | W, N | 89 | 0.976 | 147 | 0.008 | 119 | 0.003 |
| 382, 322, 891 | L, K, Y | G, E, T | 122 | <0.001 | 221 | <0.001 | 161 | <0.001 |
| 382, 322, 890 | L, K, I | G, E, P | 118 | 0.014 | 164 | 0.002 | 139 | 0.002 |
| 382, 322, 969, 1060 | L, K, G, A | G, E, N, T | 112 | 0.009 | 193 | <0.001 | 148 | <0.001 |
| 382, 322, 977 | L, K, F | G, E, A | 110 | 0.121 | 202 | <0.001 | 150 | <0.001 |
| 382, 322, 977 | L, K, F | G, E, Q | 118 | 0.018 | 240 | <0.001 | 163 | <0.001 |
| 382, 322, 1107 | L, K, S | G, E, Y | 113 | 0.049 | 193 | <0.001 | 151 | <0.001 |
| 382, 322, 1111, 1179 | L, K, F, D | G, E, K, N | 131 | 0.001 | 235 | <0.001 | 162 | <0.001 |
| 382, 322, 1112 | L, K, I | G, E, N | 110 | 0.183 | 266 | <0.001 | 164 | <0.001 |
| 382, 322, 1115 | L, K, V | G, E, G | 121 | 0.003 | 223 | <0.001 | 164 | <0.001 |
| 382, 322, 1118 | L, K, M | G, E, A | 137 | <0.001 | 182 | <0.001 | 152 | <0.001 |
| 378, 969, 1060 | M, G, A | T, N, T | 140 | <0.001 | 317 | <0.001 | 195 | <0.001 |
| 378, 977 | M, F | T, A | 117 | 0.002 | 186 | <0.001 | 148 | <0.001 |
| 378, 1107 | M, S | T, Y | 116 | 0.099 | 229 | <0.001 | 154 | <0.001 |
| 378, 1112 | M, I | T, N | 103 | 0.413 | 199 | <0.001 | 136 | 0.006 |
| 384, 969, 1060 | I, G, A | G, N, T | 141 | <0.001 | 332 | <0.001 | 194 | <0.001 |
| 384, 977 | I, F | G, A | 135 | <0.001 | 230 | <0.001 | 170 | <0.001 |
| 384, 1107 | I, S | G, Y | 120 | 0.025 | 255 | <0.001 | 169 | <0.001 |
| 384, 1112 | I, I | G, N | 117 | 0.032 | 272 | <0.001 | 174 | <0.001 |
| 384, 969, 1060 | I, G, A | N, N, T | 143 | <0.001 | 256 | <0.001 | 174 | <0.001 |
| 384, 977 | I, F | N, A | 106 | 0.278 | 211 | <0.001 | 148 | <0.001 |
| 384, 1107 | I, S | N, Y | 120 | 0.034 | 191 | 0.001 | 145 | 0.003 |
| 384, 1112 | I, I | N, N | 103 | 0.364 | 191 | 0.001 | 137 | 0.005 |
| 384, 891 | I, Y | S, T | 93 | 0.758 | 163 | 0.010 | 123 | 0.037 |
| 384, 89 | I, A | S, P | 117 | 0.013 | 206 | <0.001 | 158 | <0.001 |
| 384, 969, 1060 | I, G, A | S, N, T | 109 | 0.209 | 259 | <0.001 | 159 | <0.001 |
| 384, 977 | I, F | S, A | 116 | 0.003 | 172 | 0.001 | 139 | 0.001 |
| 384, 977 | I, F | S, Q | 89 | 0.838 | 195 | 0.001 | 133 | 0.009 |
| 384, 1107 | I, S | S, Y | 112 | 0.007 | 198 | <0.001 | 151 | <0.001 |
| 384, 1111, 1179 | I, F, D | S, K, N | 117 | 0.122 | 244 | <0.001 | 161 | <0.001 |
| 384, 1112 | I, I | S, N | 100 | 0.491 | 229 | <0.001 | 146 | <0.001 |
| 384, 1115 | I, V | S, G | 135 | 0.016 | 189 | <0.001 | 150 | <0.001 |
| 384, 1118 | I, M | S, A | 160 | <0.001 | 258 | <0.001 | 180 | <0.001 |
| 386, 969, 1060 | A, G, A | L, N, T | 94 | 0.739 | 205 | <0.001 | 141 | <0.001 |
| 386, 977 | A, F | L, A | 89 | 0.933 | 188 | <0.001 | 128 | <0.001 |
| 386, 1107 | A, S | L, Y | 110 | 0.026 | 176 | <0.001 | 138 | <0.001 |
| 386, 1112 | A, I | L, N | 123 | 0.001 | 181 | <0.001 | 145 | <0.001 |

TABLE 6-continued

Concentration RebM, ratio of concentration RebM/concentration RebA produced and ratio of concentration RebM/concentration Total steviol glycosides (including RebA, RebB, RebD, RebM, stevioside, steviolbioside, rubusoside, steviol-13-monoside) produced in the supernatant of strain STVP002 transformed with transporters. Values represent molar concentrations normalized for production in strain STVP002 transformed with wild type transporter YALI0E25201 (first entry in Table 6).

| aa Position | aa WT | Aa substitution | RebM | p-value RebM | Ratio RebM/ RebA | p-value ratio RebM/ RebA | Ratio RebM/ Total SGs | p-value ratio RebM/ Total SGs |
|---|---|---|---|---|---|---|---|---|
| 384, 89 | I, A | T, P | 110 | 0.116 | 137 | 0.020 | 119 | 0.034 |
| 384, 969, 1060 | I, G, A | T, N, T | 138 | 0.002 | 254 | <0.001 | 172 | <0.001 |
| 384, 977 | I, F | T, A | 105 | 0.303 | 169 | 0.001 | 131 | 0.007 |
| 384, 977 | I, F | T, Q | 122 | <0.001 | 189 | <0.001 | 150 | <0.001 |
| 384, 1107 | I, S | T, Y | 139 | <0.001 | 213 | <0.001 | 156 | <0.001 |
| 384, 1111, 1179 | I, F, D | T, K, N | 121 | <0.001 | 288 | <0.001 | 182 | <0.001 |
| 384, 1112 | I, I | T, N | 124 | <0.001 | 176 | <0.001 | 141 | <0.001 |
| 384, 1115 | I, V | T, G | 118 | 0.038 | 193 | <0.001 | 154 | <0.001 |
| 384, 1118 | I, M | T, A | 135 | <0.001 | 192 | <0.001 | 155 | <0.001 |
| 425, 969, 1060 | Q, G, A | L, N, T | 100 | 0.493 | 221 | <0.001 | 141 | 0.002 |
| 425, 1107 | Q, S | L, Y | 113 | 0.134 | 186 | 0.004 | 140 | 0.017 |
| 425, 1112 | Q, I | L, N | 113 | 0.011 | 200 | <0.001 | 151 | <0.001 |
| 425, 969, 1060 | Q, G, A | A, N, T | 140 | 0.009 | 205 | 0.005 | 148 | 0.008 |
| 425, 1107 | Q, S | A, Y | 143 | <0.001 | 226 | 0.001 | 160 | <0.001 |
| 425, 1112 | Q, I | A, N | 104 | 0.274 | 164 | 0.002 | 130 | 0.009 |
| 425, 969, 1060 | Q, G, A | M, N, T | 113 | 0.199 | 222 | 0.001 | 142 | 0.013 |
| 425, 1107 | Q, S | M, Y | 131 | <0.001 | 195 | <0.001 | 150 | <0.001 |
| 425, 1112 | Q, I | M, N | 103 | 0.299 | 201 | <0.001 | 144 | <0.001 |
| 421, 969, 1060 | A, G, A | F, N, T | 127 | 0.013 | 215 | 0.002 | 152 | 0.003 |
| 421, 977 | A, F | F, A | 123 | 0.003 | 213 | <0.001 | 158 | <0.001 |
| 421, 1112 | A, I | F, N | 91 | 0.868 | 188 | 0.001 | 132 | 0.010 |
| 420, 891 | L, Y | G, T | 99 | 0.534 | 203 | <0.001 | 144 | <0.001 |
| 420, 89 | L, A | G, P | 91 | 0.848 | 249 | <0.001 | 153 | <0.001 |
| 420, 969, 1060 | L, G, A | G, N, T | 85 | 0.977 | 302 | <0.001 | 164 | <0.001 |
| 420, 977 | L, F | G, A | 119 | 0.025 | 240 | <0.001 | 164 | <0.001 |
| 420, 977 | L, F | G, Q | 84 | 0.974 | 201 | <0.001 | 135 | <0.001 |
| 420, 1107 | L, S | G, Y | 128 | <0.001 | 210 | <0.001 | 154 | <0.001 |
| 420, 1111, 1179 | L, F, D | G, K, N | 115 | 0.071 | 226 | <0.001 | 155 | <0.001 |
| 420, 1112 | L, I | G, N | 130 | 0.016 | 203 | <0.001 | 146 | <0.001 |
| 420, 1115 | L, V | G, G | 123 | <0.001 | 202 | <0.001 | 154 | <0.001 |
| 420, 1118 | L, M | G, A | 95 | 0.648 | 193 | 0.005 | 132 | 0.031 |
| 429, 89 | A, A | S, P | 124 | 0.001 | 135 | 0.001 | 125 | 0.001 |
| 429, 969, 1060 | A, G, A | S, N, T | 111 | 0.229 | 209 | 0.001 | 143 | 0.008 |
| 429, 1107 | A, S | S, Y | 98 | 0.595 | 155 | 0.009 | 123 | 0.037 |
| 429, 1111, 1179 | A, F, D | S, K, N | 124 | 0.001 | 234 | <0.001 | 168 | <0.001 |
| 429, 1112 | A, I | S, N | 125 | 0.001 | 189 | <0.001 | 149 | <0.001 |
| 429, 1115 | A, V | S, G | 120 | <0.001 | 157 | <0.001 | 134 | <0.001 |
| 429, 1118 | A, M | S, A | 145 | <0.001 | 166 | <0.001 | 145 | <0.001 |
| 424, 969, 1060 | P, G, A | L, N, T | 57 | 1.000 | 185 | <0.001 | 115 | 0.052 |
| 424, 977 | P, F | L, A | 112 | 0.060 | 316 | <0.001 | 179 | <0.001 |
| 424, 1107 | P, S | L, Y | 94 | 0.694 | 351 | <0.001 | 168 | <0.001 |
| 424, 1112 | P, I | L, N | 58 | 1.000 | 276 | <0.001 | 131 | <0.001 |
| 386, 969, 1060 | A, G, A | I, N, T | 111 | 0.275 | 247 | <0.001 | 149 | 0.001 |
| 386, 1107 | A, S | I, Y | 108 | 0.034 | 165 | 0.002 | 133 | 0.002 |
| 386, 1112 | A, I | I, N | 125 | <0.001 | 209 | <0.001 | 158 | <0.001 |

The results in Table 6 illustrate that surprisingly transformants with transporter variants listed in Table 6 result in higher production of RebM and/or a higher production of RebM compared to RebA, and/or a higher production of RebM compared to total steviol glycosides. In the majority of the transporter variants listed in Table 5, at least two of these three criteria are improved over the wild type sequence.

A few variants seem to have a higher specificity of RebM transport over RebA transport, but lower overall activity. The transporter variants described in this example are expressed using the native YALI025201 promotor. Upon expressing the transporter with a stronger promotor, it is expected that the overall activity will be restored, or even exceeding the levels seen in the reference strain. Hence by using higher expression, one may retain the specificity (e.g. RebM transport over RebA transport) yet increase the overall transport activity of the cell.

Example 6. Extracellular Production of RebM in Strain STVP002 Expressing Transporter Variants with Single Mutations and Combinations of Mutations To establish the effect of the variant transporter expression on RebM, RebA and total steviol glycosides production, a production test was performed. A 96-well half deep well plate containing 200 µl YEP with glucose per well was inoculated with colony material. For each transporter variant, twelve replicate cultures were inoculated when the number of transformants permitted, except for the wild type YALI0E25201, which was performed in 272-fold. The plates were sealed with a breathable seal and incubated in an Infors incubator at 30° C., 80% humidity shaking at 750 rpm for 48 hours. 40 µl of pre-culture was used to inoculate 2.5 ml mineral medium (Verduyn, Yeast vol 8, 501-517 (1992) with ureum instead of ammonium sulfate as nitrogen source), pH 6 with glucose as carbon source. The plate was sealed with a breath seal and incubated in an Infors incubator at 30° C., 80% humidity shaking at 500 rpm for 120 hours. After growth, cells of the 24-well cultures were pelleted by centrifuging the plates at 1500 g for 10 minutes. After centrifugation supernatant was transferred and diluted in 33% acetonitrile and the steviolglycoside concentrations were determined using Liquid Chromatography with Mass Spectrometry (LC-MS).

Result parameters were normalized for the correction of between plate effects by subtracting control median of the corresponding plate. Subsequently, the overall control median of the original measurement was added to maintain the baseline of the original experiment. Outliers were detected using Grubbs' test and removed. Result parameters were then averaged over the remaining valid replicate wells. A one-tailed Student's t-test with non-equal variance was used to determine if a mutant was significantly (p-value <0.05) better than the control.

272 replicates of the STVP002 transformed with the wild type transporter sequence were analyzed for extracellular production. 31 of these were discarded as an outlier. Twelve replicates were analyzed for the transporter variant transformants, when the number of transformants permitted. For some designs, less than 12 were available. For the data of transformants with the variant transporters in table 7, all were derived from at least four valid replicate wells and the majority was derived from at least 10 valid replicate wells. For each transformant with variant transporter, the produced RebM, the ratio of the produced RebM over the produced RebA and the ratio of the produced RebM over the total production of steviol glycosides (including RebA, RebB, RebD, RebM, stevioside, steviolbioside, rubusoside, steviol-13-monoside) was compared to the transformant with the wild type sequence. A Student's t-test was performed to establish the significance of the improvement in RebM produced, in the ratio of produced RebM over produced RebA and the ratio of produced RebM over total steviol glycosides, for each transformant with a variant transporter vs the transformants with the wild type transporter.

TABLE 7

Concentration RebM, ratio of concentration RebM/concentration RebA produced and ratio of concentration RebM/concentration Total steviol glycosides (including RebA, RebB, RebD, RebM, stevioside, steviolbioside, rubusoside, steviol-13-monoside) produced in the supernatant of strain STVP002 transformed with transporters. Values represent molar concentrations normalized for production in strain STVP002 transformed with wild type transporter YALI0E25201, (first entry in Table 7).

| Position | aa WT | aa substitution | RebM | p-value RebM | Ratio RebM/ RebA | p-value ratio RebM/ RebA | Ratio RebM/ Total SGs | p-value ratio RebM/ Total SGs |
|---|---|---|---|---|---|---|---|---|
| (WT) | n.a. | n.a | 100 | n.a | 100 | n.a | 100 | n.a |
| 375, 1111, 1179 | A, F, D | F, K, N | 90 | 1.00 | 379 | <0.001 | 173 | <0.001 |
| 376, 1111, 1179 | I, F, D | W, K, N | 59 | 1.00 | 188 | <0.001 | 127 | <0.001 |
| 382, 322, 384 | L, K, I | G, E, S | 85 | 1.00 | 223 | <0.001 | 146 | <0.001 |
| 382, 322, 384 | L, K, I | G, E, T | 104 | 0.169 | 221 | <0.001 | 158 | <0.001 |
| 382, 322, 420 | L, K, L | G, E, G | 59 | 1.00 | 245 | <0.001 | 142 | <0.001 |
| 382, 322, 429 | L, K, A | G, E, S | 35 | 1.00 | 254 | <0.001 | 124 | <0.001 |
| 378, 1111, 1179 | M, F, D | T, K, N | 92 | 0.996 | 316 | <0.001 | 156 | <0.001 |
| 384, 1111, 1179 | I, F, D | G, K, N | 119 | <0.001 | 316 | <0.001 | 192 | <0.001 |

TABLE 7-continued

Concentration RebM, ratio of concentration RebM/concentration RebA produced and ratio of concentration RebM/concentration Total steviol glycosides (including RebA, RebB, RebD, RebM, stevioside, steviolbioside, rubusoside, steviol-13-monoside) produced in the supernatant of strain STVP002 transformed with transporters. Values represent molar concentrations normalized for production in strain STVP002 transformed with wild type transporter YALI0E25201, (first entry in Table 7).

| Position | aa WT | aa sub stitution | RebM | p-value RebM | Ratio RebM/ RebA | p-value ratio RebM/ RebA | Ratio RebM/ Total SGs | p-value ratio RebM/ Total SGs |
|---|---|---|---|---|---|---|---|---|
| 384, 1111, 1179 | I, F, D | N, K, N | 122 | <0.001 | 327 | <0.001 | 190 | <0.001 |
| 386, 1111, 1179 | A, F, D | L, K, N | 111 | <0.001 | 206 | <0.001 | 156 | <0.001 |
| 425, 1111, 1179 | Q, F, D | L, K, N | 111 | 0.000 | 361 | <0.001 | 197 | <0.001 |
| 425, 1111, 1179 | Q, F, D | A, K, N | 130 | <0.001 | 311 | <0.001 | 189 | <0.001 |
| 425, 1111, 1179 | Q, F, D | M, K, N | 128 | <0.001 | 331 | <0.001 | 194 | <0.001 |
| 421, 1111, 1179 | A, F, D | F, K, N | 128 | <0.001 | 326 | <0.001 | 193 | <0.001 |
| 420, 384 | L, I | G, S | 91 | 0.996 | 217 | <0.001 | 153 | <0.001 |
| 420, 384 | L, I | G, T | 96 | 0.902 | 228 | <0.001 | 150 | <0.001 |
| 420, 429 | L, A | G, S | 36 | 1.00 | 260 | <0.001 | 137 | <0.001 |
| 429, 384 | A, I | S, S | 124 | <0.001 | 163 | <0.001 | 145 | <0.001 |
| 429, 384 | A, I | S, T | 56 | 1.00 | 224 | <0.001 | 125 | <0.001 |
| 429 | A | S | 129 | <0.001 | 168 | <0.001 | 147 | <0.001 |
| 969, 1060, 891 | G, A, Y | N, T, T | 50 | 1.00 | 258 | <0.001 | 135 | <0.001 |
| 969, 1060, 890 | G, A, I | N, T, P | 86 | 1.00 | 287 | <0.001 | 161 | <0.001 |
| 969, 1060, 977 | G, A, F | N, T, A | 126 | <0.001 | 275 | <0.001 | 174 | <0.001 |
| 969, 1060, 977 | G, A, F | N, T, Q | 65 | 1.00 | 279 | <0.001 | 141 | <0.001 |
| 969, 1060, 998 | G, A, F | N, T, A | 89 | 1.000 | 273 | <0.001 | 166 | <0.001 |
| 969, 1060, 1107 | G, A, S | N, T, Y | 83 | 1.00 | 257 | <0.001 | 152 | <0.001 |
| 969, 1060, 1108 | G, A, A | N, T, K | 79 | 1.00 | 260 | <0.001 | 147 | <0.001 |
| 969, 1060, 1112 | G, A, I | N, T, N | 35 | 1.00 | 255 | <0.001 | 137 | <0.001 |
| 969, 1060, 1115 | G, A, V | N, T, G | 69 | 1.00 | 266 | <0.001 | 142 | <0.001 |
| 969, 1060, 1118 | G, A, M | N, T, A | 107 | 0.059 | 238 | <0.001 | 147 | <0.001 |
| 969, 1060, 1120 | G, A, A | N, T, M | 63 | 1.00 | 265 | <0.001 | 147 | <0.001 |
| 1107, 977 | S, F | Y, A | 92 | 0.996 | 227 | <0.001 | 157 | <0.001 |
| 1107, 1112 | S, I | Y, N | 47 | 1.00 | 239 | <0.001 | 130 | <0.001 |
| 1111, 1179, 891 | F, D, Y | K, N, T | 56 | 1.00 | 188 | <0.001 | 122 | <0.001 |
| 1111, 1179, 890 | F, D, I | K, N, P | 82 | 1.00 | 185 | <0.001 | 137 | <0.001 |
| 1111, 1179, 969, 1060 | F, D, G, A | K, N, N, T | 65 | 1.00 | 279 | <0.001 | 138 | <0.001 |
| 1111, 1179, 977 | F, D, F | K, N, A | 70 | 1.00 | 234 | <0.001 | 140 | <0.001 |
| 1111, 1179, 977 | F, D, F | K, N, Q | 71 | 1.00 | 211 | <0.001 | 142 | <0.001 |
| 1111, 1179, 998 | F, D, F | K, N, A | 56 | 1.00 | 222 | <0.001 | 131 | <0.001 |
| 1111, 1179, 1107 | F, D, S | K, N, Y | 57 | 1.00 | 254 | <0.001 | 133 | <0.001 |
| 1111, 1179, 1108 | F, D, A | K, N, K | 49 | 1.00 | 244 | <0.001 | 127 | <0.001 |
| 1111, 1179, 1112 | F, D, I | K, N, N | 53 | 1.00 | 259 | <0.001 | 130 | <0.001 |
| 1111, 1179, 1115 | F, D, V | K, N, G | 85 | 1.00 | 205 | <0.001 | 137 | <0.001 |
| 1111, 1179, 1118 | F, D, M | K, N, A | 55 | 1.00 | 255 | <0.001 | 136 | <0.001 |
| 1111, 1179, 1120 | F, D, A | K, N, M | 59 | 1.00 | 224 | <0.001 | 133 | <0.001 |
| 1111, 1179 | F, D | K, N | 121 | <0.001 | 231 | <0.001 | 166 | <0.001 |

TABLE 7-continued

Concentration RebM, ratio of concentration RebM/concentration RebA produced and ratio of concentration RebM/concentration Total steviol glycosides (including RebA, RebB, RebD, RebM, stevioside, steviolbioside, rubusoside, steviol-13-monoside) produced in the supernatant of strain STVP002 transformed with transporters. Values represent molar concentrations normalized for production in strain STVP002 transformed with wild type transporter YALI0E25201, (first entry in Table 7).

| Position | aa WT | aa substitution | RebM | p-value RebM | Ratio RebM/RebA | p-value ratio RebM/RebA | Ratio RebM/Total SGs | p-value ratio RebM/Total SGs |
|---|---|---|---|---|---|---|---|---|
| 1112, 891 | I, Y | N, T | 55 | 1.00 | 208 | <0.001 | 122 | <0.001 |
| 1112, 890 | I, I | N, P | 81 | 1.00 | 231 | <0.001 | 150 | <0.001 |
| 1112, 977 | I, F | N, A | 66 | 1.00 | 245 | <0.001 | 116 | <0.001 |
| 1112, 977 | I, F | N, Q | 83 | 1.00 | 221 | <0.001 | 145 | <0.001 |
| 1112, 998 | I, F | N, A | 72 | 1.00 | 188 | <0.001 | 132 | <0.001 |
| 1112, 1108 | I, A | N, K | 69 | 1.00 | 279 | <0.001 | 147 | <0.001 |
| 1112, 1115 | I, V | N, G | 51 | 1.00 | 282 | <0.001 | 137 | <0.001 |
| 1112, 1118 | I, M | N, A | 48 | 1.00 | 250 | <0.001 | 134 | <0.001 |
| 1112, 1120 | I, A | N, M | 120 | <0.001 | 177 | <0.001 | 144 | <0.001 |
| 1112 | I | N | 106 | 0.008 | 161 | <0.001 | 131 | <0.001 |
| 424, 1111, 1179 | P, F, D | L, K, N | 58 | 1.00 | 365 | <0.001 | 152 | <0.001 |
| 386, 1111, 1179 | A, F, D | I, K, N | 118 | <0.001 | 272 | <0.001 | 157 | <0.001 |
| 1012 | V | L | 47 | 1.00 | 262 | <0.001 | 131 | <0.001 |
| 1016 | D | E | 40 | 1.00 | 270 | <0.001 | 140 | <0.001 |
| 1017 | S | A | 99 | 0.658 | 133 | <0.001 | 118 | <0.001 |
| 1018 | I | L | 103 | 0.145 | 108 | 0.006 | 110 | <0.001 |
| 1018 | I | V | 105 | 0.024 | 118 | <0.001 | 112 | <0.001 |
| 1019 | E | G | 90 | 0.999 | 126 | <0.001 | 114 | <0.001 |
| 1020 | R | A | 106 | 0.027 | 135 | <0.001 | 125 | <0.001 |
| 1021 | S | A | 101 | 0.383 | 106 | 0.012 | 107 | 0.0002 |
| 1021 | S | N | 81 | 1.00 | 127 | <0.001 | 116 | <0.001 |
| 1021 | S | W | 57 | 1.00 | 205 | <0.001 | 127 | <0.001 |
| 1059 | S | E | 111 | <0.001 | 125 | <0.001 | 122 | <0.001 |
| 1060 | A | N | 73 | 1.00 | 173 | <0.001 | 129 | <0.001 |
| 1060 | A | S | 101 | 0.398 | 107 | 0.012 | 106 | 0.0016 |
| 1061 | Y | G | 107 | 0.003 | 112 | <0.001 | 111 | <0.001 |
| 1062 | F | L | 106 | 0.016 | 107 | 0.010 | 107 | 0.0003 |
| 1127 | E | A | 97 | 0.813 | 115 | <0.001 | 110 | <0.001 |
| 1127 | E | N | 89 | 1.000 | 139 | <0.001 | 124 | <0.001 |
| 1128 | N | D | 105 | 0.071 | 122 | <0.001 | 117 | <0.001 |
| 255 | I | A | 79 | 1.00 | 141 | <0.001 | 107 | 0.0002 |
| 257 | A | C | 105 | 0.014 | 110 | 0.000 | 111 | <0.001 |
| 257 | A | L | 58 | 1.00 | 161 | <0.001 | 118 | <0.001 |
| 258 | H | N | 103 | 0.144 | 110 | 0.000 | 115 | <0.001 |
| 258 | H | Q | 70 | 1.00 | 146 | <0.001 | 128 | <0.001 |
| 258 | H | S | 107 | 0.014 | 111 | 0.000 | 114 | <0.001 |
| 315 | K | A | 73 | 1.00 | 115 | 0.004 | 121 | <0.001 |
| 318 | A | K | 93 | 0.997 | 114 | 0.000 | 106 | 0.0007 |
| 319 | I | K | 92 | 0.998 | 107 | 0.006 | 109 | <0.001 |
| 320 | I | A | 102 | 0.245 | 131 | <0.001 | 122 | <0.001 |
| 321 | V | N | 100 | 0.550 | 116 | <0.001 | 105 | 0.0032 |
| 322 | K | A | 100 | 0.514 | 107 | 0.016 | 109 | 0.0001 |
| 322 | K | L | 96 | 0.903 | 129 | <0.001 | 113 | <0.001 |
| 322 | K | V | 90 | 1.000 | 113 | <0.001 | 109 | 0.0001 |
| 323 | L | W | 88 | 1.00 | 148 | <0.001 | 114 | <0.001 |
| 324 | T | A | 99 | 0.622 | 106 | 0.019 | 108 | 0.0001 |
| 326 | K | E | 98 | 0.783 | 113 | <0.001 | 111 | <0.001 |
| 328 | V | E | 83 | 1.00 | 131 | <0.001 | 116 | <0.001 |

The results in Table 7 illustrate that transformants with transporter variants listed in Table 7 result in higher production of RebM, a higher production of RebM compared to RebA, and/or a higher production of RebM compared to total steviol glycosides. All variants listed in Table 7 have a higher extracellular production of RebM over RebA and a higher extracellular production of RebM over total steviol glycosides. In addition, 21 transporter variants listed in Table 7 also have higher extracellular RebM production compared to the reference transporter.

Many variants seem to have lower overall activity. The transporter variants described in this example are expressed using the native YALI025201 promotor. Upon expressing the transporter with a stronger promotor, it is expected that the overall activity will be restored, or even exceeding the levels seen in the reference strain. Hence by using higher expression, one may retain the specificity (e.g. RebM transport over RebA transport) yet increase the overall transport activity of the cell.

REFERENCES

Bay D. C. et al., *Biochimica et Biophysica Acta*, (2008) 1778: 1814-1838.
Krogh A. et al., *Journal of Molecular Biology*, (2001) 305(3): 567-580.
Saier M. H. et al., *Nucleic Acids Research*, (2014) 42: D251-D258.
Sonnhammer E. L. L. et al. "A hidden Markov model for predicting transmembrane helices in protein sequences" in Glasgow J. et al. *Proceedings of the Sixth International Conference on Intelligent Systems for Molecular Biology*, (1998) 175-182; Menlo Park, CA, AAAI Press.
Wilkens S., *F1000Prime Reports*, (2015) 7:14 (doi: 10.12703/P7-14).
WO 2013/110673 A1.
WO 2014/122328 A1.
WO 2015/007748 A1.
WO 2016/023844 A1
Yang N., *Annual Review of Biophysics*, (2015) 44: 257-283.

```
SEQUENCE LISTING

Sequence total quantity: 6
SEQ ID NO: 1           moltype = DNA  length = 4296
FEATURE                Location/Qualifiers
misc_feature           1..4296
                       note = Polynucleotide sequence of the Open Reading Frame
                       (ORF) belonging to the Yarrowia lipolytica transporter
                       YALI0E25201
source                 1..4296
                       mol_type = other DNA
                       organism = Yarrowia lipolytica
SEQUENCE: 1
atgggtaaaa ccgaagtgac acaggagagt ctagaatgcg ggtcggtcac gtcctcgctg 60
gggaaaaagc ccttctccat catcacactc ttcaccggca gacgcattcc tccggtacct 120
actgaaaaac cagattcggc cgaagaacgg gccgggattc tgtcaaaatt gacctggcaa 180
tggcttagtc cattgttgaa agtgagtatg gctataggat aacttctgat gtcttcttca 240
atactaacac agactggtta cttacgaaac attgaacgtg aggatctgta taaagtgaga 300
gagagaaact cggcggctgt gatccagcag cgacttgaat ccaatctcga aaaacaatac 360
gccaagtacc acgccaaact gctcaagaaa ggactctcgg agcaagaggc gcatctcaag 420
ctgcaagatt cagccaaacc cctcgtcttg gctcttaacc agacgttttt ttggaagttc 480
tggctagccg gactgtttgc cctagtcaag gacctctgtg gaatcgcctc agctatggtg 540
tcacgtgttc tgatcgaata cattcaagac agatatctct acaggggggac agaccgggaa 600
cctaaggtcg gccgaggagt cggcccctcg ataggcctat ttctactggc cgtaggagtc 660
actttcttct tcaaccacat gttctacaat gtcaagatgg ttggagctca ggctcgtgca 720
gctctggtgg ccgtcatcta cagcaagagt acccgtttga gcgccaaggg ccgagctcaa 780
tacaccacag gcaagatcac aaacttggca gctattgacg cacatcgagt tgatctcagt 840
tgtgaatctt tccactacat tactatcttt ttgcctgttg tgggttgtgc cattgctgta 900
ctcgtggtca acctcaaggt cgcagctcta gttggaattg cgaccatgat tgtcttgatc 960
tttgtcgtcg caggcatcac catcttctct atgaagctgc gagccatcat tgtcaagctc 1020
acggataagc gagtcacgta tatccgagaa gctctgcagt cgattagaat catcaagtac 1080
tacggctggg aggttcctta ctgtgacaag atcaagaagg tgcgtcttga cgagacccgt 1140
aactacgcca agatgggctc gattcgagga acagccattg ggtactctc ggcactccct 1200
attttggcag gagcgttgtc tttcatcacc tacgctgctc taggtcatgg aactgatcct 1260
gctcgaatgt tctcttctct gacgcttttc aatttactcc tgcctgctct tgctgttctt 1320
ccccaggccc tccaggctgc tggagacgct cgagtggctc tcagacgtat ccagcggttc 1380
cttggggccg aggagtcgac tcccactaca gtttttgacg ctactcttga atctactgat 1440
gacgctgtga ttgtggaaga cgcctctttc atctggccag aagttgtcga tgataagagc 1500
gacaaagaga aggctaaaga tgcaaagaag gaggaaaagg ataagaagaa ggccgagaag 1560
aaggccaaga aggcggccaa gaaggcggcc aaggagatcg cggtggttgt ggaagaggag 1620
gtggaacacg aaaagaccga gggatccagt gagtctgaaa agggtactct taagtcgact 1680
ttcaagggct tcaacaacct gtctttcaaa atcaagcggg gtgaatttgt cgttgttacc 1740
ggtcccattg gttctggaaa gtcgtctctt cttgctgcca tcactggatc tatggttttg 1800
acaggcggtt ccgtgcgagt gtcgtccaca gagtggattg gatgtctgga gccgtggatt 1860
caaaacgcca cagttcgaga taacattgtg tttgggcgaa aattcgactc tgaatggtat 1920
agaactgtgg ttactgcctg tcagctgagc caggatctca aaataatgac tcacggagac 1980
aataccatga ttggagagcg aggcatcaca gtttcgggcg gtcaaaaagc tcgaatcaac 2040
ctcgcacgtg ctatatatgg aaaccccgag attctcatca tggacgacgt cctgtcggct 2100
gtggacgctc gagtaggtgc tggtattgtg gacgattgtc ttcgaggctt agccaagaac 2160
tccactcgaa ttctggccac ccatcagctg tctgtcctgc ctaaggctga tcatgtgatt 2220
ttcatggatg ccgaaggcca gtttcatatt ggtacgtacc aagagctgga ggctgacaat 2280
gagcagttca aggctctttt ggcggctggt tccatgtcca aggaggaggt ggttgctgtc 2340
gacgagactg aggttgttat tgaaggcgat cttgaagacg actgcgataa caaggaggag 2400
tatgaggatg cagctgagac catttccatt ttggcagatg ccactcaaga gctgcaaaag 2460
gtgaccacta cagtctcggc atttgaggag aacgataaca tgatggagga agaagagcga 2520
```

```
atgagagatg cagttggttt gcatgtgtac tggcagtatt ttcgtcaggc caacccagt   2580
agggtcaagg taatgatgtt cattggcatg atcttcattt ccatgattgt gattgccttt   2640
ctgtttgtct tcacatctgt atggctctcg ttctggacag gtgaccgttt ccatgcctcc   2700
agaaacttct acaccggaat ttacatcatg ctgggtattc ttctgcttct tgctgtggca   2760
ggatacatga ttgtcaatga gatcaactct gccatggcaa caagaaatct acacaatcat   2820
gctttggact cggtgttcgc tgcacgaact tctttcttcg ataccactcc tcagggtcgt   2880
atcatcaacc ggttcacccg agacacagac tctctggata cgagctggc tatgcgattg   2940
actatgttgt tctttggcgt ctccgcattc ttctccaact tcctgcttac ttgtgtctac   3000
gttccttatg tgactcttgt gcttgtccct gtcggtttg tcttctacgt ttctctaggt   3060
tactaccgaa agtcagctcg tgaagtcaag cgaattgact ccattgaacg gtcgcacatg   3120
atgagtgtct tcaacgagtc catttccggt atgcccgtca tcatcatgta caaggcccag   3180
catcggctca tgaacaagct tcaggctact ctcgatgata tggacagtgc ctacttcctc   3240
actgctgcaa ccagcgatg gctgtctctc cgtctggatg gtctgggttc tttggtcgtt   3300
ctggtgggca ctattcttgt tgctgtcgga gtctttgatc tcacccctc caacatggt   3360
ctgatcattt ccgcggcctc ctttatcccc gaagtcatgt ctatggttgc ccaggccgtt   3420
gctgaactcg aaaactgcat gaacgccaca gagcgaattc tttactacaa ggacaacatt   3480
cctgctgagg ctgctcgaga agtggacggt acagagctcg accagcgacc caactggcct   3540
gagcagggag ccatcagctt caacaatgtg tccatgaagt accgagatgg acttcctac   3600
gtgctcaagt cattgtctgt cgactttcag ggaggacaca aggtgggtat ctgtggacga   3660
acaggagccg gtaagagtac catccttcag actctgtatc gaattgtgga gcttgctgag   3720
ggttctatta ctattgatgg tgttgacatt tcgactattg gactgcatca gcttcggtct   3780
cagttgtcca tcattcccca ggagccagtt tgttcctgg gcaccatccg gtctaatttg   3840
gatcctctgg agcaatactc tgatgctgag ctatggggtt ctctacgacg tctctggactt   3900
ctcgatgaag agagactga gggtaagttt catctggatc aaaaggtgga ggctgacggc   3960
agcaacttct ctctaggtga gcgacagctg ctgactctag cccgagcact gcttagaaac   4020
accaaaattt tggtgctgga cgaagccaca tcaaatgtcg actacaagc ggacaagctg   4080
gttcaggaga ccatttcacg ggagtttggc cactgcacga ttctgtgtat cgcccatcga   4140
ctgcgaacca ttgccaagta tgatcgtatt ttggtgcttg agtccggcga gatcaaccag   4200
tacgacacgc cctggaactt gtacaacgac aaggagggta ttttccgagg tatgtgtgac   4260
acctccgggt tgaacgaggt agacttcaac aagtga                             4296

SEQ ID NO: 2            moltype = DNA   length = 6595
FEATURE                 Location/Qualifiers
misc_feature            1..6595
                        note = Genomic sequence of the Yarrowia lipolytica
                         transporter YALI0E25201 comprising a 1000 bp flanking
                         sequence upstream of the ORF, the ORF and, downstream of
                         the ORF, the terminator sequence (300 bp) followed by a
                         999 bp flanking sequence
source                  1..6595
                        mol_type = other DNA
                        organism = Yarrowia lipolytica
SEQUENCE: 2
cacaaagtac aatacaagta catactgtac ctgtgagtca tagtgacatg agaaaccatc    60
gaaggggcac acactcactc acactgtgaa ttggctctgg tcgactgcct gatgctccta   120
taatcgatct acacaccaac tccttttctca tccgcatgga tatagtttca tatcagtgtg   180
catggtgcaa aacgccgttt gccacccaat agtgttctgt gcactaatttt gacagcgaat   240
ttgccactgt ggggaacgtg ggaggaact ggaactacgg tactcgttcg aagttccgat    300
ccgaccggtg tgtgtcgagc aatgagtct gtgaaacctg tagtggtgct cgtggtggtg    360
gtggtggtgg ttgcacttgc agcatgtaag cagctgacgc gtcgcttaat agcacagtca   420
gttcgtatac tgtgatactt caatggtgtc aggaaggtga agaaacaacg ggtaataagt   480
catgttccat ttattttgaa cttgctgctt gaagtaggtt tggagactgc gttcggtgca   540
ttagcttctt gatatggagg cacggctctt cggggtccga ggtcgtggat agaagttgga   600
aagaggttct cggggttctt gtagatgaaa aaaacgacga agttgagata attaaacact   660
gtggagaaga gatatcgact gctgtgggtc acataacgtc ttatatacgc gccaattctt   720
tcaccaaccc gcaagtcccc aaactcaatc cagaagacta tcaatttttag acatgtatcg   780
gtcacatcaa tcgccgataa ccaaccagca agtggggaga cgccacctttt ttctcgcagc   840
ttttatactc ggcactgcgg cgttgctact taacctcctt gaatctcgat tggactgcta   900
gatcattgag atcagtcgac aaacagctca gatcagccac agatcagaca agctgatttca   960
gatcatcagt ttctcacacc acaccctcag tcttccacac atgggtaaaa ccgaagtgac   1020
acaggagagt ctagaatgcg ggtcggtcac gtcctcgctg ggaaaaagc ccttctccat   1080
catcacactc ttcaccggca gacgcattcc tccggtacct actgaaaaac cagattcggc   1140
cgaagaacgg gccgggattc tgtcaaaatt gacctggcaa tggcttagtc cattgttgaa   1200
agtgagtatg gctataggat aacttctgat gtcttcttca atactaacac agactggtta   1260
cttacgaaac attgaacgtg aggatctgta taagtgaga gagagaaact cggcggctgt   1320
gatccagcag cgacttgaat ccaatctcga aaaacaatac gccaagtacc acgccaaact   1380
gctcaagaaa ggactctcgg agcaagaggc gcatctcaag ctgcaagatt cagccaaacc   1440
cctcgtcttg gctcttaacc agacgttttt ttggaagttc tggctagccg gactgtttgc   1500
cctagtcaag gaccctctgt gaatcgcctc agctatggtc tcacgtgttc tgatcgaata   1560
cattcaagac agatatctct acaggggac agaccgggaa cctaaggtcg gcgaggagt   1620
cggcccctcg ataggctat ttctactggc cgtaggagtc actttcttct tcaaccacat   1680
gttctacaat gtcaagatgg ttggagctca ggctcgtgca gctctggtgg ccgtcatcta   1740
cagcaagagt acccgtttga gcgccaaggg ccgagctcaa tacaccacag gcaagatcac   1800
aaacttggca gctattacg cacatcgagt tgatctcagt tgtgaatctt tccactacat   1860
tactatcttt ttgcctgttg tgggttgtgc cattgctcca ctcgtggtca acctcaaggt   1920
cgcagctcta gttggaattg cgaccatgat tgtcttcatc ttgtcgtcg caggcatcac   1980
catcttctct atgaagctgc gagccatcat tgtcaagctc acggataagc gagtcacgta   2040
tatccgagaa gctctgcagt cgattagaat catcaagtac tacggctggg aggttcctta   2100
ctgtgacaag atcaagaagg tgcgtcttga cgagaccgt aactacgcca agatgggctc   2160
```

```
gattcgagga acagccattg gtatgtttca ggcactccct attttggcag gagcgttgtc  2220
tttcatcacc tacgctgctc taggtcatgg aactgatcct gctcgaatgt tctcttctct  2280
gacgcttttc aatttactcc tgcctgctct tgctgttctt ccccaggccc tccaggctgc  2340
tggagacgct cgagtggctc tcagacgtat ccagcggttc cttggggccg aggagtcgac  2400
tcccactaca gttttgacg ctactcttga atctactgat gacgctgtga ttgtggaaga  2460
cgcctctttc atctgccag aagttgtcga tgataagagc gacaaagaga aggctaaaga  2520
tgcaaagaag gaggaaaagg ataagaagaa ggccgagaag aaggccaaga aggcggccaa  2580
gaaggcggcc aaggagatcg cggtggttgt ggaagaggag gtggaacacg aaaagaccga  2640
gggatccagt gagtctgaaa agggtactct taagtcgact ttcaagggct tcaacaacct  2700
gtctttcaaa atcaagcggg gtgaatttgt cgttgttacc ggtcccattg gttctggaaa  2760
gtcgtctctt cttgctgcca tcactggatc tatggttttg acaggcggtt ccgtgcgagt  2820
gtcgtccaca gagtggattg gatgtctgga gccgtggatt caaaacgcca cagttcgaga  2880
taacattgtg tttgggcgaa aattcgactc tgaatggtat agaactgtgg ttactgcctg  2940
tcagctgagc caggatctca aaataatgac tcacggaagc aataccatga ttggagagcg  3000
aggcatcaca gtttcgggcg tcaaaaagc tcgaatcaac ctcgcacgtg ctatatatgg  3060
aaaccccgag attctcatca tggacgacgt cctgtcggct gtggacgctc gagtaggtgc  3120
tggtattgtg gacgattgtc ttcgaggctt agccaagaac tccactcgaa ttctggccac  3180
ccatcagctg tctgtgctgc ctaaggctga tcatgtgatt ttcatggatg ccgaaggcca  3240
gtttcatatt ggtacgtacc aagagctgga ggctgacaat gagcagttca aggctctttt  3300
ggcggctggt tccatgtcca aggaggaggt ggttgctgtc gacgagactg aggttgttat  3360
tgaaggcgat cttgaagacg actgcgataa caaggaggag tatgaggatg cagctgagac  3420
catttccatt ttggcagatg ccactcaaga gctgcaaaag gccaccacta cagtctcggc  3480
atttgaggag aacgataaca tgatggagga agaagagcga atgagagtg cagttggttt  3540
gcatgtgtac tggcagtatt ttcgtcaggc caaccccagt agggtcaagg taatgatgtt  3600
cattggcatg atcttcattt ccatgattgt gattgccttt ctgtttgtct tcacatctgt  3660
atggctctcg ttctggacag gtgaccgttt ccatgcctcc agaaacttct acaccggaat  3720
ttacatcatg ctgggtattc ttctgcttct tgctgtggca ggatacatga ttgtcaatga  3780
gatcaactct gccatggcag caagaaatct acacaatcat gctttggact cggtgttcgc  3840
tgcacgaact tctttcttcg ataccactcc tcagggtcgt atcatcaacc ggttcacccg  3900
agacacagac tctctggata acgagctggc tatgcgattg actatgttgt tctttggcgt  3960
ctccgcattc ttctccaact tcctgcttac ttgtgtctac gttccttatg tgactcttgt  4020
gcttgtccct gtcggttttg tcttctacgt ttctctaggt tactaccgaa agtcagctcg  4080
tgaagtcaag cgaattgact ccattgaacg gtcgcacatg atgagtgtct tcaacgagtc  4140
catttccggt atgcccgtca tcatcatgta caaggcccag catcggctca tgaacaagct  4200
tcaggctact ctcgatgata tggacagtgc ctacttcctg actgctgcaa accagccatg  4260
gctgtctctc cgtctggatg gtctgggttc ttttggtcgt tctggtggcca ctattcttgt  4320
tgctgtcgga gtctttgatc tcaccccttc aacatgggt ctgatcattt ccgcggcctc  4380
ctttatcccc gaagtcatgt ctatggttgc ccaggccgtt gctgaactcg aaaactgcat  4440
gaacgccaca gagcgaattc tttactacaa ggacaacatt cctgctgagg ctgctcgaga  4500
agtggacggt acagagctcg accagcgacc caactggcct gagcagggag ccatcagctt  4560
caacaatgtg tccatgaagt accgagatgg acttccttac gtgctcaagt cattgtctgt  4620
cgactttcag ggaggacaca aggtgggtat ctgtggacga acaggagccg gtaagagtac  4680
catctgcag actctgtatc gaattgtgga gcttgctgag ggttctatta ctattgatgg  4740
tgttgacatt tcgactattg gactgcatca gcttcggtct cagttgtcca tcattccca  4800
ggagccagtt ttgttcctgg gcaccatccg gtctaattg gatcctctgg agcaatactc  4860
tgatgctgag ctatggggtt ctctacgacg gtctggactt ctcgatgaag gagagactga  4920
gggtaagttt catctggatc aaaaggtgga ggctgacggc agcaacttct ctctaggtga  4980
gcgacagctg ctgactctag cccgagcact gcttagaaac accaaaattt tggtgctgga  5040
cgaagccaca tcaaatgtcg actacaagac ggacaagctg gttcaggaga ccatttcacg  5100
ggagtttggc cactgcacga ttctgtgtat cgcccatcga ctgcgaacca ttgccaagta  5160
tgatcgtatt ttggtgcttg agtccggcga gatcaaccag tacgacacgc cctggaactt  5220
gtacaacgac aaggagggta ttttccgagg tatgtgtgac acctccgggt gaacgaggt  5280
agacttcaac aagtgaaaaa ttacgatgag ggtagacagt ctgagatgag actgataaat  5340
tatagagaaa aaatgtttga ttatagcagt agtgaatgta ttgtatgtaa taagtggcca  5400
atcttggaat ggtggcctcc gtattaattc ttaccgaact cgtagtcacc tttgtaaagc  5460
gacagtgtct gttcacattg ggtcaaacat gtaaatattg tagctacgta gtctatagtc  5520
ctaagagaac gataccatag aaaatcgatt tccacagccg atcttttttg tcggtggcaa  5580
tcagtacttt tcttttttctc aatattcgca ccgttcacaa ttacctcaaa ttgcttttcg  5640
gaagttgaga taggatcggg tcgggagtgt ttcggaagcg ggtcgggccg aaaaagccgt  5700
taccgggttt ccgaaactgc ctctgaaag atgtggaatc acatggggga gtattagcag  5760
tgcctttgag atgttctcgg tgagctctgc ttagctttca ttaggcaaga gccgtgcttg  5820
atagatttct cgagcatgta gctcatacta gctcttgcac cattgaggtg aggtgaatga  5880
ggtgctgtat ccgtttttga tgcaccaat tgataataat tgtgagttat ggcaacgcaa  5940
agagtttgtt agaatgataag cagagaaatt ccatgcgaaa caccgctata tggcttgttt  6000
ggcagagtcc tacttcagct gtggtgttca tgccgaacta tagtatgtac gagaacaaag  6060
tagcccatta caatcacaag cggtcgtcga tactcaatca aaaataaacg tccagccaat  6120
gctacatcaa agacaccctt caaacagcat ctggacccgc agacttgcca ctatggatgc  6180
aggacgttaa ggggtggcat caagccgcag agagactata cgatcttgg ctaactgtaa  6240
ttaggtgaca attgagagtg atgtccactg ataggctact tttacgagtg ataagtgaga  6300
gcgatagcct cggcgtctaa aaagggagca caatgagtgt cttattacga gtacggtgat  6360
atacattgtt gttcatctat agtttggatg tgtgtcaggt gcccgttttt atcagttcac  6420
cctacgagta catacagtat gtacttgtac agtacactta caagatctag tttgaccatg  6480
caactgaaca gaatacaact aaacagattt agttacacgc atacacacaa tagggtgtat  6540
aacctcagat atcagtccca tacttatagt actgtattgt tgtccttcac attct        6595
```

SEQ ID NO: 3        moltype = AA  length = 1414
FEATURE             Location/Qualifiers
REGION              1..1414
                        note = MISC_FEATURE - Amino acid sequence of the Yarrowia

```
                            lipolytica transporter YALI0E25201
source                      1..1414
                            mol_type = protein
                            organism = Yarrowia lipolytica
SEQUENCE: 3
MGKTEVTQES LECGSVTSSL GKKPFSIITL FTGRRIPPVP TEKPDSAEER AGILSKLTWQ    60
WLSPLLKTGY LRNIEREDLY KVRERNSAAV IQQRLESNLE KQYAKYHAKL LKKGLSEQEA   120
HLKLQDSAKP LVLALNQTFF WKFWLAGLFA LVKDLCGIAS AMVSRVLIEY IQDRYLYRGT   180
DREPKVGRGV GPSIGLFLLA VGVTFFFNHM FYNVKMVGAQ ARAALVAVIY SKSTRLSAKG   240
RAQYTTGKIT NLAAIDAHRV DLSCESFHYI TIFLPVVGCA IAVLVVNLKV AALVGIATMI   300
VLIFVVAGIT IFSMKLRAII VKYLTDKRVTY IREALQSIRI IKYYGWEVPY CDKIKKVRLD   360
ETRNYAKMGS IRGTAIGMFQ ALPILAGALS FITYAALGHG TDPARMFSSL TLFNLLLPAL   420
AVLPQALQAA GDARVALRRI QRFLGAEEST PTTVFDATLE STDDAVIVED ASFIWPEVVD   480
DKSDKEKAKD AKKEEKDKKK AEKKAKKAAK KAAKEIAVVV EEEVEHEKTE GSSESEKGTL   540
KSTFKGFNNL SFKIKRGEFV VVTGPIGSGK SSLLAAITGS MVLTGGSVRV SSTEWIGCLE   600
PWIQNATVRD NIVFGRKFDS EWYRTVVTAC QLSQDLKIMT HGDNTMIGER GITVSGGQKA   660
RINLARAIYG NPEILMDDV LSAVDARVGA GIVDDCLRGL AKNSTRILAT HQLSVLPKAD   720
HVIFMDAEGQ FHIGTYQELE ADNEQFKALL AAGSMSKEEV VAVDETEVVI EGDLEDDCDN   780
KEEYEDAAET ISILADATQE LQKVTTTVSA FEENDNMMEE EERMRDAVGL HVYWQYFRQA   840
NPSRVKVMMF IGMIFISMIV IAFLVFTSV WLSFWTGDRF HASRNFYTGI YIMLGILLLL   900
AVAGYMIVNE INSAMAARNL HNHALDSVFA ARTSFFDTTP QGRIINRFTR DTDSLDNELA   960
MRLTMLFFGV SAFFSNFLLT CVYVPYVTLV LVPVGFVFYV SLGYYRKSAR EVKRIDSIER  1020
SHMMSVFNES ISGMPVIIMY KAQHRLMNKL QATLDDMDSA YFLTAANQRW LSLRLDGLGS  1080
LVVLVATILV AVGVFDLTPS NMGLIISAAS FIPEVMSMVA QAVAELENCM NATERILYYK  1140
DNIPAEAARE VDGTELDQRP NWPEQGAISF NNVSMKYRDG LPYVLKSLSV DFQGGHKVGI  1200
CGRTGAGKST ILQTLYRIVE LAEGSITIDG VDISTIGLHQ LRSQLSIIPQ EPVLFLGTIR  1260
SNLDPLEQYS DAELWGSLRR SGLLDEGETE GKFPHLDQKVE ADGSNFSLGE RQLLTLARAL  1320
LRNTKILVLD EATSNVDYKT DKLVQETISR EFGHCTILCI AHRLRTIAKY DRILVLESGE  1380
INQYDTPWNL YNDKEGIFRG MCDTSGLNEV DFNK                              1414

SEQ ID NO: 4                moltype = AA  length = 500
FEATURE                     Location/Qualifiers
REGION                      1..500
                            note = Truncated 3-hydroxy-3-methylglutaryl coenzyme A
                             reductase
source                      1..500
                            mol_type = protein
                            organism = synthetic construct
SEQUENCE: 4
MTQSVKVVEK HVPIVIEKPS EKEEDTSSED SIELTVGKQP KPVTETRSLD DLEAIMKAGK    60
TKLLEDHEVV KLSLEGKLPL YALEKQLGDN TRAVGIRRSI ISQQSNTKTL ETSKLPYLHY   120
DYDRVFGACC ENVIGYMPLP VGVAGPMNID GKNYHIPMAT TEGCLVASTM RGCKAINAGG   180
GVTTVLTQDG MTRGPCVSFP SLKRAGAAKI WLDSEEGLKS MRKAFNSTSR FARLQSLHST   240
LAGNLLFIRF RTTTGDAMGM NMISKGVEHS LAVMVKEYGF PDMDIVSVSG NYCTDKKPAA   300
INWIEGRGKS VVAEATIPAH IVKSVLKSEV DALVELNISK NLIGSAMAGS VGGFNAHAAN   360
LVTAIYLATG QDPAQNVESS NCITLMSNVD GNLLISVSMP SIEVGTIGGG TILEPQGAML   420
EMLGVRGPHI ETPGANAQQL ARIIASGVLA AELSLCSALA AGHLVQSHMT HNRSQAPTPA   480
KQSQADLQRL QNGSNICIRS                                              500

SEQ ID NO: 5                moltype = AA  length = 327
FEATURE                     Location/Qualifiers
REGION                      1..327
                            note = Variant geranylgeranyl-diphosphate synthase
source                      1..327
                            mol_type = protein
                            organism = synthetic construct
SEQUENCE: 5
MDYNSADFKE IWGKAADTAL LGPYNYLANN RGHNIREHLI AAFGAVIKVD KSDLETISHI    60
TKILHNSSLL VDDVEDNSML RRGLPAAHCL FEVPQTINSV NYMYFVALQE VLKLKSYDAV   120
SIFTEEMINL HRGQGMDLYW RETLTCPSED EYLEMVVHKT GGLFRLALRL MLSVASKQED   180
HEKINFDLTH LTDTLGVIYQ ILDDYLNLQS TELTENKGFC EDISEGKFSF PLIHSIRTNP   240
DNHEILNILK QRTSDASLKK YAVDYMRTET KSFDYCLKRI QAMSLKASSY IDDLAAAGHD   300
VSKLRAILHY FVSTSDCEER KYFEDAQ                                      327

SEQ ID NO: 6                moltype = AA  length = 525
FEATURE                     Location/Qualifiers
REGION                      1..525
                            note = Variant kaurenoic acid 13-hydroxylase
source                      1..525
                            mol_type = protein
                            organism = synthetic construct
SEQUENCE: 6
MESLVVHTVN AIWCIVIVGI FSVGYHVYGR AVVEQWRMRR SLKLQGVKGP PPSIFNGNVS    60
EMQRIQSEAK HNSGDNIISH DYSSTLFPHF DHWRKQYGRI YTYSTGLRQH LYINHPEMVK   120
```

```
ELSQTNSLDL GRITHVTKRL APILGNGIIT SNGPHWAHQR RIIAYEFTHD KVKGMVGLMV  180
ESAMPMLNKW EEMVEAEGGM GCDIRVDEDL KDVSADVIAK ACFGSNFSKG KAIFSKIRDL  240
LTAITKRSVL FRFNGFTDMV FGSKKHGDVD IDALEMELES SIWETVKERE RECKDTHKKD  300
LLQLILEGAM RSCDGNLWDK SAYRRFVVDN CKSIYFAGHD STAVSVSWCL MLLALNPSWQ  360
EKIRDEILSS CKNGIPDAES IPNLKTVTMV IQETMRLYPP APIVGREASK DIRLGDLVVP  420
KGVCIWTLIP ALHRDPEIWG PDANDFKPER FSEGISKACK YPQAYIPFGL GPRTCVGKNF  480
GMMEVKVLVS LIVSKFSFTL SPTYQHSPSH KLLVEPQHGV VIRVV                 525
```

The invention claimed is:

1. A recombinant cell capable of producing a steviol glycoside, wherein the cell comprises a nucleic acid sequence encoding a variant of a parent polypeptide, wherein the variant comprises an amino acid sequence having at least 90% sequence identity to SEQ ID NO: 3, and at least one of the following modifications: A375F, I376W, I384G, L420G, P424L, any amino acid other than F at position 968, F977Q, S1107Y, I1112N, and/or A1120M.

2. The recombinant cell according to claim 1, wherein the cell expresses or overexpresses the variant polypeptide.

3. The recombinant cell according to claim 1 which comprises one or more recombinant nucleotide sequence(s) encoding:
 a polypeptide having ent-copalyl pyrophosphate synthase activity;
 a polypeptide having ent-Kaurene synthase activity;
 a polypeptide having ent-Kaurene oxidase activity; and
 a polypeptide having kaurenoic acid 13-hydroxylase activity.

4. The recombinant cell according to claim 1 which comprises a recombinant nucleic acid sequence encoding a polypeptide having NADPH-cytochrome p450 reductase activity.

5. The recombinant cell according to claim 1 which comprises a recombinant nucleic acid sequence encoding one or more of:

(i) a polypeptide having UGT74G1 activity;
(ii) a polypeptide having UGT2 activity;
(iii) a polypeptide having UGT85C2 activity; and
(iv) a polypeptide having UGT76G1 activity.

6. The recombinant cell according to claim 1, wherein the recombinant cell is a *Saccharomyces cerevisiae* cell, a *Yarrowia lipolytica* cell, a *Candida krusei* cell, an *Issatchenkia orientalis* cell or an *Escherichia coli* cell.

7. The recombinant cell according to claim 1, wherein the ability of the cell to produce geranylgeranyl diphosphate (GGPP) is upregulated.

8. The recombinant cell according to claim 1 which comprises a nucleic acid sequence encoding one or more of:
 a polypeptide having hydroxymethylglutaryl-CoA reductase activity; or
 a polypeptide having farnesyl-pyrophosphate synthetase activity.

9. A process for the preparation of steviol glycoside which comprises fermenting the recombinant cell according to claim 1 in a suitable fermentation medium and, optionally, recovering the steviol glycoside.

10. The process of claim 9 for the preparation of a steviol glycoside, wherein the process is carried out on an industrial scale.

* * * * *